US006777187B2

(12) United States Patent
Makarov et al.

(10) Patent No.: US 6,777,187 B2
(45) Date of Patent: Aug. 17, 2004

(54) GENOME WALKING BY SELECTIVE AMPLIFICATION OF NICK-TRANSLATE DNA LIBRARY AND AMPLIFICATION FROM COMPLEX MIXTURES OF TEMPLATES

(75) Inventors: Vladimir L. Makarov, Ann Arbor, MI (US); Emmanuel Kamberov, Ann Arbor, MI (US); Irina Sleptsova, Ann Arbor, MI (US)

(73) Assignee: Rubicon Genomics, Inc., Ann Arbor, MI (US)

( * ) Notice: Subject to any disclaimer, the term of this patent is extended or adjusted under 35 U.S.C. 154(b) by 0 days.

(21) Appl. No.: 09/999,018

(22) Filed: Nov. 15, 2001

(65) Prior Publication Data

US 2003/0064376 A1 Apr. 3, 2003

Related U.S. Application Data

(60) Provisional application No. 60/288,205, filed on May 2, 2001.

(51) Int. Cl.[7] .......................... C12Q 1/68; C12P 19/34; C07H 21/02; C07H 21/04; C07H 19/00
(52) U.S. Cl. .......................... 435/6; 435/7.1; 435/91.1; 435/91.2; 435/199; 536/22.1; 536/23.1; 536/24.3; 536/24.31; 536/24.32; 536/24.33
(58) Field of Search .......................... 435/6, 91.2, 199; 536/23.1, 24.3; 702/20

(56) References Cited

U.S. PATENT DOCUMENTS

| 4,710,465 A | 12/1987 | Weissman et al. |
| 4,942,124 A | 7/1990 | Church |
| 5,149,625 A | 9/1992 | Church et al. |
| 5,508,169 A | 4/1996 | Deugau et al. |
| 5,518,901 A | 5/1996 | Murtagh |
| 5,648,213 A | 7/1997 | Reddy et al. |
| 5,695,971 A | 12/1997 | Kadokami et al. |
| 5,858,671 A | 1/1999 | Jones |
| 6,063,604 A | 5/2000 | Wick et al. |
| 6,117,634 A | 9/2000 | Langmore et al. |
| 6,124,120 A | 9/2000 | Lizardi |
| 6,197,557 B1 * | 3/2001 | Makarov et al. ............. 435/6 |
| 2002/0028458 A1 * | 3/2002 | Lexow et al. ............. 435/6 |
| 2002/0102577 A1 * | 8/2002 | Raillard et al. ............. 435/6 |

FOREIGN PATENT DOCUMENTS

| WO | IB-99/18241 | 4/1999 |
| WO | IB-00/18960 | 4/2000 |
| WO | IB-00/24929 | 5/2000 |
| WO | IB-00/28084 | 5/2000 |
| WO | IB-00/60121 | 10/2000 |

OTHER PUBLICATIONS

Guilfoyle, Richard A., et al., Ligation–mediated PCR amplification of specific fragments from a Class–II restriction endonuclease total digest, Nucleic Acids Research vol. 25, No. 9 (1997), pp. 1854–1858.

(List continued on next page.)

Primary Examiner—Jeffrey Siew
(74) Attorney, Agent, or Firm—Fulbright & Jaworski, LLP

(57) ABSTRACT

Improved methods and reagents for chromosome walking of nucleic acid are discussed herein. A library of amplifiable nick translation molecules is generated, and a chromosome walk is initiated from a known sequence in the nucleic acid by producing at least one nick translate molecule, sequencing part of the nick translate molecule, and producing a second nick translate molecule by initiating the primer extension from the region of the obtained sequence of the prior nick translate molecule.

58 Claims, 39 Drawing Sheets

OTHER PUBLICATIONS

Hagiwara, Koichi and Harris, Curtis C., 'Long distance sequencer' method; a novel strategy for large DNA sequencing projects, Nucleic Acids Research vol. 24, No. 12 (1996), pp. 2460–2461.

Makorov, Vladimir L., et al., Long G. Tails at Both Ends of Human Chromosomes Suggest a C Strand Degradation Mechanism for Telomere Shortening, Cell, vol. 88 (1997), pp. 657–666.

Rosenthal, Andrew, et al., Genomic walking and sequencing by oligo–cassette mediated polymerase chain reaction, Nucleic Acids Research, vol. 18, No. 10 (1990), pp. 3095–3096.

Smith, Douglas R., Ligation–mediated PCR of Restriction Fragments from Large DNA Molecules, PCR Methods and Applications, vol. 2 (1992), pp. 21–27.

Unrau, Paul and Deugau, Kenneth V., Non–cloning amplification of specific DNA fragments from whole genomic DNA digests using DNA 'indexers', Gene, 145 (1994), pp. 163–169.

Walker, G. Terrance, et al., Isothermal in vitro amplication of DNA by a restriction enzyme / DNA polymerase system, Proc. Natl. Acad. Sci. USA vol. 89 (1992), pp. 392–396, Applied Biological Sciences.

Walker, G. Terrance, et al., Strand displacement amplification—an isothermal, in vitro DNA amplification technique, Nucleic Acids Research, vol. 20, No. 7 (1992), pp. 1691–1696.

* cited by examiner

A minimal tiling path is created by the amplification and sequencing of the PENTameres $P_1$, $P_5$, $P_9$, $P_{13}$, $P_{17}$ and $P_{21}$ from the PENTAmer library R Immobilization of the PENT products on the magnetic beads Ligation of the 3' end of the PENT product to the adaptor B Washing Immobilization of the PENT products on the magnetic beads Ligation of the 3' end of the PENT product to the adaptor B Washing A ligation reaction between the product of
primer extension and the oligonucleotide $P_A$
hybridized to the adaptor A

⇩

C

DU-Glycosylase -dependent
degradation of the template
library

⇩

D

PCR amplification of the targeted
PENTamere X using primers B' and C

⇩

E

Polymerase extension reaction primed by the oligomer
assembled by a ligation of the selected octamers $P_1, P_2, P_3$

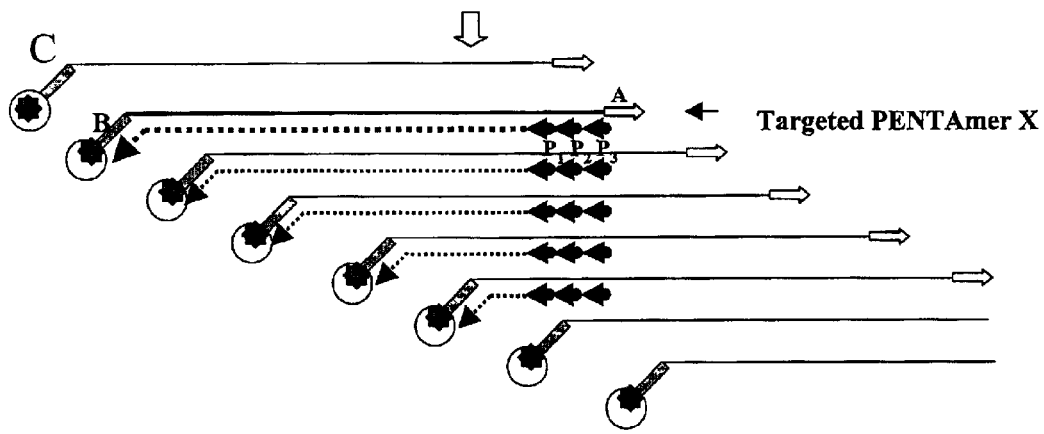

A ligation reaction between the product of
primer extension and the oligonucleotide $P_A$
hybridized to the adaptor A

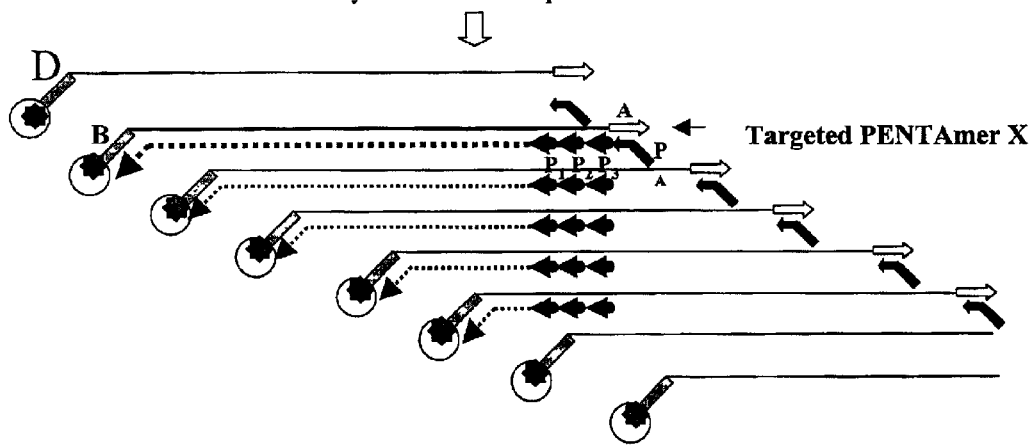

DU-Glycosylase-dependent degradation of the
template library followed by PCR amplification
of the targeted PENTAmer X using primers B'
and C

FIG. 14B

Polymerase extension reaction primed by the oligomer
assembled by a ligation of the selected octamers $P_1$, $P_2$, $P_3$
and oligo $P_A$

C ⇩

Targeted PENTAmer X

DU-Glycosylase-dependent degradation of the
template PENTamere library

D ⇩

PCR amplification of the targeted PENTamere
X using primers B' and C

⇩

E

A

Single-strand complementary
(secondary) PENTamere
library

Polymerase extension reaction primed by selected
oligonucleotide P and heat sensitive DNA polymerase

⇩

B

C  ⇩

Heat inactivation of DNA polymerase

⇩

D     Ligation of the biotinylated oligonucleotide $P_A$-Bio
complementary to the adaptor sequence A

⇩

Magnetic bead capture of the targeted PENTAmer X

E

⇩

PCR amplification of the targeted PENTamere X using primers B and C or B and A

F

⇩ or

BH = PENTAmers originating at Bam H I restriction sites
SU = PENTAmers originating at Sau 3AI restriction sites

SEQUENCE LISTING

<160> NUMBER OF SEQ ID NOS: 57

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
cggtgcatgt gtatcgtccg sagttcaaca acctca     36

<210> SEQ ID NO 2
<211> LENGTH: 9
<212> TYPE: DNA
<213> ORGANISM: Artificial Sequence
<220> FEATURE:
<223> OTHER INFORMATION: Primer

<400> SEQUENCE: 2 gatccccat     9

<210> SEQ ID NO 3
<211> LENGTH: 9
<212> TYPE: DNA
<213> ORGANISM: Artificial Sequence
<220> FEATURE:
<223> OTHER INFORMATION: Primer

<400> SEQUENCE: 3 ttccagacg     9

```
<210> SEQ ID NO 4
<211> LENGTH: 9
<212> TYPE: DNA
<213> ORGANISM: Artificial Sequence
<220> FEATURE:
<223> OTHER INFORMATION: Primer

<400> SEQUENCE: 4 ataaggctg                                                                 9

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
cattaaatca tcgcagtagc attgactcag cc                                      32

<210> SEQ ID NO 6
<211> LENGTH: 9
<212> TYPE: DNA
<213> ORGANISM: Artificial Sequence
<220> FEATURE:
<223> OTHER INFORMATION: Primer

<400> SEQUENCE: 6 cattaaatc                                                                 9

<210> SEQ ID NO 7
<211> LENGTH: 9
<212> TYPE: DNA
<213> ORGANISM: Artificial Sequence
<220> FEATURE:
<223> OTHER INFORMATION: Primer

<400> SEQUENCE: 7 gagcgggcg                                                                 9

<210> SEQ ID NO 8
<211> LENGTH: 9
<212> TYPE: DNA
<213> ORGANISM: Artificial Sequence
<220> FEATURE:
<223> OTHER INFORMATION: Primer

<400> SEQUENCE: 8 cagtacgcc                                                                 9

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
atacaagcca tcgcagtagc attgactcag cc                                      32

<210> SEQ ID NO 10
<211> LENGTH: 9
<212> TYPE: DNA
<213> ORGANISM: Artificial Sequence
<220> FEATURE:
```

```
<223> OTHER INFORMATION: Primer

<400> SEQUENCE: 10 atacaagcc                                                                    9

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
cggtgcatgt gtatcgtccg agt                                                   23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggctgagtca atgctactgc gat                                                   23

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gatctgaggt tgttgaagcg t                                                     21

<210> SEQ ID NO 14
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: Ribonucleotide at 9, 14, and 19

<400> SEQUENCE: 14
ttgcctaauc gaautgggua aacg                                                  24

<210> SEQ ID NO 15
<211> LENGTH: 14
<212> TYPE: DNA
<213> ORGANISM: Artificial Sequence
<220> FEATURE:
<223> OTHER INFORMATION: Primer

<400> SEQUENCE: 15
cttcaacaac ctca                                                             14

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
```

-continued ttgcctaatc gaattgggta aacg                                          24

<210> SEQ ID NO 17
<211> LENGTH: 42
<212> TYPE: DNA
<213> ORGANISM: Artificial Sequence
<220> FEATURE:
<223> OTHER INFORMATION: Primer

<400> SEQUENCE: 17
ttgcctaatc gaattgggta aacgcttcaa caacctcaga tc                      42

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
ttacgatacg agtctttgtc accttccgcg atgatcttgc agactt                  46

<210> SEQ ID NO 19
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: n equals any nucleotide

<400> SEQUENCE: 19
aagtctgcaa gatcatcgcg gaaggtgaca aagactcgta tcgtaannnn c            51

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
aagtctgcaa gatcatcgcg gaa                                           23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
aagtctgcaa gatcatcgcg gaa                                           23

<210> SEQ ID NO 22
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(46)
<223> OTHER INFORMATION: n equals any nucleotide

```
<400> SEQUENCE: 22
acgggctagc aaaatagcgc tgtccngatc tgaggttgtt gaagcg          46

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ggacagcgct attttgctag cccgt                                 25

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
ggtgacaaag actcgtatcg taa                                   23

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
ttgcctaatc gaattgggta aacg                                  24

<210> SEQ ID NO 26
<211> LENGTH: 60
<212> TYPE: DNA
<213> ORGANISM: Artificial Sequence
<220> FEATURE:
<223> OTHER INFORMATION: Primer

<400> SEQUENCE: 26
gatctgaggt tgttgaagcg tttacccaat tcgattaggc aaaggtctgc aagatcatcg    60

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ttacccaatt cgattaggca a                                     21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cgcttcaaca acctcagatc                                       20

<210> SEQ ID NO 29
<211> LENGTH: 42
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(42)
<223> OTHER INFORMATION: Ribonucleotide at 23, 30 and 36

<400> SEQUENCE: 29
gatctgaggt tgttgaagcg ttuacccaau tcgatuaggc aa                           42

<210> SEQ ID NO 30
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(38)
<223> OTHER INFORMATION: Ribonucleotide at 20, 25 and 30

<400> SEQUENCE: 30
actccaacaa cttcgcaaau gggtuaagcu aatccgtt                                38

<210> SEQ ID NO 31
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: N equals any nucleotide

<400> SEQUENCE: 31
aagtctgcaa gatcatcgcg gaaggtgaca aagactcgta tcgtaannnn c                 51

<210> SEQ ID NO 32
<211> LENGTH: 46
<212> TYPE: DNA
<213> ORGANISM: Artificial Sequence
<220> FEATURE:
<223> OTHER INFORMATION: Primer

<400> SEQUENCE: 32
ttcagacgtt ctagtagcgc cttccactgt ttctgagcat agcatt                       46

<210> SEQ ID NO 33
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 33
gacnnnnngt c                                                             11

<210> SEQ ID NO 34
<211> LENGTH: 13
<212> TYPE: DNA
<213> ORGANISM: Artificial Sequence
<220> FEATURE:
```

-continued

```
<223> OTHER INFORMATION: Primer
<220> FEATURE:
<221> NAME/KEY: misc_feature
<222> LOCATION: (1)..(10)
<223> OTHER INFORMATION: N equals any nucleotide
<220> FEATURE:
<221> NAME/KEY: misc_feature
<222> LOCATION: (11)..(11)
<223> OTHER INFORMATION: N equals C or T
<220> FEATURE:
<221> NAME/KEY: misc_feature
<222> LOCATION: (13)..(13)
<223> OTHER INFORMATION: N equals any nucleotide

<400> SEQUENCE: 34
nacnnnngta ncn                                                    13

<210> SEQ ID NO 35
<211> LENGTH: 12
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(12)
<223> OTHER INFORMATION: N equals any nucleotide

<400> SEQUENCE: 35
cgannnnnnt gc                                                     12

<210> SEQ ID NO 36
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 36
gccnnnnngg c                                                      11

<210> SEQ ID NO 37
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(10)
<223> OTHER INFORMATION: N equals any nucleotide

<400> SEQUENCE: 37 gatnnnnatc                                                        10

<210> SEQ ID NO 38
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 38
```

```
ccnnnnnnng g                                                     11

<210> SEQ ID NO 39
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 39
gcannnnntg c                                                     11

<210> SEQ ID NO 40
<211> LENGTH: 12
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(12)
<223> OTHER INFORMATION: N equals any nucleotide

<400> SEQUENCE: 40
ccannnnnnt gg                                                    12

<210> SEQ ID NO 41
<211> LENGTH: 12
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(12)
<223> OTHER INFORMATION: N equals any nucleotide

<400> SEQUENCE: 41
gacnnnnnng tc                                                    12

<210> SEQ ID NO 42
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 42
cctnnnnnag g                                                     11

<210> SEQ ID NO 43
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(10)
<223> OTHER INFORMATION: N equals any nucleotide
```

```
<400> SEQUENCE: 43 gagtcnnnnn                                                          10

<210> SEQ ID NO 44
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(7)
<223> OTHER INFORMATION: N equals any nucleotide
<220> FEATURE:
<221> NAME/KEY: misc_feature
<222> LOCATION: (8)..(8)
<223> OTHER INFORMATION: R is A or G

<400> SEQUENCE: 44 caynnnnrtg                                                          10

<210> SEQ ID NO 45
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 45
gcnnnnnnng c                                                        11

<210> SEQ ID NO 46
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 46
ccannnnntg g                                                        11

<210> SEQ ID NO 47
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(10)
<223> OTHER INFORMATION: N equals any nucleotide

<400> SEQUENCE: 47 gacnnnngtc                                                          10

<210> SEQ ID NO 48
<211> LENGTH: 13
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(13)
<223> OTHER INFORMATION: N equals any nucleotide

<400> SEQUENCE: 48
ggccnnnnng gcc                                                           13

<210> SEQ ID NO 49
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(15)
<223> OTHER INFORMATION: N equals any nucleotide

<400> SEQUENCE: 49
ccannnnnnn nntgg                                                         15

<210> SEQ ID NO 50
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(10)
<223> OTHER INFORMATION: N equals any nucleotide

<400> SEQUENCE: 50 gaannnnttc                                                               10

<210> SEQ ID NO 51
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 51
gacnnnnngt c                                                             11

<210> SEQ ID NO 52
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: N is A or T
<220> FEATURE:
<221> NAME/KEY: misc_feature
<222> LOCATION: (4)..(11)
<223> OTHER INFORMATION: N equals any nucleotide

<400> SEQUENCE: 52
```
ccnggnnnng g        11

<210> SEQ ID NO 53
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(11)
<223> OTHER INFORMATION: N equals any nucleotide

<400> SEQUENCE: 53
ccaggnnntg g        11

<210> SEQ ID NO 54
<211> LENGTH: 13
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: N is A or T
<220> FEATURE:
<221> NAME/KEY: misc_feature
<222> LOCATION: (6)..(13)
<223> OTHER INFORMATION: N equals any nucleotide

<400> SEQUENCE: 54
ggccnggnng gcc        13

<210> SEQ ID NO 55
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: N equals A or T
<220> FEATURE:
<221> NAME/KEY: misc_feature
<222> LOCATION: (5)..(11)
<223> OTHER INFORMATION: N equals any Nucleotide

<400> SEQUENCE: 55
gccnggnngg c        11

<210> SEQ ID NO 56
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: N equals any nucleotide
<220> FEATURE:
<221> NAME/KEY: misc_feature
<222> LOCATION: (8)..(8)
<223> OTHER INFORMATION: N is A or T

<400> SEQUENCE: 56 ggtnaccngg        10

```
-continued

<210> SEQ ID NO 57
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(9)
<223> OTHER INFORMATION: N equals any nucleotide
<220> FEATURE:
<221> NAME/KEY: misc_feature
<222> LOCATION: (14)..(14)
<223> OTHER INFORMATION: N is A or T

<400> SEQUENCE: 57
ggccnnnnng gccngg                                                    16
```

GENOME WALKING BY SELECTIVE AMPLIFICATION OF NICK-TRANSLATE DNA LIBRARY AND AMPLIFICATION FROM COMPLEX MIXTURES OF TEMPLATES

This application claims priority to U.S. Provisional Patent Application Serial No. 60/288,205, filed May 2, 2001.

FIELD OF THE INVENTION

The present invention relates generally to the fields of molecular biology and genomes. Particularly, it concerns utilization of DNA libraries for amplifying and analyzing DNA. More particularly, it concerns utilizing DNA libraries of nick translated products for chromosome walking.

DESCRIPTION OF RELATED ART

A. DNA Preparation Using in Vivo and in Vitro Amplification and Multiplexed Versions Thereof Because the amount of any specific DNA molecule that can be isolated from even a large number of cells is usually very small, the only practical methods to prepare enough DNA molecules for most applications involve amplification of specific DNA molecules in vivo or in vitro. There are basically six general methods important for manipulating DNA for analysis: 1) in vivo cloning of unique fragments of DNA, 2) in vitro amplification of unique fragments of DNA, 3) in vivo cloning of random libraries (mixtures) of DNA fragments, 4) in vitro preparation of random libraries of DNA fragments, 5) in vivo cloning of ordered libraries of DNA, 6) in vitro preparation of ordered libraries of DNA. The beneficial effect of amplifying mixtures of DNA is that it facilitates analysis of large pieces of DNA (e.g., chromosomes) by creating libraries of molecule that are small enough to be analyzed by existing techniques. For example the largest molecule that can be subjected to DNA sequencing methods is less than 2000 bases long, which is many orders of magnitude shorter than single chromosomes of organisms. Although short molecules can be analyzed, considerable effort is required to assemble the information from the analysis of the short molecules into a description of the larger piece of DNA.

1. In Vivo Cloning of Unique DNA

Unique-sequence source DNA molecules can be amplified by separating them from other molecules (e.g., by electrophoresis), ligating them into an autonomously replicating genetic element (e.g., a bacterial plasmid), transfecting a host cell with the recombinant genetic element, and growing a clone of a single transfected host cell to product many copies of the genetic element having the insert with the same unique sequence as the source DNA (Sambrook, et al., 1989).

2. In Vitro Amplification of Unique DNA

There are many methods designed to amplify DNA in vitro. Usually these methods are used to prepare unique DNA molecules from a complex mixture, e.g., genomic DNA or a artificial chromosome. Alternatively a restricted set of molecules can be prepared as a library that represents a subset of sequences in the complex mixture. These amplification methods include PCR, rolling circle amplification, and strand displacement (Walker, et al. 1996a; Walker, et al. 1996b; U.S. Pat. No. 5,648,213; U.S. Pat. No. 6,124,120).

The polymerase chain reaction (PCR) can be used to amplify specific regions of DNA between two known sequences (U.S. Pat. No. 4,683,195, U.S. Pat. No. 4,683, 202; Frohman et al., 1995). PCR involves the repetition of a cycle consisting of denaturation of the source (template) DNA, hybridization of two oligonucleotide primers to known sequences flanking the region to the amplified, primer extension using a DNA polymerase to synthesize strands complementary to the DNA region located between the two primer sites. Because the products of one cycle of amplification serve as source DNA for succeeding cycles, the amplification is exponential. PCR can synthesize large numbers of specific molecules quickly and inexpensively.

The major disadvantages of the PCR method to amplify DNA are that 1) information about two flanking sequences must be known in order to specify the sequences of the primers, 2) synthesis of primers is expensive, 3) the level of amplification achieved depends strongly on the primer sequences, source DNA sequence, and the molecular weight of the amplified DNA and 4) the length of amplified DNA is usually limited to less than 5 kb, although "long-distance" PCR (Cheng, 1994) allows molecules as long as 20 kb to be amplified.

"One-sided PCR" techniques are able to amplify unknown DNA adjacent to one known sequence. These techniques can be divided into 3 categories: a) ligation-mediated PCR, facilitated by addition of a universal adaptor sequence to a terminus usually created by digestion with a restriction endonuclease; b) universal primer-mediated PCR, facilitated by a primer extension reaction initiated at arbitrary sites c) terminal transferase-mediated PCR, facilitated by addition of a homonucleotide "tail" to the 3' end of DNA fragments; and d) "inverse PCR, facilitated by circularization of the template molecules. These techniques can be used to amplify successive regions along a large DNA template in a process sometimes called "chromosome walking."

Ligation-mediated PCR is practiced in many forms. Rosenthal et al. (1990) outlined the basic process of amplifying an unknown region of DNA immediately adjacent to a known sequence located near the end of a restriction fragment. Reiley et al. (1990) used primers that were not exactly complementary with the adaptors in order to suppress amplification of molecules that did not have a specific priming site. Jones (1993) and Siebert (1995; U.S. Pat. No. 5,565,340) used long universal primers that formed intrastrand "panhandle" structures that suppressed PCR of molecules having two universal adaptors. Arnold (1994) used "vectorette" primers having unpaired central regions to increase the specificity of one-sided PCR. Macrae and Brenner (1994) amplified short inserts from a Fugu genomic clone library using nested primers from a specific sequence and from vector sequences. Lin et al. (1995) ligated an adaptor to restriction fragment ends that had an overhanging 5' end and employed hot-start PCR with a single universal anchor primer and nested specific-site primers to specifically amplify human sequences. Liao et al. (1997) used two specific site primers and 2 universal adaptors, one of which had a blocked 3' end to reduce non-specific background, to amplify zebrafish promoters. Devon et al. (1995) used "splinkerette-vectorette" adaptors with special secondary structure in order to decrease non-specific amplification of molecules with two universal sequences during ligation-mediated PCR. Padegimas and Reichert (1998) used phosphorothioate-blocked oligonucleotides and exo III digestion to remove the unligated and partially ligated molecules from the reactions before performing PCR, in order to increase the specificity of amplification of maize sequences. Zhang and Gurr (2000) used ligation-mediated hot-start PCR of restriction fragments using nested primers in order to amplify up to 6 kb of a fungal genome. The large amplicons were subsequently directly sequenced using primer extension.

To increase the specificity of ligation-mediated PCR products, many methods have been used to "index" the amplification process by selection for specific sequences adjacent to one or both termini (e.g., Smith, 1992; Unrau, 1994; Guilfoyle, 1997; U.S. Pat. No. 5,508,169).

One-sided PCR can also be achieved by direct amplification using a combination of unique and non-unique primers. Harrison et al. (1997) performed one-sided PCR using a degenerate oligonucleotide primer that was complementary to an unknown sequence and three nested primers complementary to a known sequence in order to sequence transgenes in mouse cells. U.S. Pat. No. 5,994,058 specifies using a unique PCR primer and a second, partially degenerate PCR primer to achieve one-sided PCR. Weber et al. (1998) used direct PCR of genomic DNA with nested primers from a known sequence and 1–4 primers complementary to frequent restriction sites. This technique does not require restriction digestion and ligation of adaptors to the ends of restriction fragments, Terminal transferase can also be used in one-sided PCR. Cormack and Somssich (1997) were able to amplify the termini of genomic DNA fragments using a method called RAGE (rapid amplification of genome ends) by a) restricting the genome with one or more restriction enzymes, b) denaturing the restricted DNA, c) providing a 3' polythymidine tail using terminal transferase, and d) performing two rounds of PCR using nested primers complementary to a known sequence as well as the adaptor. Rudi et al. (1999) used terminal transferase to achieve chromosome walking in bacteria using a method of one-sided PCR that is independent of restriction digestion by a) denaturation of the template DNA, b) linear amplification using a primer complementary to a known sequence, c) addition of a poly C "tail" to the 3' end of the single-stranded products of linear amplification using a reaction catalyzed by terminal transferase, and d) PCR amplification of the products using a second primer within the known sequence and a poly-G primer complementary to the poly-C tail in the unknown region. The products amplified by Rudi (1999) have a very broad size distribution, probably caused by a broad distribution of lengths of the linearly-amplified DNA molecules.

RNA polymerase can also be used to achieve one-sided amplification of DNA. U.S. Pat. No. 6,027,913 shows how one-sided PCR can be combined with transcription with RNA polymerase to amplify and sequence regions of DNA with only one known sequence.

Inverse PCR (Ochman et al., 1988) is another method to amplify DNA based on knowledge of a single DNA sequence. The template for inverse PCR is a circular molecule of DNA created by a complete restriction digestion, which contains a small region of known sequence as well as adjacent regions of unknown sequence. The oligonucleotide primers are oriented such that during PCR they give rise to primer extension products that extend way from the known sequence. This "inside-out" PCR results in linear DNA products with known sequences at the termini.

The disadvantages of all "one-sided PCR" methods is that a) the length of the products are restricted by the limitation of PCR (normally about 2 kb, but with special reagents up to 50 kb); b) whenever the products are single DNA molecules longer than 1 kb they are too long to directly sequence; c) in ligation-mediated PCR the amplicon lengths are very unpredictable due to random distances between the universal priming site and the specific priming site(s), resulting in some products that are sometimes too short to walk significant distance, some which are preferentially amplified due to small size, and some that are too long to amplify and analyze, and d) in methods that use terminal transferase to add a polynucleotide tail to the end of a primer extension product, there is great heterogeneity in the length of the amplicons due to sequence-dependent differences in the rate of primer extension.

Strand displacement amplification (Walker, et al. 1996a; Walker, et al. 1996b; U.S. Pat. No. 5,648,213; U.S. Pat. No. 6,124,120) is a method to amplify one of more termini of DNA fragments using an isothermal strand displacement reaction. The method is initiated at a nick near the terminus of a double-stranded DNA molecule, usually generated by a restriction enzyme, followed by a polymerization reaction by a DNA polymerase that is able to displace the strand complementary to the template strand. Linear amplification of the complementary strand is achieved by reusing the template multiple times by nicking each product strand as it is synthesized. The products are strands with 5' ends at a unique site and 3' ends that are various distances from the 5' ends. The extent of the strand displacement reaction is not controlled and therefore the lengths of the product strands are not uniform. The polymerase used for strand displacement amplification does not have a 5' exonuclease activity.

Rolling circle amplification (U.S. Pat. No. 5,648,245) is a method to increase the effectiveness of the strand displacement reaction by using a circular template. The polymerase, which does not have a 5' exonclease activity, makes multiple copies of the information on the circular template as it makes multiple continuous cycles around the template. The length of the product is very large—typically too large to be directly sequenced. Additional amplification is achieved if a second strand displacement primer is added to the reaction to used the first strand displacement product as a template.

3. In Vivo Cloning of DNA of Random Libraries

Libraries are collections of small DNA molecules that represent all parts of a larger DNA molecule or collection of DNA molecules (Primrose, 1998; Cantor and Smith, 1999). Libraries can be used for analytical and preparative purposes. Genomic clone libraries are the collection of bacterial clones containing fragments of genomic DNA. cDNA clone libraries are collections of clones derived from the mRNA molecules in a tissue.

Cloning of non-specific DNA is commonly used to separate and amplify DNA for analysis. DNA from an entire genome, one chromosome, a virus, or a bacterial plasmid is fragmented by a suitable method (e.g., hydrodynamic shearing or digestion with restriction enzymes), ligated into a special region of a bacterial plasmid or other cloning vector, transfected into competent cells, amplified as a part of a plasmid or chromosome during proliferation of the cells, and harvested from the cell culture. Critical to the specificity of this technique is the fact that the mixture of cells carrying different DNA inserts can be diluted and aliquoted such that some of the aliquots, whether on a surface or in a volume of solution, contain a single transfected cell containing a unique fragment of DNA. Proliferation of this single cell (in vivo cloning) amplifies this unique fragment of DNA so that it can be analyzed. This "shotgun" cloning method is used very frequently, because: 1) it is inexpensive, 2) it produces very pure sequences that are usually faithful copies of the source DNA, 3) it can be used in conjunction with clone screening techniques to create an unlimited amount of specific-sequence DNA, 4) it allows simultaneous amplification of many different sequences, 5) it can be used to amplify DNA as large as 1,000,000 bp long, and 6) the cloned DNA can be directly used for sequencing and other purposes.

a. Multiplex Cloning

Cloning is inexpensive, because many pieces of DNA can be simultaneously transfected into host cells. The general term for this process of mixing a number of different entities (e.g., electronic signals or molecules) is "multiplexing," and is a common strategy for increasing the number of signals or molecules that can be processed simultaneously and subsequently separated to recover the information about the individual signals or molecules. In the case of conventional cloning the recovery process involves diluting the bacterial culture such that an aliquot contains a single bacterium carrying a single plasmid, allowing the bacterium to multiply to create many copies of the original plasmid, and isolating the cloned DNA for further analysis.

The principle of multiplexing different molecules in the same transfection experiment is critical to the economy of the cloning method. However, after the transfection each clone must be grown separately and the DNA isolated separately for analysis. These steps, especially the DNA isolation step, are costly and time consuming. Several attempts have been made to multiplex steps after cloning, whereby hundreds of clones can be combined during the steps of DNA isolation and analysis and the characteristics of the individual DNA molecules recovered later. In one version of multiplex cloning the DNA fragments are separated into a number of pools (e.g., one hundred pools). Each pool is ligated into a different vector, possessing a nucleic acid tag with a unique sequence, and transfected into the bacteria. One clone from each transfection pool is combined with one clone from each of the other transfection pools in order to create a mixture of bacteria having a mixture of inserted sequences, where each specific inserted sequence is tagged with a unique vector sequence, and therefore can be identified by hybridization to the nucleic acid tag. This mixture of cloned DNA molecules can be subsequently separated and subjected to any enzymatic, chemical, or physical processes for analysis such as treatment with polymerase or size separation by electrophoresis. The information about individual molecules can be recovered by detection of the nucleic acid tag sequences by hybridization, PCR amplification, or DNA sequencing. Church has shown methods and compositions to use multiplex cloning to sequence DNA molecules by pooling clones tagged with different labels during the steps of DNA isolation, sequencing reactions, and electrophoretic separation of denatured DNA strands (U.S. Pat. Nos. 4,942,124; 5,149,625). The tags are added to the DNA as parts of the vector DNA sequences. The tags used can be detected using oligonucleotides labeled with radioactivity, fluorescent groups, or volatile mass labels (Cantor and Smith, 1999; U.S. Pat. Nos. 4,942,124; 5,149,625; 5,112,736; Richterich and Church, 1993). U.S. Pat. No. 5,714,318 is directed to a technique whereby the tag sequences are ligated to the DNA fragments before cloning using a universal vector. Furthermore, PCT WO 98/15644 specifies a method whereby the tag sequences added before transfection are amplified using PCR after electrophoretic separation of the denatured DNA.

b. Disadvantages

The disadvantage of preparing DNA by amplifying random fragments of DNA is that considerable effort is necessary to assemble the information within the short fragments into a description of the original, source DNA molecule. Nevertheless, amplified short DNA fragments are commonly used for many applications, including sequencing by the technique called "shotgun sequencing." Shotgun sequencing involves sequencing one or both ends of small DNA fragments that have been cloned from randomly-fragmented large pieces of DNA. During the sequencing of many such random fragments of DNA, overlapping sequences are identified from those clones that by chance contain redundant sequence information. As more and more fragments are sequenced more overlaps can be found from contiguous regions (contigs). As more and more fragments are sequenced the regions that are not represented become smaller and less frequent. However, even after sequencing enough fragments that the average region has been sequenced 5–10 times, there will still be gaps between contigs due to statistical sampling effects and to systematic under-representation of some sequences during cloning or PCR amplification (ref). Thus the disadvantage of sequencing random fragments of DNA is that 1) a 5–10 fold excess of DNA must be isolated, subjected to sequencing reactions, and analyzed before having large contiguous sequenced regions, and 2) there are still numerous gaps in the sequence that must be filled by expensive and time-consuming steps.

4. In Vitro Preparation of DNA as Random Libraries

DNA libraries can be formed in vitro and subjected to various selection steps to recover information about specific sequences. In vitro libraries are rarely used in genomics, because the methods that exist for creating such libraries do not offer advantages over cloned libraries. In particular the methods used to amplify the in vitro libraries are not able to amplify all of the DNA in an unbiased manner, because of the size and sequence dependence of amplification efficiency. WO 00/18960 describes how different methods of DNA amplification can be used to create a library of DNA molecules representing a specific subset of the sequences within the genome for purposes of detecting genetic polymorphisms. "Random-prime PCR" (U.S. Pat. Nos. 5,043,272; U.S. Pat. No. 5,487,985) "random-prime strand displacement" (U.S. Pat. No. 6,124,120) and "AFLP" (U.S. Pat. No. 6,045,994) are three examples of methods to create libraries that represent subsets of complex mixtures of DNA molecules.

Single-molecule PCR can be used to amplify individual randomly-fragmented DNA molecules (Lukyanov et al., 1996). In one method, the source DNA is first fragmented into molecules usually less than 10,000 bp in size, ligated to adaptor oligonucleotides, and extensively diluted and aliquoted into separate fractions such that the fractions often contain only a single molecule. PCR amplification of a fraction containing a single molecule creates a very large number of molecules identical to one of the original fragments. If the molecules are randomly fragmented, the amplified fractions represent DNA from random positions within the source DNA.

WO 00/15779A2 describes how a specific sequence can be amplified from a library of circular molecules with random genomic inserts using rolling circle amplification.

5. In Vivo Cloning of Ordered Libraries of DNA

Directed cloning is a procedure to clone DNA from different parts of a larger piece of DNA, usually for the purpose of sequencing DNA from different positions along the source DNA. Methods to clone DNA with "nested deletions" have been used to make "ordered libraries" of clones that have DNA starting at different regions along a long piece of source DNA. In one version, one end of the source DNA is digested with one or more exonuclease activities to delete part of the sequence (McCombie et al., 1991; U.S. Pat. No. 4,843,003). By controlling the extent of exonuclease digestion, the average amount of the deletion can be controlled. The DNA molecules are subsequently separated based on size and cloned. By cloning molecules with different molecular weights, many copies of identical DNA plasmids are produced that have inserts ending at controlled positions within the source DNA. Transposon insertion (Berg et al., 1994) is also used to clone different regions of source DNA by facilitating priming or cleavage at random positions in the plasmids, The size separation and recloning steps make both of these methods labor intensive and slow. They are generally limited to covering regions less than 10 kb in size and cannot be used directly on genomic DNA but rather cloned DNA molecules.

6. In Vitro Preparation of Ordered Libraries DNA

Ordered libraries have not been frequently created in vitro. Hagiwara (1996) used vectorette adaptors and exonuclease digestions to create a nested set of one-sided PCR products that could be used to walking across a cosmid after size separation. No methods are known to create ordered libraries of DNA molecules directly from genomic DNA.

B. DNA Physical Mapping to Create Ordered Clones

There is often a need to organize a library of randomly cloned DNA molecules into an ordered library where the clones are arranged according to position in the genome (Primrose, 1998; Cantor and Smith, 1999). Some of the purposes for creating an ordered library are 1) to compare overlapping clones to detect defects (e.g., deletions) in some of the clones, 2) to decide which clones should be used to determine the underlying DNA sequence with the least redundancy in sequencing effort, 3) to localize genetic features within the genome, 4) to access different regions of the genome on the basis of their relationship to the genetic map or proximity to another region, and 5) to compare the structure of the genomes of different individuals and different species. There are four basic methods for creating ordered libraries of clones: 1) hybridization to determine sequence homology among different clones, 2) fluorescent in situ hybridization (FISH), 3) restriction analysis, and 4) STS mapping.

1. Mapping by Hybridization

The first method usually involves hybridization of one clone or other identifiable sequence to all other clones in a library. Those clones that hybridize contain overlapping sequences. This method is useful for locating clones that overlap a common site (e.g., a specific gene) in the genome, but is too laborious to create an ordered library of an entire genome. In addition many organisms have large amounts of repetitive DNA that can give false indications of overlap between two regions. The resolution of the hybridization techniques is only as good as the distance between known sequences of DNA.

2. Mapping by FISH

The FISH method allows a particular sequence or limited set of sequences to be localized along a chromosome by hybridization of a fluorescently-labeled probe with a spread of intact chromosomes, followed by light-microscopic localization of the fluorescence. This technique is also only of use to locate a specific sequence or small number of sequences, rather than to create a physical map of the entire genome or an ordered library representing the entire genome. The resolution of the light microscope limits the resolution of FISH to about 1,000,000 bp. To map a single-copy sequence, the FISH probe usually needs to be about 10,000 long.

3. Mapping by Restriction Digestion

Mapping by restriction digestion is frequently used to determine overlaps between clones, thereby allowing ordered libraries of clones to be constructed. It involves assembly of a number of large clones into a contiguous region (contig) by analyzing the overlaps in the restriction patterns of related clones. This method is insensitive to the presence of repetitive DNA. The products of a complete or partial restriction digestion of every clone are size separated by electrophoresis and the molecular weights of the fragments analyzed by computer to find correlated sequences in different clones. The information from the restriction patterns produced by five or more restriction enzymes is usually adequate to determine not only which clones overlap, but also the extent of overlap and whether some of the clones have deletions, additions, rearrangements, etc. Physical mapping of restriction sites is a very tedious process, because of the very large numbers of clones that have to be evaluated. For example, >300,000 BAC clones of 100,000 bp length need to be analyzed to map the human genome. Using conventional techniques mapping two restriction sites would require at least 300,000 bacterial cultures and DNA isolations, as well as 600,000 restriction digestions and size separations.

4. Mapping by STS Amplification

Sequence tagged sites are sequences, often from the 3' untranslated portions of mRNA, that can be uniquely amplified in the genome. High-throughput methods employing sophisticated equipment have been devised to screen for the presence of tens of thousands of STSs in tens of thousands of clones. Two clones overlap to the extent that they share common STSs.

C. DNA Sequencing Reactions

DNA sequencing is the most important analytical tool for understanding the genetic basis of living systems. The process involves determining the positions of each of the four major nucleotide bases, adenine (A), cytosine (C), guanine (G), and thymine (T) along the DNA molecule(s) of an organism. Short sequences of DNA are usually determined by creating a nested set of DNA fragments that begin at a unique site and terminate at a plurality of positions comprised of a specific base. The fragments terminated at each of the four natural nucleic acid bases (A, T, G and C) are then separated according to molecular size in order to determine the positions of each of the four bases relative to the unique site. The pattern of fragment lengths caused by strands that terminate at a specific base is called a "sequencing ladder." The interpretation of base positions as the result of one experiment on a DNA molecule is called a "read." There are different methods of creating and separating the nested sets of terminated DNA molecules.

1. Maxim-Gilbert Method

The Maxim-Gilbert method involves degrading DNA at a specific base using chemical reagents. The DNA strands terminating at a particular base are denatured and electrophoresed to determine the positions of the particular base. The Maxim-Gilbert method involves dangerous chemicals, and is time- and labor-intensive. It is no longer used for most applications.

2. Sanger Method

The Sanger sequencing method is currently the most popular format for sequencing. It employs single-stranded DNA (ssDNA) created using special viruses like M13 or by denaturing double-stranded DNA (dsDNA). An oligonucleotide sequencing primer is hybridized to a unique site of the ssDNA and a DNA polymerase is used to synthesize a new strand complementary to the original strand using all four deoxyribonucleotide triphosphates (dATP, dCTP, dGTP, and dTTP) and small amounts of one or more dideoxyribonucleotide triphosphates (ddATP, ddCTP, ddGTP, and/or ddTTP), which cause termination of synthesis. The DNA is denatured and electrophoresed into a "ladder" of bands representing the distance of the termination site from the 5' end of the primer. If only one ddNTP (e.g., ddGTP) is used only those molecules that end with guanine will be detected in the ladder. By using ddNTPs with four different labels all four ddNTPs can be incorporated in the same polymerization reaction and the molecules ending with each of the four bases can be separately detected after electrophoresis in order to read the base sequence.

Sequencing DNA that is flanked by vector or PCR primer DNA of known sequence, can undergo Sanger termination reactions initiated from one end using a primer complementary to those known sequences. These sequencing primers are inexpensive, because the same primers can be used for DNA cloned into the same vector or PCR amplified using primers with common terminal sequences. Commonly-used electrophoretic techniques for separating the dideoxyribonucleotide-terminated DNA molecules are limited to resolving sequencing ladders shorter than 500–1000 bases. Therefore only the first 500–1000 nucleic acid bases can be "read" by this or any other method of sequencing the DNA. Sequencing DNA beyond the first 500–1000 bases requires special techniques.

3. Other Base-Specific Termination Methods

Other termination reactions have been proposed. One group of proposals involves substituting thiolated or boronated base analogs that resist exonuclease activity. After incorporation reactions very similar to Sanger reactions a 3' to 5' exonuclease is used to resect the synthesized strand to the point of the last base analog. These methods have no substantial advantage over the Sanger method.

Methods have been proposed to reduce the number of electrophoretic separations required to sequence large amounts of DNA. These include multiplex sequencing of large numbers of different molecules on the same electrophoretic device, by attaching unique tags to different molecules so that they can be separately detected. Commonly, different fluorescent dyes are used to multiplex up to 4 different types of DNA molecules in a single electrophoretic lane or capillary (U.S. Pat. No. 4,942,124). Less commonly, the DNA is tagged with large number of different nucleic acid sequences during cloning or PCR amplification, and detected by hybridization (U.S. Pat. No. 4,942,124) or by mass spectrometry (U.S. Pat. No. 4,942,124).

In principle, the sequence of a short fragment can be read by hybridizing different oligonucleotides with the unknown sequence, followed by deciphering the information to reconstruct the sequence. This "sequencing by hybridization" is limited to fragments of DNA <50 bp in length. It is difficult to amplify such short pieces of DNA for sequencing. However, even if sequencing many random 50 bp pieces were possible, assembling the short, sometimes overlapping sequences into the complete sequence of a large piece of DNA would be impossible. The use of sequencing by hybridization is currently limited to resequencing, that is testing the sequence of regions that have already been sequenced.

D. Preparing DNA for Determining Long Sequences

Because it is currently very difficult to separate DNA molecules longer than 1000 bases with single-base resolution, special methods have been devised to sequence DNA regions within larger DNA molecules. The "primer walking" method initiates the Sanger reaction at sequence-specific sites within long DNA. However, most emphasis is on methods to amplify DNA in such a way that one of the ends originates from a specific position within the long DNA molecule.

1. Primer Walking

Once part of a sequence has been determined (e.g., the terminal 500 bases), a custom sequencing primer can be made that is complementary to the known part of the sequence, and used to prime a Sanger dideoxyribonucleotide termination reaction that extends further into the unknown region of the DNA. This procedure is called "primer walking." The requirement to synthesize a new oligonucleotide every 400–1000 bp makes this method expensive. The method is slow, because each step is done in series rather than in parallel. In addition each new primer has a significant failure rate until optimum conditions are determined. Primer walking is primarily used to fill gaps in the sequence that have not been read after shotgun sequencing or to complete the sequencing of small DNA fragments <5,000 bp in length. However, WO 00/60121 addresses using a single synthetic primer for PCR to genome walk to unknown sequences from a known sequence. The 5'-blocked primer anneals to the template and is extended, followed by coupling to the extended product of a 3'-blocked oligonucleotide of known sequence, thereby creating a single stranded molecule having had only a single region of known target DNA sequence. By sequencing an amplified product from the extended product having the coupled 3'-blocked oligonucleotide, the process can be applied reiteratively to elucidate consecutive adjacent unknown sequences.

2. PCR Amplification

PCR can be used to amplify a specific region within a large DNA molecule. Because the PCR primers must be complementary to the DNA flanking the specific region, this method is usually used only to prepare DNA to "resequence" a region of DNA.

3. Nested Deletion and Transposon Insertion

As described in above, cloning or PCR amplification of long DNA with nested deletions brought about by nuclease cleavage or transposon insertion enables ordered libraries of DNA to be created. When exonuclease is used to progressively digest one end of the DNA there is some control over the position of one end of the molecule. However the exonuclease activity cannot be controlled to give a narrow distribution in molecular weights, so typically the exonuclease-treated DNA is separated by electrophoresis to better select the position of the end of the DNA samples before cloning. Because transposon insertion is nearly random, clones containing inserted elements have to be screened before choosing which clones have the insertion at a specific internal site. The labor-intense steps of clone screening make these methods impractical except for DNA less than about 10 kb long.

4. Junction-Fragment DNA Probes for Preparing Ordered DNA Clones

Collins and Weissman have proposed to use "junction-fragment DNA probes and probe clusters" (U.S. Pat. No. 4,710,465) to fractionate large regions of chromosomes into ordered libraries of clones. That patent proposes to size fractionate genomic DNA fragments after partial restriction digestion, circularize the fragments in each size-fraction to form junctions between sequences separated by different physical distances in the genome, and then clone the junctions in each size fraction. By screening all the clones derived from each size-fraction using a hybridization probe from a known sequence, ordered libraries of clones could be created having sequences located different distances from the known sequence. Although this method was designed to walk along megabase distances along chromosomes, it was never put into practical use because of the necessity to maintain and screen hundreds of thousands of clones from each size fraction. In addition cross hybridization would be expected to yield a large fraction of false positive clones.

5. Shotgun Cloning

The only practical method for preparing DNA longer than 5 kb for sequencing is subcloning the source DNA as random fragments small enough to be sequenced. The large source DNA molecule is fragmented by sonication or hydrodynamic shearing, fractionated to select the optimum fragment size, and then subcloned into a bacterial plasmid or virus genome. The individual subclones can be subjected to Sanger or other sequencing reactions in order to determine sequences within the source DNA. If many overlapping subclones are sequenced, the entire sequence for the large source DNA can be determined. The advantages of shotgun cloning over the other techniques are: 1) the fragments are small and uniform in size so that they can be cloned with high efficiency independent of sequence; 2) the fragments can be short enough that both strands can be sequenced using the Sanger reaction; 3) transformation and growth of many clones is rapid and inexpensive; and 4) clones are very stable.

E. Genomic Sequencing

Current techniques to sequence genomes (as well as any DNA larger than about 5 kb) depend upon shotgun cloning of small random fragments from the entire DNA. Bacteria and other very small genomes can be directly shotgun cloned and sequenced. This is called "pure shotgun sequencing." Larger genomes are usually first cloned as large pieces and each clone is shotgun sequenced. This is called "directed shotgun sequencing."

1. Pure Shotgun Sequencing

Genomes up to several millions or billions of base pairs in length can be randomly fragmented and subcloned as small fragments. However in the process of fragmentation all information about the relative positions of the fragment sequences in the native genome is lost. However this information can be recovered by sequencing with 5–10-fold redundancy (i.e., the number of bases sequenced in different reactions add up to 5 to 10 times as many bases in the genome) so as to generate sufficiently numerous overlaps between the sequences of different fragments that a computer program can assemble the sequences from the subclones into large contiguous sequences (contigs). However, due to some regions being more difficult to clone than others and due to incomplete statistical sampling, there will still be some regions within the genome that are not sequenced even after highly redundant sequencing. These unknown regions are called "gaps." After assembly of the shotgun sequences into contigs, the sequencing is "finished" by filling in the gaps. Finishing must be done by additional sequencing of the subclones, by primer walking beginning at the edge of a contig, or by sequencing PCR products made using primers from the edges of adjacent contigs.

There are several disadvantages to the pure shotgun strategy: 1) As the size of the region to be sequenced increases, the effort of assembling a contiguous sequence from shotgun reads increases faster than N 1nN, where N is the number of reads; 2) Repetitive DNA and sequencing errors can cause ambiguities in sequence assembly; and 3) Because subclones from the entire genome are sequenced at the same time and significant redundancy of sequencing is necessary to get contigs of moderate size, about 50% of the sequencing has to be finished before the sequence accuracy and the contig sizes are sufficient to get substantial information about the genome. Focusing the sequencing effort on one region is impossible.

2. Directed Shotgun Sequencing

The directed shotgun strategy, adopted by the Human Genome Project, reduces the difficulty of sequence assembly by limiting the analysis to one large clone at a time. This "clone-by-clone" approach requires four steps: 1) large-insert cloning, comprised of a) random fragmentation of the genome into segments 100,000–300,000 bp in size, b) cloning of the large segments, and c) isolation, selection and mapping of the clones; 2) random fragmentation and subcloning of each clone as thousands of short subclones; 3) sequencing random subclones and assembly of the overlapping sequences into contiguous regions; and 4) "finishing" the sequence by filling the gaps between contiguous regions and resolving inaccuracies. The positions of the sequences of the large clones within the genome are determined by the mapping steps, and the positions of the sequences of the subclones are determined by redundant sequencing of the subclones and computer assembly of the sequences of individual large clones. Substantial initial investment of resources and time are required for the first two steps before sequencing begins. This inhibits sequencing DNA from different species or individuals. Sequencing random subclones is highly inefficient, because significant gaps exist until the subclones have been sequenced to about 7× redundancy. Finishing requires "smart" workers and effort equivalent to an additional ~3× sequencing redundancy.

The directed shotgun sequencing method is more likely to finish a large genome than is pure shotgun sequencing. For the human genome, for example, the computer effort for directed shotgun sequencing is more than 20 times less than that required for pure shotgun sequencing.

There is an even greater need to simplify the sequencing and finishing steps of genomic sequencing. In principle this can be done by creating ordered libraries of DNA, giving uniform (rather than random) coverage, which would allow accurate sequencing with only about 3 fold redundancy and eliminate the finishing phase of projects. Current methods to produce ordered libraries are impractical, because they can cover only short regions (~5,000 bp) and are labor-intensive.

F. Resequencing of DNA

The presence of a known DNA sequence or variation of a known sequence can be detected using a variety of techniques that are more rapid and less expensive than de novo sequencing. These "resequencing" techniques are important for health applications, where determination of which allele or alleles are present has prognostic and diagnostic value.

1. Microarray Detection of Specific DNA Sequences

The DNA from an individual human or animal is amplified, usually by PCR, labeled with a detectable tag, and hybridized to spots of DNA with known sequences bound to a surface. If the individual's DNA contains sequences that are complementary to those on one or more spots on the DNA array, the tagged molecules are physically detected. If the individual's amplified DNA is not complementary to the probe DNA in a spot, the tagged molecules are not detected. Microarrays of different design have different sensitivities to the amount of tested DNA and the exact amount of sequence complementarity that is required for a positive result. The advantage of the microarray resequencing technique is that many regions of an individual's DNA can be simultaneously amplified using multiplex PCR, and the mixture of amplified genetic elements hybridized simultaneously to a microarray having thousands of different probe spots, such that variations at many different sites can be simultaneously detected.

One disadvantage to using PCR to amplify the DNA is that only one genetic element can be amplified in each reaction, unless multiplex PCR is employed, in which case only as many as 50–100 loci can be simultaneously amplified. For certain applications, such as SNP (single nucleotide polymorphism) screening it would be advantageous to simultaneously amplify 1,000–100,000 elements and detect the amplified sequences simultaneously. A second disadvantage to PCR is that only a limited number of DNA bases can be amplified from each element (usually <2000 bp). Many applications require resequencing entire genes, which can be up to 200,000 bp in length.

2. Other Methods of Resequencing

Other methods such as mass spectrometry, secondary structure conformation polymorphism, ligation amplification, primer extension, and target-dependent cleavage can be used to detect sequence polymorphisms. All of these methods either require initial amplification of one or more specific genetic elements by PCR or incorporate other forms of amplification that have the same deficiencies of PCR, because they can amplify only a very limited region of the genome at one time.

SUMMARY OF THE INVENTION

A skilled artisan recognizes, based on the teachings provided herein, that deficiencies of existing methods for amplification of unknown DNA adjacent to known sequence can be solved by using nick translate molecule libraries. More particularly, the present invention teaches generating a library of nick translate molecules to amplify and sequence for the purpose of obtaining successive overlapping sequences from a plurality of nick translate molecules.

In an object of the present invention, the primary PENTAmer library, in a specific embodiment, is prepared in vitro from bacterial or human genome using the teachings provided herein.

In another object of the present invention, the primary PENTAmer library generated in vitro from a genome, such as from a bacteria or human, is amplified more than about 1000 times without any significant change in representation of the specific PENTAmer amplicons.

In an additional object of the present invention, a primary PENTAmer library (directly or after amplification), such as from a bacteria or human, is used to amplify a specific PENTAmer or a PENTAmer sub-pool preferably using only one sequence-specific primer, which generates templates that reproducibly produce high quality sequencing data. Typically, the methods described herein allow systematically generating from about 550 to 750 bases of a new sequence located downstream the primer.

In another object of the present invention, a primary eukaryotic (human) PENTAmer library (directly or after amplification) is used to amplify a specific PENTAmer or a PENTAmer sub-pool using two (or more) nested sequence-specific primers.

In an additional object of the present invention, a circularized eukaryotic (human) PENTAmer library is used to amplify a specific PENTAmer or a PENTAmer sub-pool using inverse PCR and two (or more) sequence-specific primers.

The present invention utilizes a library of nick translate molecules as a means to walk along a chromosome. A skilled artisan recognizes that the terms "walk," "walking," "chromosome walking," or "genome walking" are directed to the generation of unknown sequence from a sample nucleic acid, such as a genome, in a sequential manner by starting from a known sequence, in specific embodiments termed herein as a "kernel," sequencing by a first sequencing reaction (called a "read"), and generating a second sequencing read from a region of sequence obtained in the first read. Thus, the two reads will overlap to some extent, and a consecutive series of such reactions results in the preferred walking embodiment of the invention.

A skilled artisan is cognizant that any method to make an amplifiable nick translate molecule for chromosome walking is within the scope of the present invention. A skilled artisan also recognizes that, in a preferred method, the amplifiable nick translate molecule is generated by methods comprising at least fragmenting a DNA sample; attaching an adaptor to one end of the fragmented molecules, such as by covalent attachment, wherein the adaptor comprises a nick; nick translating with a DNA polymerase having $5' \rightarrow 3'$ polymerase activity and $5' \rightarrow 3'$ exonuclease activity; and attaching a second adaptor to the other end of the nick translated product. The nick translate molecule may be amplified by primer sequences for the adaptors. Although the nick is preferably generated by an adaptor comprising more than one oligonucleotide, wherein the oligonucleotide assembly has a nick between them, a skilled artisan recognizes that the nick may be generated by any standard means in the art.

The following definitions are provided to assist in understanding the nature of the invention.

The term "nick translate molecule" as used herein refers to nucleic acid molecules produced by coordinated $5' \rightarrow 3'$ polymerase activity, such as DNA polymerase, and $5' \rightarrow 3'$ exonuclease activity. The two activities can be present within on enzyme molecule (such as DNA polymerase I or Taq DNA polymerase). In a preferred embodiment, they have adaptor sequences at their 5' and 3' termini.

The term "nick translation" as used herein refers to a coupled polymerization/degradation process that is characterized by a coordinated $5' \rightarrow 3'$ DNA polymerase activity and a $5' \rightarrow 3'$ exonuclease activity.

The term "partial cleavage" as used herein refers to the cleavage by an endonuclease of a controlled fraction of the available sites within a DNA template. The extent of partial cleavage can be controlled by, for example, limiting the reaction time, the amount of enzyme, and/or reaction conditions.

In an object of the present invention, there is a method of producing a consecutive overlapping series of nucleic acid sequences from a DNA sample, comprising the steps of generating a first amplifiable nick translation product, wherein said nick translation of said first amplifiable nick translation product initiates from a known nucleic acid sequence in the DNA sample; determining at least a partial sequence from said first nick translation product; and generating at least a second amplifiable nick translation product, wherein said nick translation of said second amplifiable nick translation product initiates from the partial sequence of said first nick translation product.

In another object of the present invention there is a method of producing a library of consecutive overlapping series of nucleic acid sequences from a DNA sample comprising DNA molecules having a region comprising a known nucleic acid sequence, the method comprising the steps of digesting DNA molecules of the DNA sample with a first sequence-specific endonuclease to generate a plurality of DNA fragments; generating a first amplifiable nick translation product, wherein said nick translation of said first amplifiable nick translation product initiates from the known nucleic acid sequence; determining at least a partial sequence from said first nick translation product; and generating one or more additional amplifiable nick translation products, wherein said nick translation of said one or more amplifiable nick translation products initiates from the partial sequence of a previous nick translation product. In a specific embodiment, the method further comprises the step of digesting DNA molecules with at least a second sequence-specific endonuclease, wherein the preceding overlapping nick translation product is generated from a DNA fragment from digestion with the first sequence-specific endonuclease or from digestion with the second sequence-specific endonuclease.

In an additional embodiment of the present invention, there is a method of producing a library of consecutive overlapping series of nucleic acid sequences, comprising the steps of obtaining a DNA sample comprising DNA molecules having a region comprising a known nucleic acid sequence; partially cleaving the DNA molecules with a sequence-specific endonuclease to generate a plurality of DNA ends; separating the cleaved DNA molecules; generating a first amplifiable nick translation product, wherein said nick translation of said first amplifiable nick translation product initiates from a known nucleic acid sequence; determining at least a partial sequence from said first nick translation product; and generating one or more amplifiable nick translation products, wherein said nick translation of said one or more amplifiable nick translation products initiates from the partial sequence of a previous nick translation product. In a specific embodiment, the separation of the cleaved DNA molecules is according to size. In another specific embodiment, the size separation is by gel size fractionation. In an additional specific embodiment, the nick translation products are amplified.

In another specific embodiment, the amplification of the nick translation product comprises polymerase chain reaction utilizing a first primer specific to a known sequence in the nick translation product and a second primer specific to an adaptor sequence of the nick translation product. In an additional specific embodiment, at least one of the nick translation products is selectively amplified from the plurality of nick translation products. In a further specific embodiment, the nick translation product is single stranded. In an additional specific embodiment, the partial cleavage of the DNA molecules comprises cleaving for a selected time with a frequently cutting sequence-specific endonuclease, wherein the sequence-specificity of the endonuclease is to three or four nucleotide bases.

In another specific embodiment, the partial cleavage of the DNA molecules comprises subjecting the DNA molecules to a methylase prior to subjection to a methylation-sensitive sequence-specific endonuclease. In a further specific embodiment, the selective amplification comprises introducing to said plurality of nick translation products a plurality of primers, wherein the primers comprise nucleotide base sequence complementary to an adaptor sequence in the nick translation product; an additional variable 3' terminal nucleotide; and a label; hybridizing the primers to their complementary nucleic acid sequences in the adaptor to form a mixture of primer/nick translate molecule hybrids; and extending from a primer having the 3' terminal nucleotide complementary to the nucleotide in the nick translate molecule immediately adjacent to the adaptor sequence, wherein the hybridizing and extending steps form a mixture of unextended primer/nick translate molecule hybrids and extended primer molecule/nick translate molecule hybrids.

In a specific embodiment, the method further comprises binding of the mixture by the label to a support; washing the support-bound mixture to remove the nick translate molecules; removing the support-bound extended molecule from the support. In an additional specific embodiment, the primer further comprises two or more variable 3' terminal nucleotides. In another specific embodiment, the method further comprises separating the nick translate molecules by size. In an additional specific embodiment, the size separation is by gel fractionation. In another specific embodiment, the method further comprises a step of subjecting the size-separated nick translate molecules to an additional amplification step. In a specific embodiment, the selective amplification step is by suppression PCR. In an additional specific embodiment, the suppression PCR utilizes a primer comprising a nucleic acid sequence for a primer specific for an adaptor sequence of the nick translate molecule; and nucleic acid sequence complementary to a region in a plurality of nick translate molecules, whereby the nucleic acid sequence is 5' to the sequence for a primer specific for an adaptor sequence of the nick translate molecule.

In an object of the present invention, in the method the at least one nick translate molecule is amplified by primer extension/ligation reactions. In a further specific embodiment, the method further comprises immobilization of the nick translation molecules onto a solid support. In a specific embodiment, the solid support is a magnetic bead. In another specific embodiment, the primer extension/ligation reactions comprise initiating and extending the primer extension reaction with a first primer which is complementary to sequence in a subset of the plurality of nick translate molecules, wherein the complementary sequence of the nick translate molecule is adjacent to a first adaptor end of the nick translate molecule; and ligating an oligonucleotide to the 5' end of the extension product, wherein the oligonucleotide comprises sequence complementary to the first adaptor of the nick translate molecule and also comprises a sequence for binding by a second primer, wherein the second primer binding sequence in the oligonucleotide is 5' to the first adaptor complementary sequence in the oligonucleotide. In a further specific embodiment, the method further comprise amplifying the primer extended molecule. In another specific embodiment, the method further comprises separating the primer extended molecule from the plurality of nick translate molecule.

In an additional specific embodiment, the nick translate molecules were generated in the presence of dU nucleotides, the primer extended molecule contains no dU nucleotides, and wherein the separating step comprises degradation of the plurality of nick translate molecules by dU-glycosylase. In another specific embodiment, the amplification step comprises polymerase chain reaction using the second primer and a primer complementary to a second adaptor of the nick translate molecule. In a further specific embodiment, the ligation/primer extension reactions comprise ligating in a head-to-tail orientation a plurality of oligonucleotides to form an oligonucleotide assembly, wherein the oligonucleotides are complementary to nick translate molecule sequence adjacent to a first adaptor end of the nick translate molecule and wherein the nick translate molecule sequence is present in a subset of the plurality of nick translate molecules, wherein the nick translation molecule has the first adaptor on one terminal end and a second adaptor on the other terminal end; initiating and extending the primer extension reaction with the 3' end of the oligonucleotide assembly; and ligating an oligonucleotide to the 5' end of the extension product, wherein the oligonucleotide comprises sequence complementary to the first adaptor of the nick translate molecule and also comprises sequence for binding by a first primer, wherein the first primer binding sequence is 5' to the first adaptor complementary sequence in the oligonucleotide.

In another specific embodiment, the method further comprises the steps of separating the primer extended molecule from the plurality of nick translate molecules; and amplifying the primer extended molecule. In an additional specific embodiment, the nick translate molecules were generated in the presence of dU nucleotides, the primer extended molecule contains no dU nucleotides, and wherein the separating step comprises degradation of the plurality of nick translate molecules by dU-glycosylase. In another specific embodiment, the amplification step comprises polymerase chain reaction using the first primer and a second primer complementary to the second adaptor of the nick translate molecule. In an additional specific embodiment, the primer extension/ligation reaction comprises initiating and extending the primer extension reaction with a first primer which is complementary to sequence in a subset of the plurality of nick translate molecules, wherein the nick translate molecule sequence is adjacent to a first adaptor end of the nick translate molecule; and ligating an oligonucleotide to the 5' end of the extension product, wherein the oligonucleotide comprises sequence complementary to the first adaptor of the nick translate molecule; sequence for binding by a second primer, wherein the second primer binding sequence is 5' to the sequence in (1); and a label at the 5' end.

In an additional specific embodiment, the method further comprises the steps of separating the primer extended molecule from the plurality of nick translate molecules by the label of the oligonucleotide; and amplifying the primer extended molecule.

In a specific embodiment, the label is biotin. In another specific embodiment, the separation further comprises streptavidin-coated magnetic beads. In a further specific embodiment, the amplification step comprises polymerase chain reaction using the second primer and a third primer complementary to a second adaptor of the nick translate molecule.

In an additional object of the present invention there is a method of sequencing nucleic acid, comprising the steps of obtaining a DNA sample comprising DNA molecules having a region comprising a known nucleic acid sequence; partially cleaving the DNA molecules with a sequence-specific endonuclease to generate a plurality of DNA ends; separating the cleaved DNA molecules; generating a first amplifiable nick translation product, wherein the first amplifiable nick translation product comprises an adaptor at each end, wherein the nick translation of said first amplifiable nick translation product initiates from a known nucleic acid sequence; determining at least a partial sequence from said first nick translation product; and generating one or more additional amplifiable nick translation products, wherein said nick translation of said one or more additional amplifiable nick translation products initiates from the partial sequence of a previous nick translation product; and sequencing the nick translation products, wherein the amplified nick translation product is not subjected to cloning prior to the sequencing reaction. In a specific embodiment, the DNA sample is a genome. In another specific embodiment, there is a limited amount of DNA sample. In an additional specific embodiment, the amplification is by polymerase chain reaction, and one of the primers for the polymerase chain reaction is used as a primer for the sequencing reaction. In a further specific embodiment, at least a portion of the adaptor sequence is removed from the amplified nick translation molecule. In another specific embodiment, the removal step comprises subjecting the amplified nick translation molecule to a 5' exonuclease. In an additional specific embodiment, a region of the adaptor sequence of the nick translate molecule comprises a dU nucleotide and the removal comprises degradation by dU-glycosylase. In a further specific embodiment, a region of the adaptor sequence comprises a ribonucleotide and the removal comprises degradation by alkaline hydrolysis. In an another specific embodiment, the region of the second adaptor sequence is in a 3' region of the second adaptor sequence.

In an additional object of the present invention, there is a method of providing sequence for a gap in a genome sequence, comprising the steps of obtaining a DNA sample of the genome comprising DNA molecules having a region comprising a known nucleic acid sequence adjacent to the gap; digesting the DNA molecules with a plurality of sequence-specific endonucleases to generate a plurality of DNA ends; generating a first amplifiable nick translation product, wherein said nick translation of said first amplifiable nick translation product initiates from the known nucleic acid sequence; determining at least a partial sequence from said first nick translation product; and generating one or more additional amplifiable nick translation products, wherein said nick translation of said one or more amplifiable nick translation products initiates from the partial sequence of a previous nick translation product, wherein at least one of the amplifiable nick translation products comprises sequence of the gap. In a specific embodiment, the genome is a bacterial genome. In a specific embodiment, the genome is a plant genome. In a specific embodiment, the genome is an animal genome. In a specific embodiment, the animal genome is a human genome. In an additional specific embodiment, the bacteria are unculturable. In an additional specific embodiment, the bacteria is present in a plurality of bacteria.

In an additional object of the present invention, there is a method of producing a library of consecutive overlapping series of nucleic acid sequences from a DNA sample, comprising the steps of obtaining the DNA sample comprising a DNA molecule; digesting the DNA molecule with a first sequence-specific endonuclease to generate a plurality of DNA fragments, wherein at least one DNA fragment has a region comprising a known nucleic acid sequence; attaching a first adaptor molecule to ends of the DNA fragments to provide a nick translation initiation site, wherein the first adaptor comprises a label; subjecting the first adaptor-bound DNA fragment to nick translation comprising DNA polymerization and 5'–3' exonuclease activity, wherein the nick translation initiates from the known nucleic acid sequence, to generate a first nick translation product; isolating the nick translation product by the label; attaching a second adaptor molecule to the first nick translate product; determining at least a partial sequence from the first nick translation product; and generating one or more additional amplifiable nick translation products, wherein said nick translation of said one or more amplifiable nick translation products initiates from the partial sequence of a previous nick translation product. In a specific embodiment, the label is biotin and the isolation step is binding to streptavidin-coated magnetic beads.

In another object of the present invention, there is a method of producing a library of consecutive overlapping series of nucleic acid sequences, comprising the steps of obtaining a DNA sample comprising DNA molecules having a region comprising a known nucleic acid sequence; partially cleaving the DNA molecules with a sequence-specific endonuclease to generate a plurality of DNA fragments, wherein at least one DNA fragment has a region comprising a known nucleic acid sequence; separating the cleaved DNA fragments; attaching a first adaptor molecule to ends of the DNA fragments to provide a nick translation initiation site, wherein the first adaptor comprises a label; subjecting the first adaptor-bound DNA fragment to nick translation comprising DNA polymerization and 5'–3' exonuclease activity, wherein the nick translation initiates from the known nucleic acid sequence, to generate a first nick translation product; isolating the nick translation product by the label; attaching a second adaptor molecule to the first nick translate products; determining at least a partial sequence from said first nick translation product; and generating one or more additional amplifiable nick translation products, wherein said nick translation of said one or more amplifiable nick translation products initiates from the partial sequence of said first nick translation product. In a specific embodiment, the separation of the DNA fragments is by size. In another specific embodiment, the size separation is by electrophoresis.

In another object of the present invention, there is a library of consecutive overlapping series of nucleic acid sequences from a DNA sample, wherein the library is generated by the methods described herein.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 14A and 14B demonstrates targeted PENTAmer amplification by modular oligonucleotide assembly-Method II.

Figure 1:
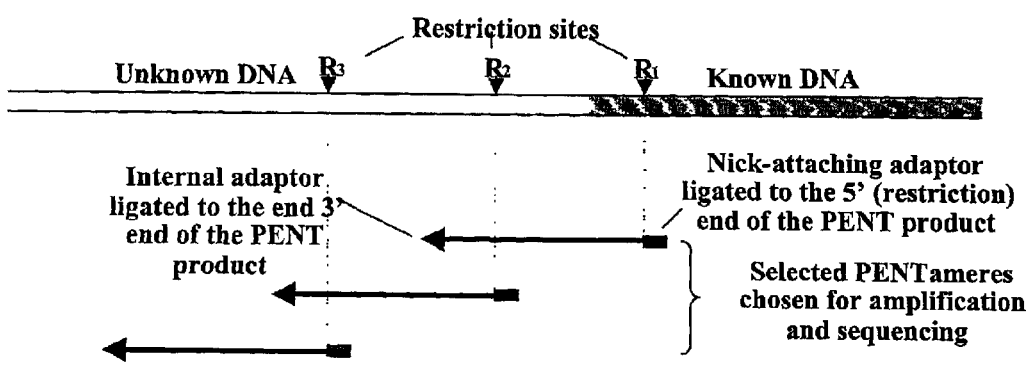
FIG. 1 illustrates genome walking by sequential amplification of the overlapping PENTAmers.

Other objects, features and advantages of the present invention will become apparent from the following detailed description. It should be understood, however, that the detailed description and the specific examples, while indicating preferred embodiments of the invention, are given by way of illustration only, since various changes and modifi-

DETAILED DESCRIPTION OF THE INVENTION

This application herein incorporates by reference in its entirety U.S. application Ser. No. 09/860,738 filed May 18, 2001.

As used herein the specification, "a" or "an" may mean one or more. As used herein in the claim(s), when used in conjunction with the word "comprising", the words "a" or "an" may mean one or more than one. As used herein "another" may mean at least a second or more. As used herein, the term "nick translate molecule" is used interchangeably with the terms "PENTAmer" or "nick translate product."

I. Generation of a Nick Translate Molecule

The present invention is directed to chromosome walking through the generation of nick translate molecules, and a skilled artisan recognizes that the nick translate molecules may be generated by any standard means in the art. However, in a preferred embodiment, the nick translate molecules are adaptor attached nick translate molecules (designated a PENTAmer).

The method for creating an adaptor attached nick translate molecule provides a powerful tool useful in overcoming many of the difficulties currently faced in large scale DNA manipulation, particularly genomic sequencing.

A. Primary PENTAmer

In the simplest implementation, a primary PENTAmer is generated by:

1) Ligating a nick-translation first adaptor to the proximal end of the source DNA (the template);
2) Initiating a nick translation reaction at the nick site of said adaptor using a DNA polymerase having 5'→-3' exonuclease activity;
3) Elongating the PENT product a specific time; and
4) Appending a nick-ligation second adaptor to the distal, 3' end of the PENT product to form a PENTAmer-template hybrid ("nascent PENTAmer").

While this basic technique sets forth the primary methodology envisioned by the inventors to create a PENTAmer product, it would be clear to one of ordinary skill that changes could be made in order to achieve an analogous outcome.

In a specific embodiment, the PENT reaction is initiated, continued, and terminated on a largely double-stranded template, which gives the PENTAmer amplification important advantages for creating DNA for sequence analysis. An advantage of using PENTAmers to amplify different regions of the template is the fact that in most applications PENTAmers having different internal sequences have the same terminal sequences. These advantages are important for creating PENTAmers that are most useful as intermediates for in vitro or in vivo amplification. Amplification of these intermediates is more useful than direct amplification of DNA by cloning or PCR.

During later steps, the PENTAmers can be degraded by incorporating distinguishable nucleotides during the reaction. For example, incorporation of dU nucleotides and subsequent exposure to dU-glycosylase allows destruction of the PENTAmers for separation from, for example, a desired nucleic molecule lacking the dU nucleotides.

The initiation site for a PENT reaction (as distinct from an oligonucleotide primer) can be introduced by any method that results in a free 3' OH group on one side of a nick or gap in otherwise double-stranded DNA, including, but not limited to such groups introduced by: a) digestion by a restriction enzyme under conditions that only one strand of the double-stranded DNA template is hydrolyzed; b) random nicking by a chemical agent or an endonuclease such as DNAase I; c) nicking by f1 gene product II or homologous enzymes from other filamentous bacteriophage (Meyer and Geider, 1979); and/or d) chemical nicking of the template directed by triple-helix formation (Grant and Dervan, 1996).

However, for PENTAmer synthesis, the primary means of initiation is through the ligation of an oligonucleotide primer onto the target nucleic acid. This very powerful and general method to introduce an initiation site for strand replacement synthesis employs a panel of special double-stranded oligonucleotide adaptors designed specifically to be ligated to the termini produced by restriction enzymes. Each of these adaptors is designed such that the 3' end of the restriction fragment to be sequenced can be covalently joined (ligated) to the adaptor, but the 5' end cannot. Thus the 3' end of the adaptor remains as a free 3' OH at a 1 nucleotide gap in the DNA, which can serve as an initiation site for the strand-replacement sequencing of the restriction fragment. Because the number of different 3' and 5' overhanging sequences that can be produced by all restriction enzymes is finite, and the design of each adaptor will follow the same simple strategy, above, the design of every one of the possible adaptors can be foreseen, even for restriction enzymes that have not yet been identified. To facilitate sequencing, a set of such adaptors for strand replacement initiation can be synthesized with labels (radioactive, fluorescent, or chemical) and incorporated into the dideoxyribonucleotide-terminated strands to facilitate the detection of the bands on sequencing gels.

More specifically, adaptors with 5' and 3' extensions can be used in combination with restriction enzymes generating 2-base, 3-base and 4-base (or more) overhangs. The sense strand of the adaptor has a 5' phosphate group that can be efficiently ligated to the restriction fragment to be sequenced. The anti-sense strand (bottom, underlined) is not phosphorylated at the 5' end and is missing one base at the 3' end, effectively preventing ligation between adaptors. This gap does not interfere with the covalent joining of the sense strand to the restriction fragment, and leaves a free 3' OH site in the anti-sense strand for initiation of strand replacement synthesis.

Polymerization may be terminated specific distances from the priming site by inhibiting the polymerase a specific time after initiation. For example, under specific conditions Taq DNA polymerase is capable of strand replacement at the rate of 250 bases/min, so that arrest of the polymerase after 10 min occurs about 2500 bases from the initiation site. This strategy allows for pieces of DNA to be isolated from different locations in the genome.

PENT reactions may also be terminated by incorporation of a dideoxyribonucleotide instead of the homologous naturally-occurring nucleotide. This terminates growth of the new DNA strand at one of the positions that was formerly occupied by dA, dT, dG, or dC by incorporating ddA, ddT, ddG, or ddC. In principle, the reaction can be terminated using any suitable nucleotide analogs that prevent continuation of DNA synthesis at that site.

B. Secondary PENTAmers

Secondary PENTAmers are created by two nick-translation reactions. The length of the first PENT reaction determines the distance of one end of the secondary PENTAmer from the initiation position, whereas the second (shorter) PENT reaction determines the length of the secondary PENTAmer. The advantage of secondary PENTAmers is that the position of the PENTAmer within the template DNA and the length of the PENTAmer are independently controlled.

There are two methods to synthesize a secondary PENTAmer. In the first method, a secondary PENTAmer is created and amplified by:

Ligating a first terminus-attaching, nick translation adaptor to the proximal end of the template DNA molecule;

Initiating a first PENT reaction at the proximal end of the source DNA molecule using a first adaptor;

Elongating the first PENT product a specified time;

Appending a second nick-attaching adaptor to the distal, 3' end of the first PENT product;

Initiating a second PENT reaction at the same proximal end of the source DNA molecule using the first adaptor;

Elongating the second PENT product a specifided time;

Appending a third nick-attaching adaptor to the 5' end of the degraded first PENT product;

(Optionally) separating the single-stranded secondary PENTAmer of length from the template (e.g., by denaturation);

In a second method, a secondary PENTAmer is created by:

Ligating a first terminus-attaching, nick translation adaptor to the proximal end of the template DNA molecule;

Initiating a first PENT reaction at the proximal end of the source DNA molecule using the first adaptor;

Elongating the PENT product a specified time;

Appending a second nick-attaching adaptor to the distal, 3' end of the PENT product;

Separating the single-stranded primary PENTAmer from the template;

Replicating the second strand of the primary PENTAmer using primer extension;

Initiating a second PENT reaction at the upstream end of the secondary PENTAmer;

Elongating the secondary PENT product a specified time;

Appending a third nick-attaching adaptor to the 3' end of the secondary PENT product; and (Optionally) separating the single-stranded secondary PENTAmer from the template.

C. Recombinant PENTAmers

The difficulty of immobilizing very large DNA fragments may be overcome by bringing together sequences from both the proximal and distal ends of long templates to create a recombinant PENTAmer.

A recombinant PENTAmer is made on a single template molecule, having different structures at the left (proximal) and right (distal) ends.

1) The first end of a recombination adaptor RA is attached to the left, proximal end of the template;

2) The second end of a recombination adaptor RA is attached to the right, distal end, to form a circular molecule; and 3) The initiation domain of adaptor RA is used to synthesize a PENTAmer containing the distal template sequences.

PENTAmers will only be created on those fragments that have been ligated to both ends of the recombination adaptor RA. Specific designs and use of recombination adaptors would be apparent to a skilled artisan. One embodiment uses an adaptor RA comprising a first ligation domain complementary to the proximal terminus of the template, an activatable second ligation domain complementary to the distal terminus, and a nick-translation initiation domain capable of translating the nick from the distal end toward the center of the template. In the case of a recombination adaptor of that specific design, the template would be made resistant to cleavage by the activation restriction enzyme by methylation at the restriction recognition sites, and the second step would be executed in the following way: 1) removal of unligated adaptor RA from solution, 2) activation of adaptor RA by restriction digestion of the unmethylated site within the adaptor, 3) dilution of the template, 4) ligation of the second ligation domain to the distal end of the template, and 5) concentration of the circularized molecules. Step 3 is executed by the same methods used to create a primary PENTAmer, however the nick-translation initiates at the initiation domain of an RA adaptor.

The PENTAmer formed can be amplified by any of the methods described earlier, e.g., by PCR using primers complementary to sequences in adaptors.

D. Adaptors

A preferred design of a nick-translation adaptor is formed by annealing 3 oligonucleotides (or more): oligonucleotide 1, oligonucleotide 2 and oligonucleotide 3. The left ends of these adaptors are designed to be ligated to double-stranded ends of template DNA molecules and used to initiate nick-translation reactions. Oligonucleotide 1 has a phosphate group (P) at the 5' end and a blocking nucleotide at the 3' end, a non-specified nucleotide composition and length from about 10 to 200 bases. Oligonucleotide 2 has a blocked 3' end, a non-phosphorylated 5' end, a nucleotide sequence complementary to the 5' part of oligonucleotide 1 and length from about 5 to 195 bases. When hybridized together, oligonucleotides 1 and 2 form a double-stranded end designed to be ligated to the 3' strand at the end of a template molecule. To be compatible with a ligation reaction to the end of a DNA restriction fragment, a nick-translation adaptor can have blunt, 5'-protruding or 3'-protruding end. Oligonucleotide 3 has a 3' hydroxyl group, a non-phosphorylated 5' end, a nucleotide sequence complementary to the 3' part of oligonucleotide 1, and length from about 5 to 195 bases. When hybridized to oligonucleotide 1, oligonucleotides 2 and 3 form a nick or a few base gap within the lower strand of the adaptor. Oligonucleotide 3 can serve as a primer for initiation of the nick-translation reaction.

Other nick-attaching adaptors are partially double-stranded or completely single-stranded short DNA molecules that can be covalently linked to the 3' hydroxyl group of the nick-translation DNA product. Nick-translation DNA product can be a single-stranded molecule isolated from its DNA template or the nick-translation product still hybridized to the template DNA. The nick-attaching adaptors are designed to complete the synthesis of the 3' end of PENTAmers.

II. Chromosome Walking Using Primary PENTAmer Library-General Embodiments

PENTAmer walking is achieved by priming-selection and amplification of a limited number of PENTAmer molecules with a known sequence at their 5' end (FIG. 1). At every step a new DNA sequence located downstream from the primer (s) is generated. In a preferred embodiment, the predicted size of the amplicon guarantees the success of each walking step; that is, the amount of sequence information generated at each step is equal to the PENTAmer amplicon size (for example, 1 kb). In practice, the new sequence identified at each walking step is limited by existing DNA sequencing technology and usually does not exceed about 750 bp. To guarantee the success of the proposed walking strategy, the nick-translate library should be redundant to the extent that at each step the 5' end of the nick-translate molecule can be identified, the molecule primed, amplified and sequenced. In principle, one library and one amplification is necessary at each step.

Figure 2:
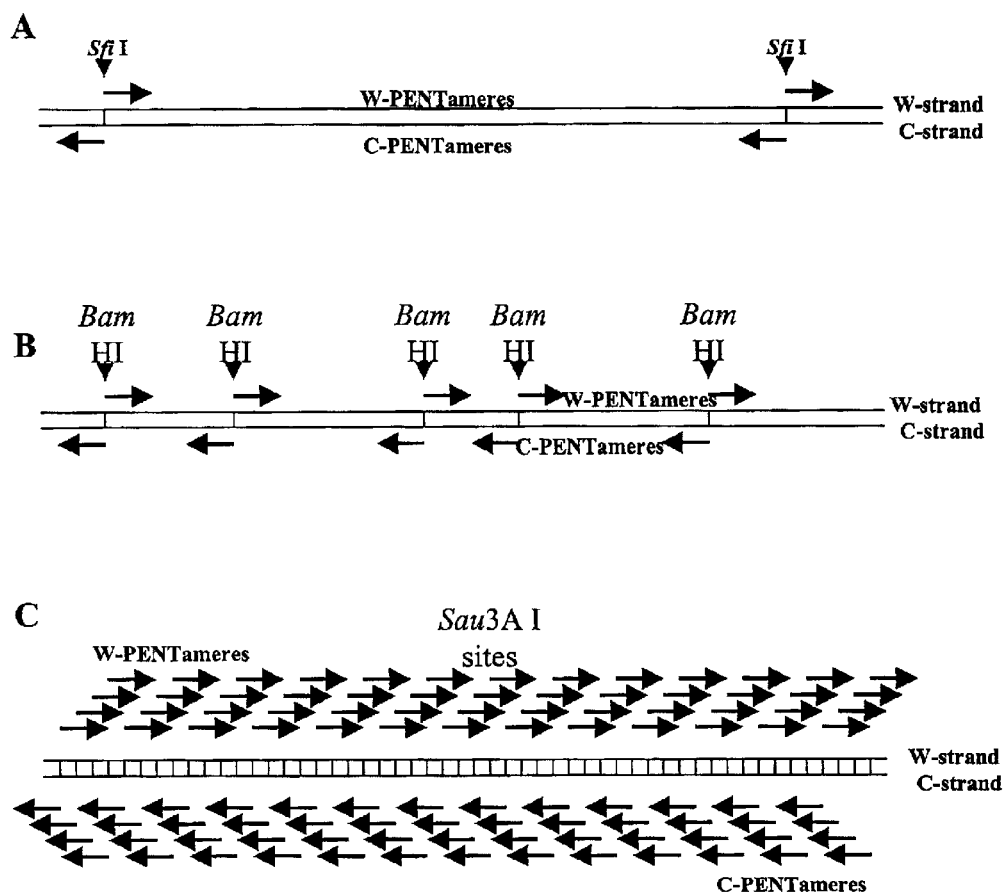
FIG. 2 demonstrates types of PENTAmer libraries.

Depending on frequency of DNA cleavage with a restriction enzyme, the corresponding primary PENTAmer library would result in a different level of coverage of genomic DNA. For example, the PENTAmer library prepared from DNA fragments after Sfi I and BamH I digestion will have an average of about two PENTAmer molecules per 60 kb and 10 kb, respectively (FIGS. 2A and 2B) leaving substantial gaps between consecutive PENTAmer molecules (PENTAmers generated at both strands of DNA are herein considered separately: C- and W-PENTAmers). The PENTAmer library prepared after partial restriction digestion of DNA with a frequently cutting endonuclease Sau3A I will have an average 8 molecules per 1 Kb. At the size of the PENTAmer amplicon of 1 Kb, the levels of redundancy for those cases A, B and C shown on FIG. 2 are 0.03, 0.2 and 8, respectively.

Figure 3A:
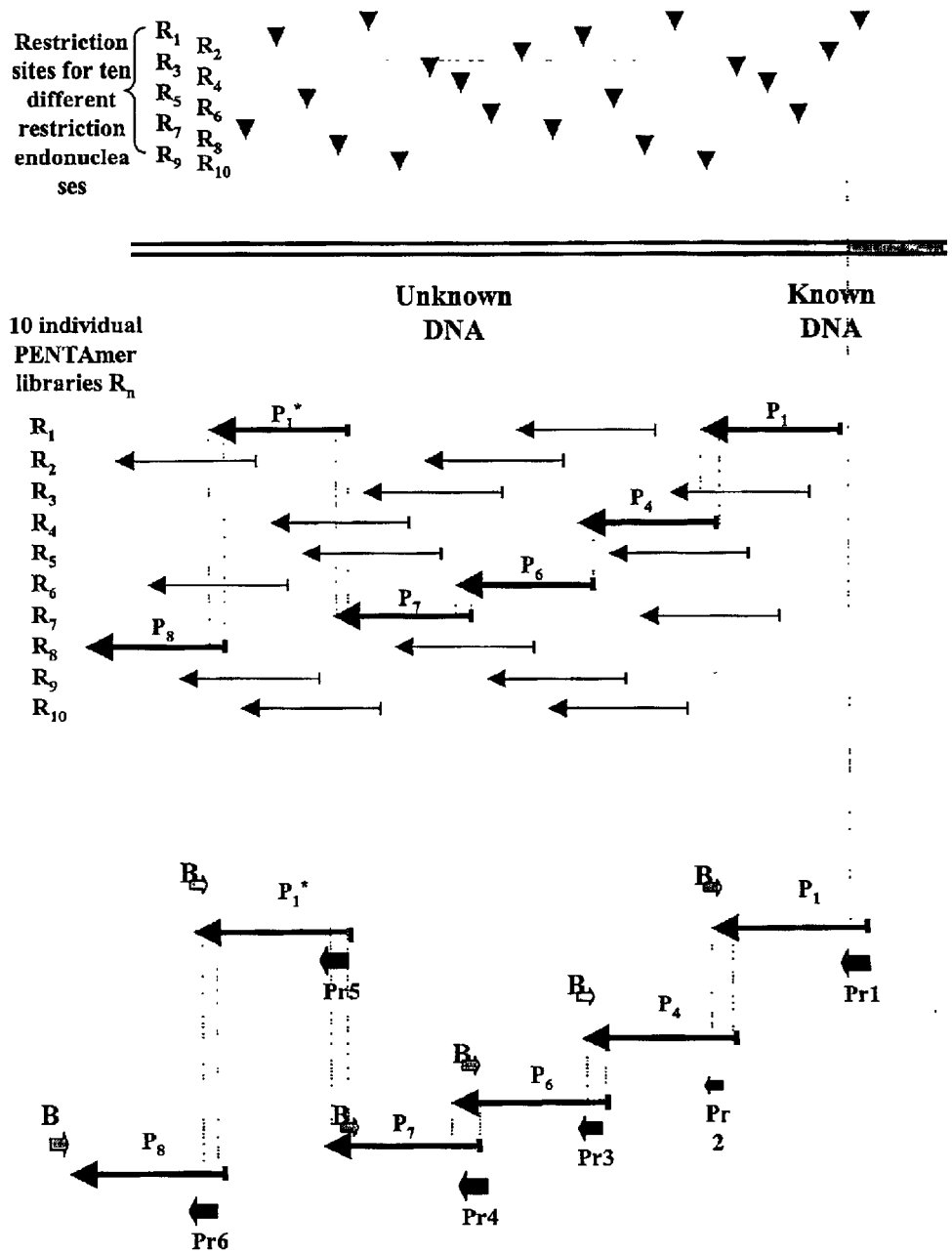
FIGS. 3A and 3B illustrate the general strategy of genome walking by a targeted amplification of the overlapping PENTAmers.

A. Genome Walking by Amplification of PENTAmers from Libraries Prepared by Complete Digestion with Several Different Restriction Endonucleases In this approach, several (N) nick-translate (PENTAmer) sub-libraries are produced from DNA obtained by a complete digestion with N different non-frequently cutting restriction enzymes $R_1$–$R_n$ (FIG. 3A). Because there is no overlap between PENTAmers within one sub-library, the redundancy of total coverage is achieved by preparing PENTAmer sub-libraries from several DNA restriction digests.

Figure 4A:
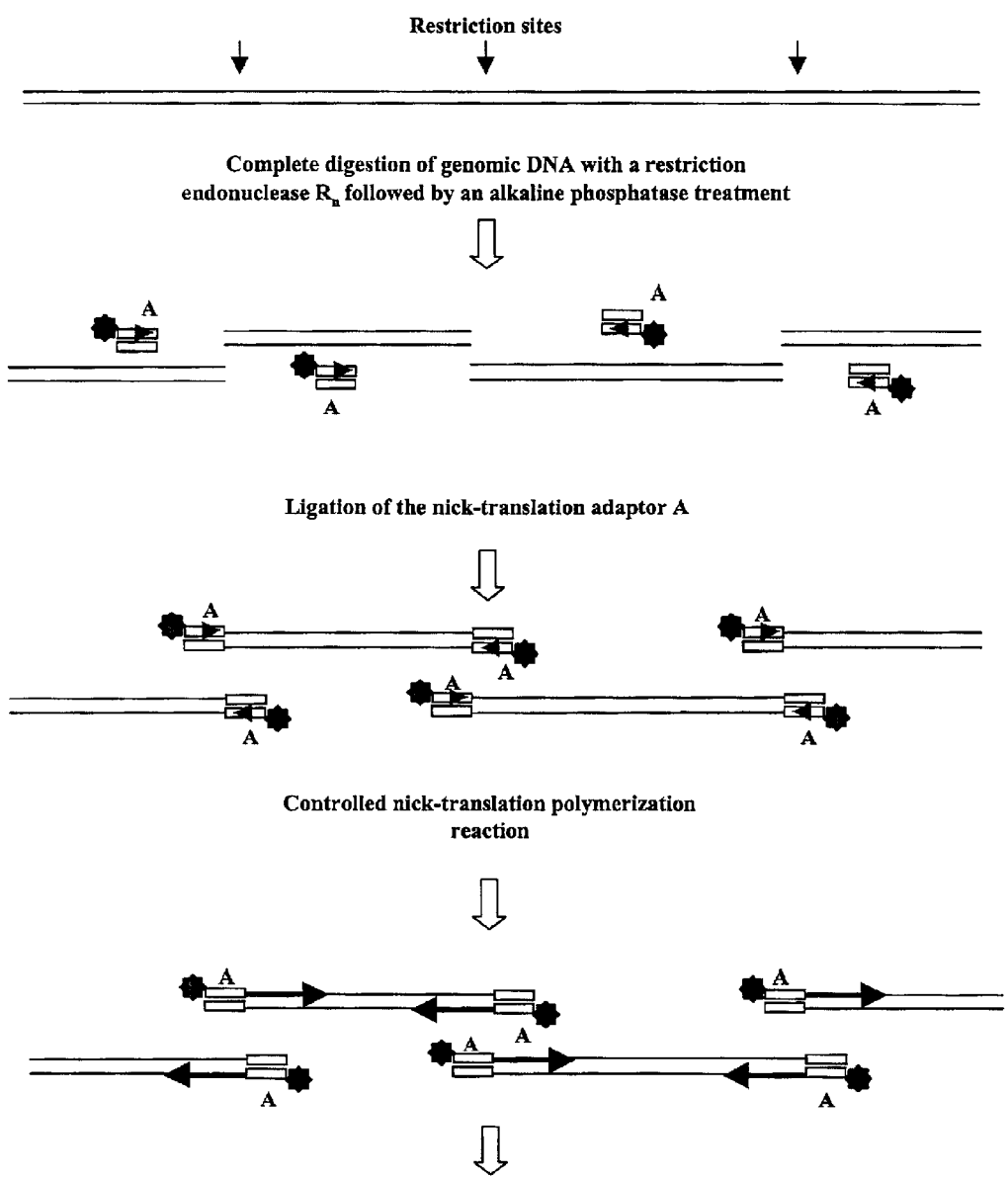
FIGS. 4A and 4B illustrate synthesis of the primary PENTAmer library from a genomic DNA completely digested with a restriction endonuclease.
Figure 4B:
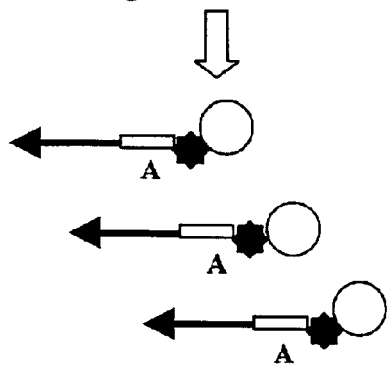
Figure 4B:
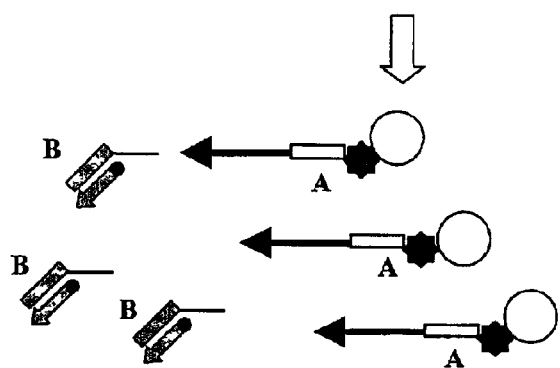
Figure 4B:
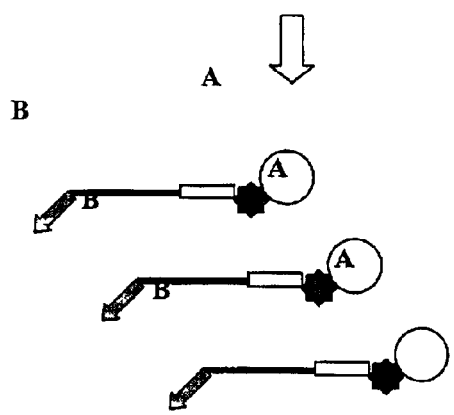

FIGS. 4A and 4B illustrate the preparation of the primary PENTAmer library for a given restriction enzyme $R_n$ presented in the following Protocol 1:

1. Protocol 1: Preparation of the Primary PENTAmer Libraries by a Complete Digestion with Different Restriction Enzymes c. Split DNA into N tubes containing N different restriction enzymes and corresponding buffer, and digest to completion. The most suitable enzymes are the restriction endonucleases with 6-base specificity as, for example, BamH I, EcoR I, Hind III, etc. A skilled artisan is aware that there are more than 100 enzymes of this type currently available on the market. Stop the reaction by adding EDTA or/and by heating at 65–75° C.

d. Incubate DNA samples with the alkaline phosphatase for an appropriate time to remove the phosphate group from all 5' DNA restriction fragments (this step is optional). Purify DNA by phenol/chlorophorm extraction-ethanol precipitation or using commercially available DNA purification kits.

e. Ligate the nick-translation adaptor A to all DNA ends. Purify DNA.

f. Incubate with a DNA polymerase possessing 5' exonuclease activity (for example, non-mutated Taq DNA polymerase) for a specific time to synthesize DNA molecules of a controlled size (PENT products).

g. Isolate PENT molecules by capturing on the streptavidin-coated magnetic beads.

h. Ligate the second adaptor B to the 3' ends of immobilized PENT molecules.

At this point, N different primary PENTAmer sub-libraries are generated. The sub-libraries can be additionally amplified if necessary using universal primers A and B.

FIG. 3A illustrates the case when 10 individual PENTAmer libraries constitute a walking nick-translate DNA library. The figure shows a DNA region covered by 21 PENTAmer amplicons originated from the bottom C-strand of DNA. The walking process starts at the right end where the DNA sequence is known. The selection of the specific PENTAmer molecule $P_n$ is achieved in the two steps: first, when choosing the corresponding sub-library $R_n$ for the amplification; and second, when amplifying the DNA fragment using sequence-specific primer Pr(n) and universal adaptor-specific primer B. Because there is no overlap between PENTAmers within one sub-library the exact location of the sequence-specific primer is not important except that it should anneal to DNA downstream the restriction site.

For example, amplification and sequencing of the molecule $P_1$ using sub-library $R_1$ and primers Pr 1 and B is resulted in identification of the restriction site $R_4$ within the 3' end of the same molecule. At the next step, individual sub-library $R_4$ and primers Pr 2 and B are used to amplify and sequence the molecule $P_4$. The restriction site $R_6$ is identified at the 3' end of the $P_4$ DNA molecule and the $P_6$ molecule is amplified and sequenced using library $R_6$ and primers Pr 3 and B. As a result, a minimal tiling path is created by the sequential amplification and sequencing of the molecules $P_1$, $P_4$, $P_6$, $P_7$, $P_1^*$, and $P_8$ from the corresponding nick-translate sub-libraries $R_1$, $R_4$, $R_6$, $R_7$, $R_1$, and $R_8$.

Figure 3B:
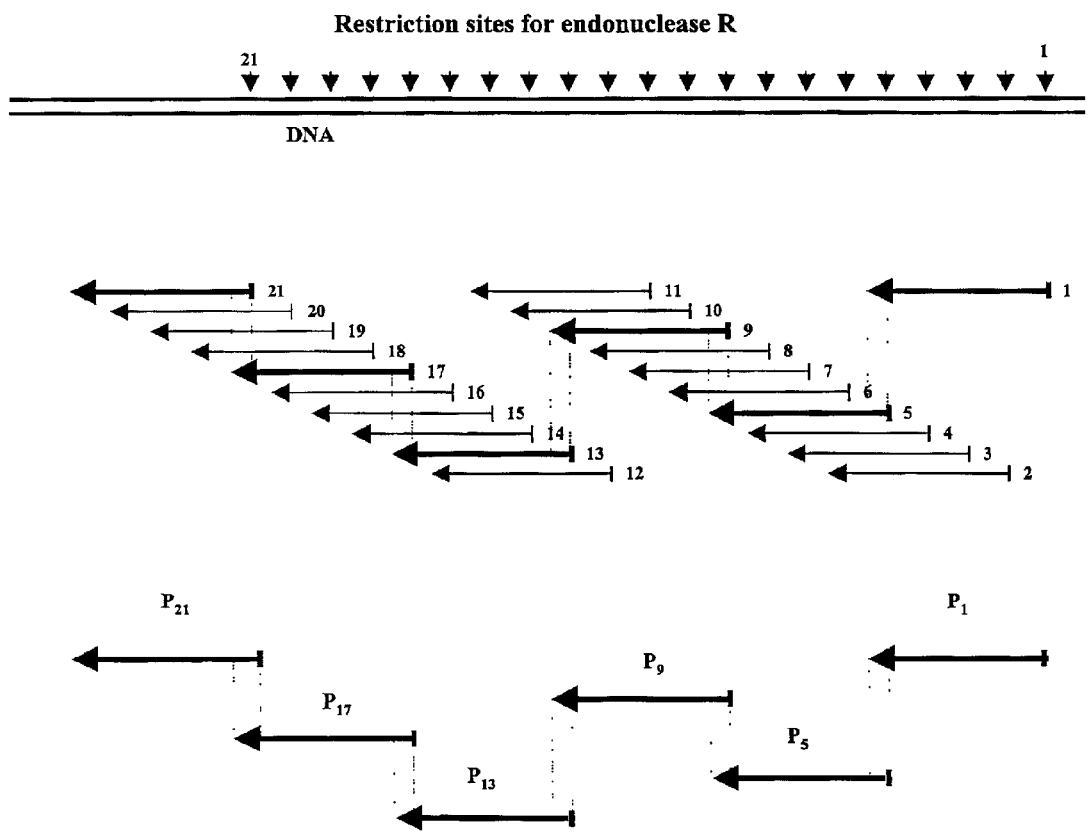

B. Genome Walking by Amplification of PENTAmers from Libraries Prepared by Partial Digestion with One Frequently Cutting Restriction Endonuclease In this case, a redundant nick-translate DNA library is prepared by a partial digestion of DNA with one frequently cutting restriction endonuclease R (FIG. 3B). The drawing shows 21 nick-translate molecules originated from the bottom C-DNA strand.

Figure 5A:
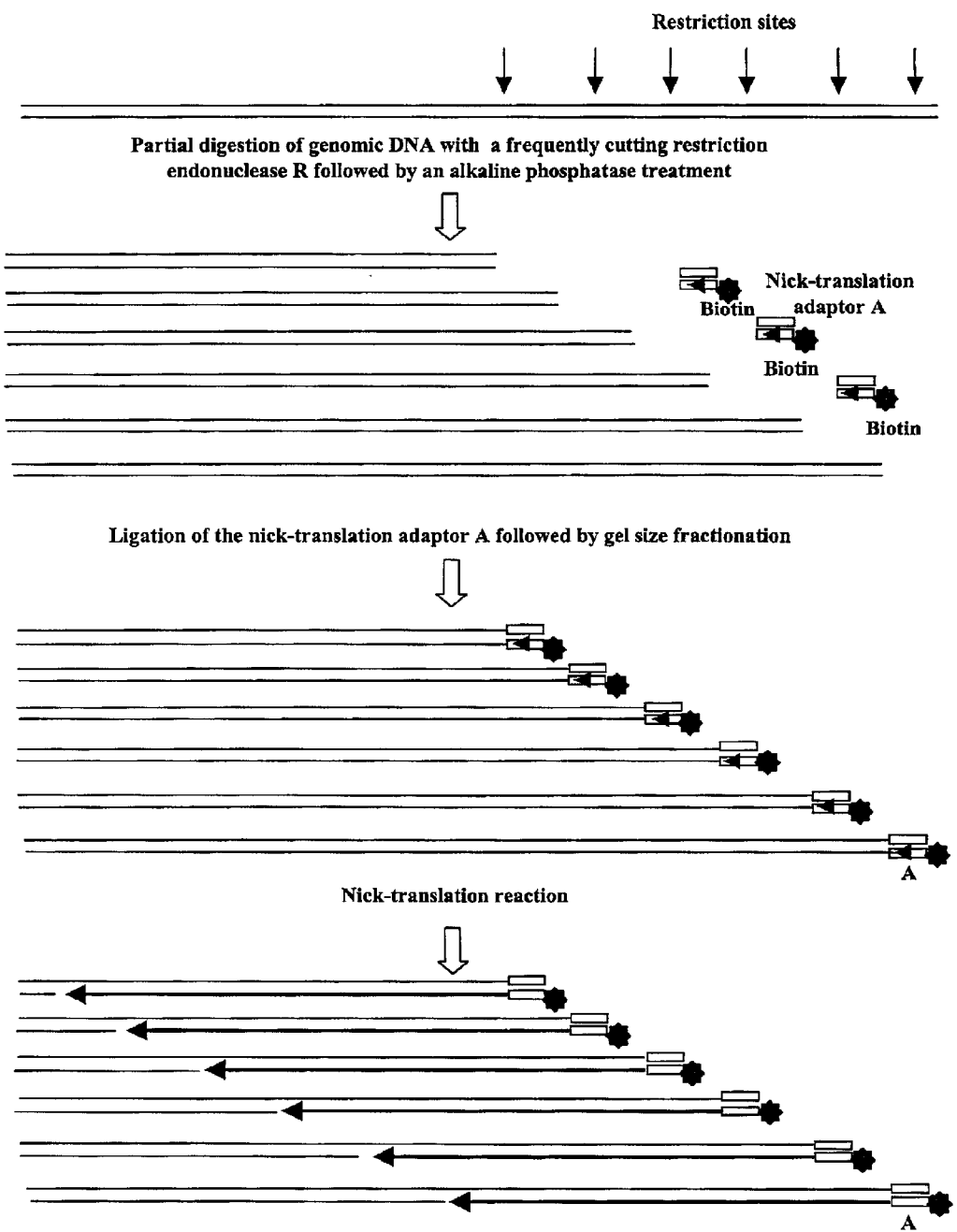
FIGS. 5A and 5B show synthesis of the primary PENTAmer library from a partially digested genomic DNA.
Figure 5B:
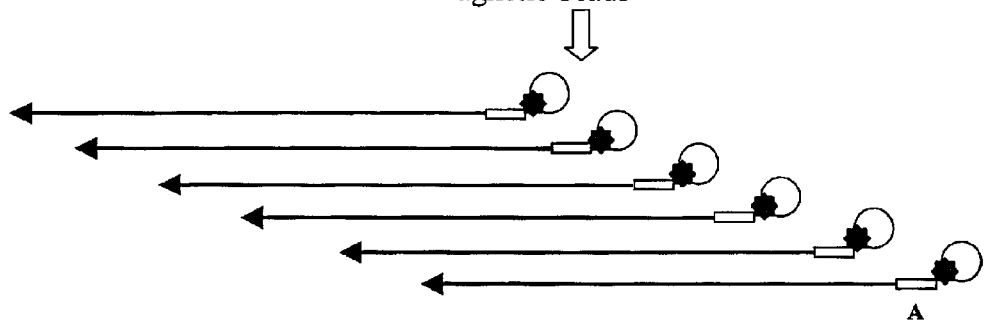
Figure 5B:
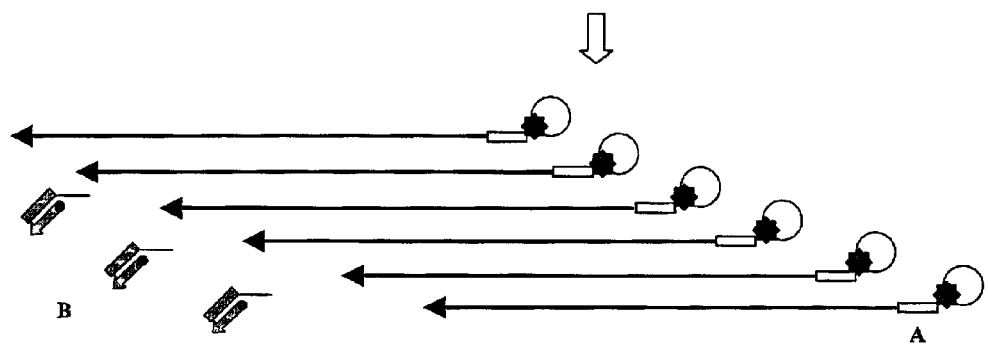
Figure 5B:
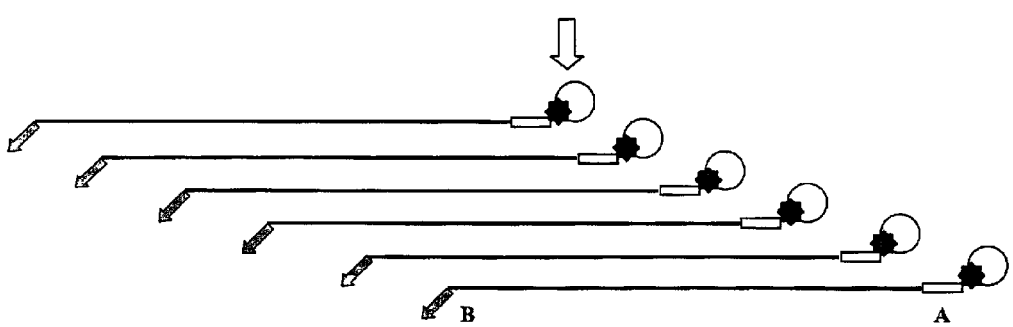

FIGS. 5A and 5B illustrate the preparation of primary PENTAmer library produced by a partial digestion of DNA with a restriction enzyme R presented in the Protocol 2:

1. Protocol 2: Preparation of the Primary PENTAmer Library by a Partial Digestion with a Frequently Cutting Restriction Enzyme a. Digest DNA partially with a frequently cutting restriction enzyme with 4 or 3 base specificity using limited time or limited enzyme strategy, or using a combined restriction digestion/methylation method. A skilled artisan recognizes that there are many suitable enzymes, such as Sau3A I, Nla III, Cvi J, etc. Stop the reaction.

b. Incubate DNA samples with the alkaline phosphatase for an appropriate time to remove the phosphate group from all 5' DNA restriction fragments (this step is optional). Purify DNA by phenol/chloroform extraction-ethanol precipitation or using commercially available DNA purification kits.

c. Ligate the nick-translation adaptor A to all DNA ends. Purify DNA.

d. Fractionate DNA by a gel electrophoresis to isolate fragments larger than double size of a PENTAmer molecules. The PENTAmers from smaller restriction fragments will be shorter than the expected PENTAmer size because of a premature collapse of two nick-translation reactions initiated at the opposite ends of the DNA fragments.

e. Incubate with a DNA polymerase possessing 5' exonuclease activity (for example, non-mutated Taq DNA polymerase) for a specific time to synthesize DNA molecules of a controlled size (PENT products).

f. Isolate PENT molecules by capturing on the streptavidin-coated magnetic beads.

g. Ligate the second adaptor B to the 3' ends of immobilized PENT molecules. Wash.

Figure 6:
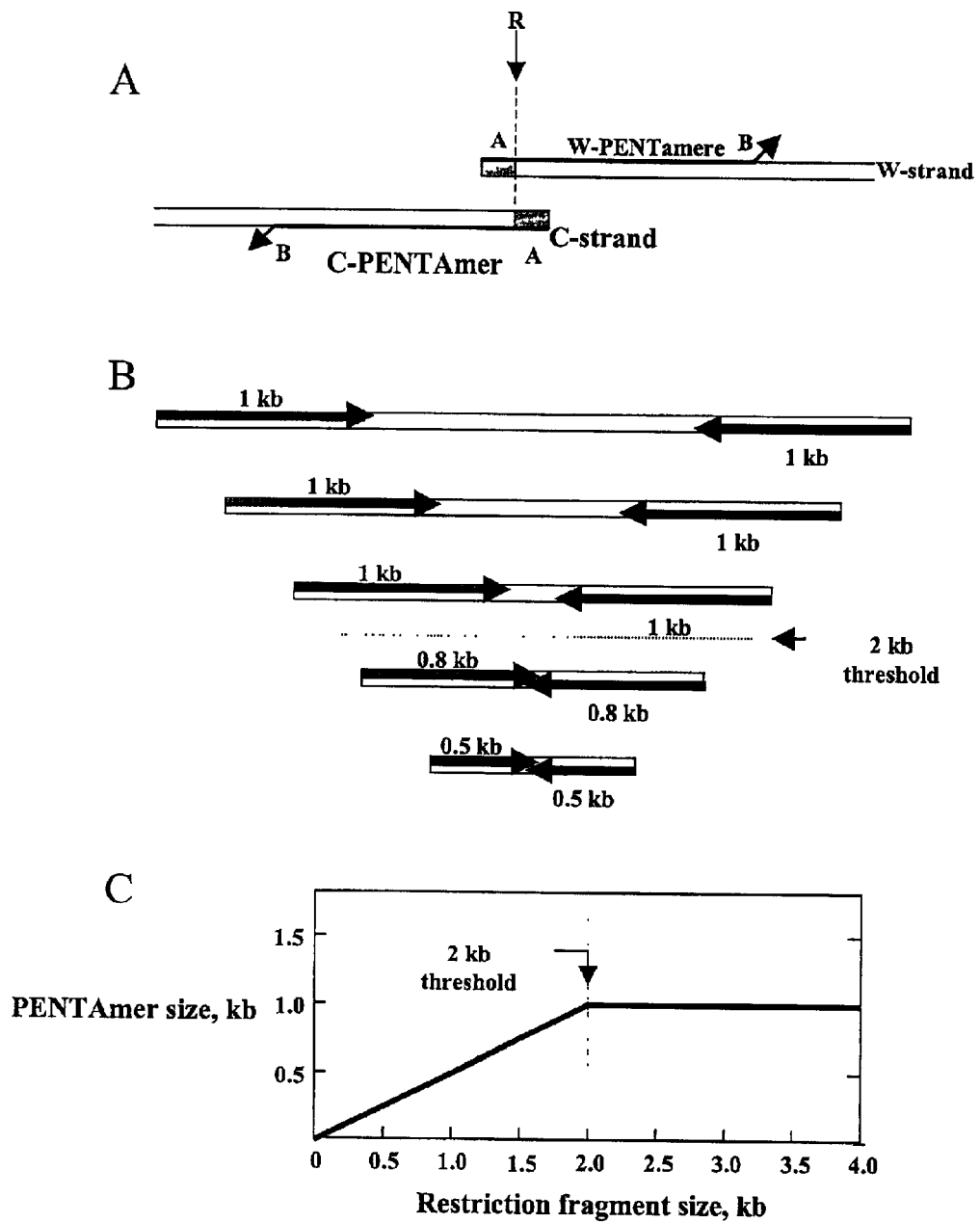
FIG. 6 demonstrates premature termination of the PENTAmer synthesis on short DNA fragments.

The PENTAmers prepared from a partially digested DNA are substantially overlapped and form a highly redundant DNA library. The size fractionation step is important because partial digestion generates DNA molecules of all sizes with about the same probability. As a result, the PENTAmers from DNA fragments with the size smaller than double size of the expected PENTAmer amplicon length will be shorter because of a premature collapse of two nick-translation reactions initiated at the opposite ends of the DNA fragments (FIGS. 6B and 6C).

The overlapping PENTAmer library is used to walk along a chromosome. In principle, the walking strategy would be very similar to that described in a previous section if there is a way to selectively amplify individual PENTAmer molecules. As an example, FIG. 3B shows 21 overlapping PENTAmer molecules from the library generated by partial digestion of DNA with a restriction endonuclease R (only PENTAmers from the bottom strands are illustrated). A minimal tiling path in this case can be created by a selective amplification and sequencing of the molecules $P_1$, $P_5$, $P_9$, $P_{13}$, $P_{17}$ and $P_{21}$ from a single nick-translate library R.

As described herein, there are several ways to select and amplify a unique amplicon using the overlapping PENTAmer library. The present invention is also directed to solving the problem of sequencing complex mixtures of PENTAmers which are easy to generate by a conventional PCR.

C. PCR Amplification of the Overlapping PENTAmer Libraries

Figure 7:
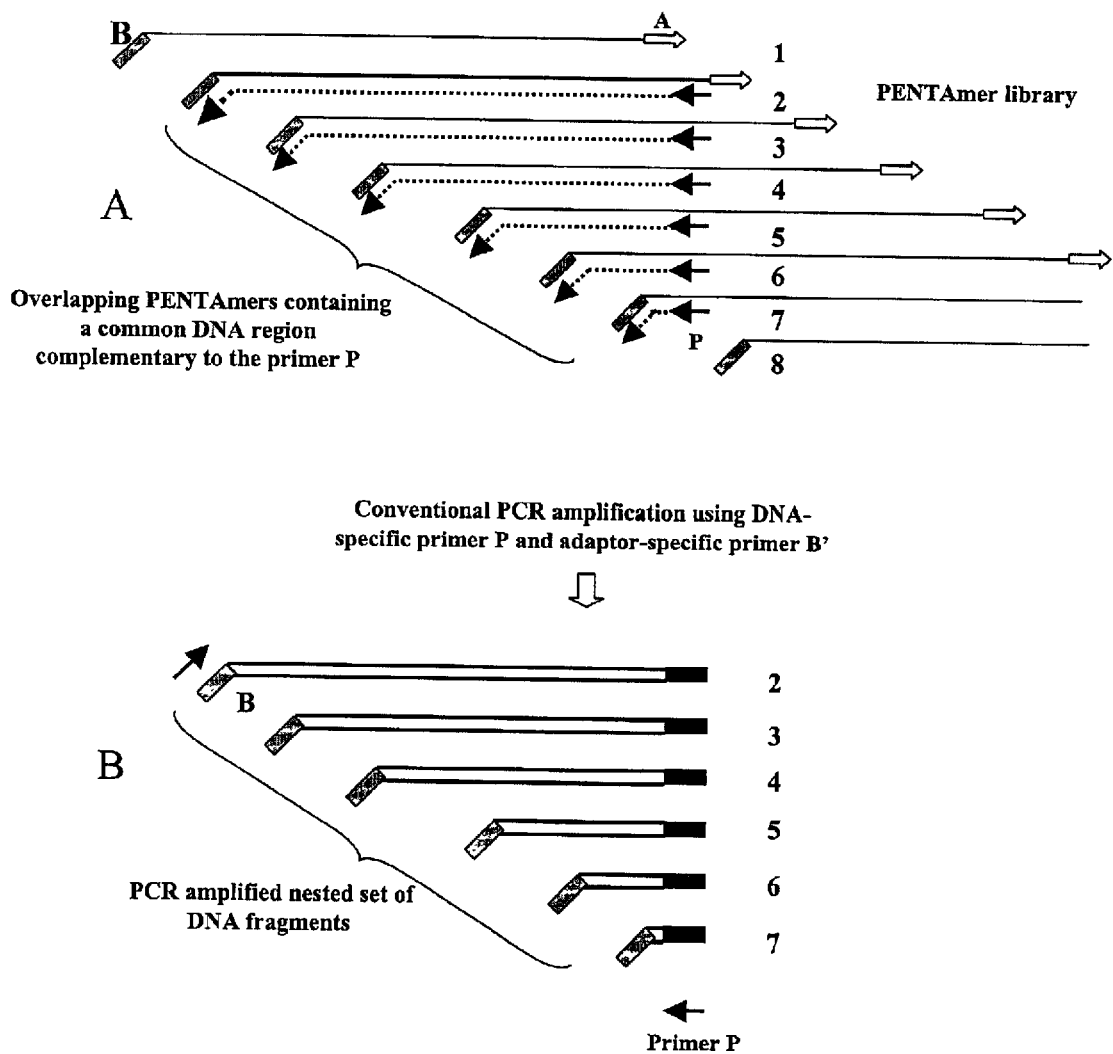
FIG. 7 illustrates amplification of the PENTAmer library produced by a partial restriction digestion using conventional PCR.

Amplification of overlapping PENTAmers by standard PCR using one sequence-specific and one universal primer would result in selection and amplification of several molecules, specifically, a nested set of DNA fragments of different length which share the same priming site P (FIG. 7). For example, from eight overlapping PENTAmer molecules shown on FIG. 7 only the molecules ##2 to 7 will serve as templates for a primer-extension reaction with primer P. It is not obvious that the amplified molecules ##2–7 (FIG. 7) could be directly used for DNA sequencing using primer P (or nested primer P') as a sequencing primer. Two factors could potentially affect the quality and length of the resulting sequencing ladder.

First, the bias towards a preferential amplification of the shortest DNA fragments could reduce the length of DNA sequencing.

Second, the overlap between the universal adaptor sequence at the "fuzzy" end of short DNA fragments and the DNA sequence of longer fragments could result in ambiguities in the base calling in the region of overlap.

There are several ways to minimize the number of PENTAmers which can be amplified using PCR.

1. Sequence Analysis by the Sub-Libraries Approach

The method relies on the segregation of PENTAmer molecules into sub-fractions according to a base composition at the region adjacent to the restriction site. The segregation is achieved by selective priming and synthesis of DNA molecules using a set of biotinylated selective primers A* and universal primer B. As in an AFLP method selective primers are complementary to the adaptor sequence A and the restriction site plus have an extra selective base(es) at their 3' end. For example, four one-base selective primers shown on FIGS. 8A and 8B have in addition an extra G, A, T or C base at the 3' end. Sixteen two-base selective primers have two additional selective bases at the 3' end, and so on.

Figure 8A:
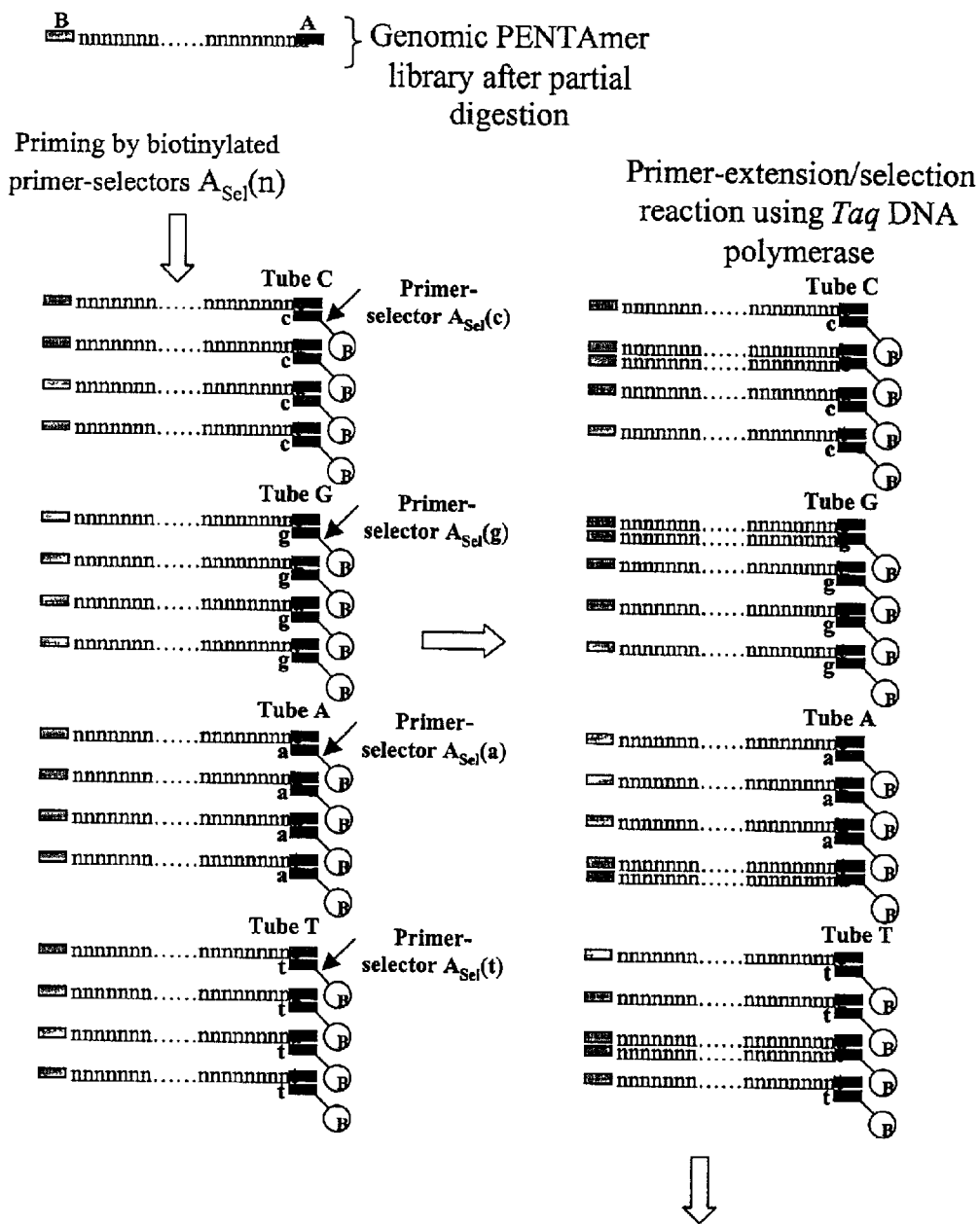
FIGS. 8A and 8B show one-base selection by primer-extension/affinity capture procedure.
Figure 8B:
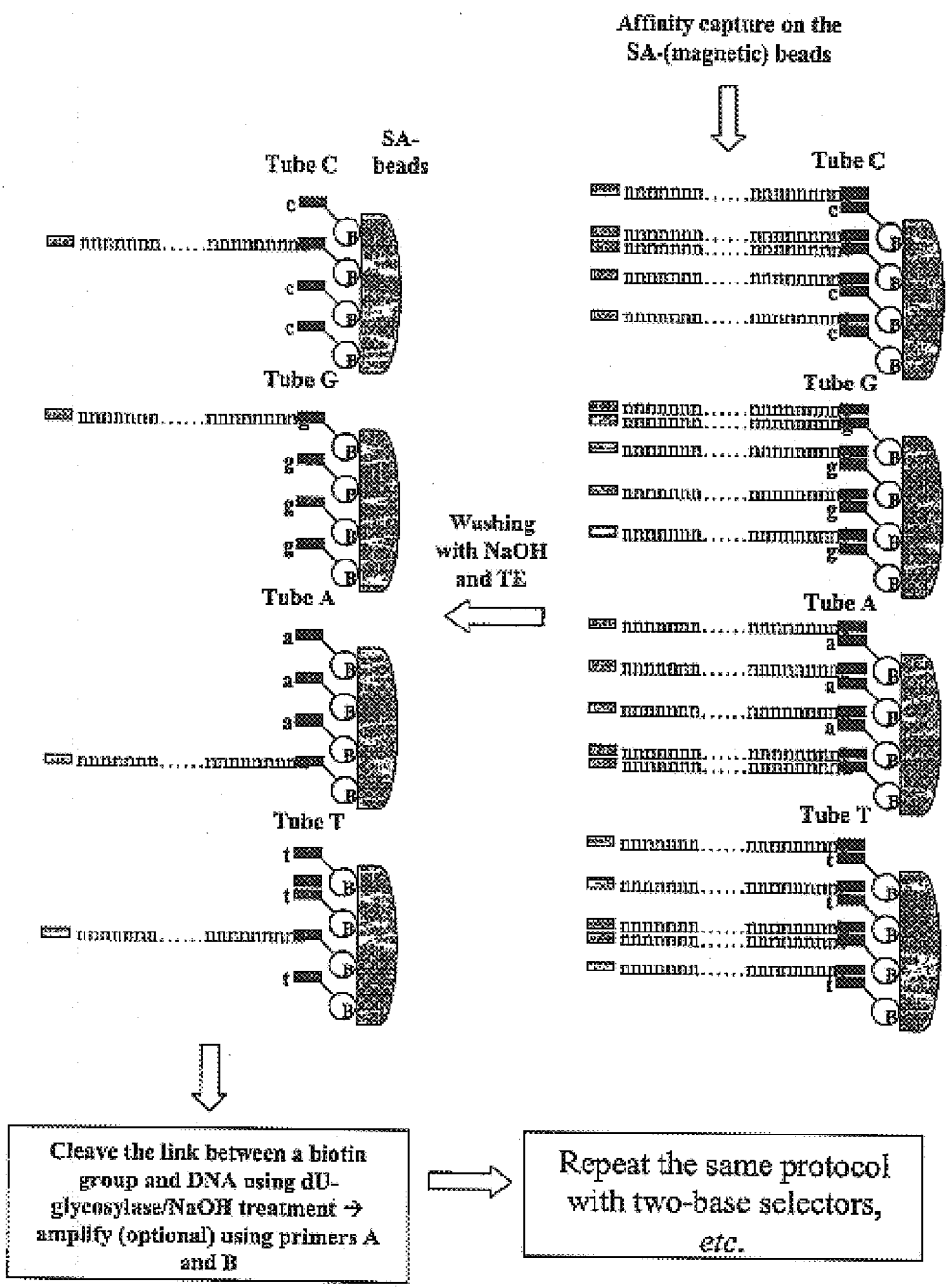

The first step involves hybridization and extension of primer-selectors using wild type Taq DNA polymerase (FIGS. 8A and 8B). The reactions proceed in four different tubes.

In a second step, selected molecules are immobilized on the streptavidin coated magnetic beads and washed to remove the rest of DNA (FIGS. 8A and 8B).

Figure 9:
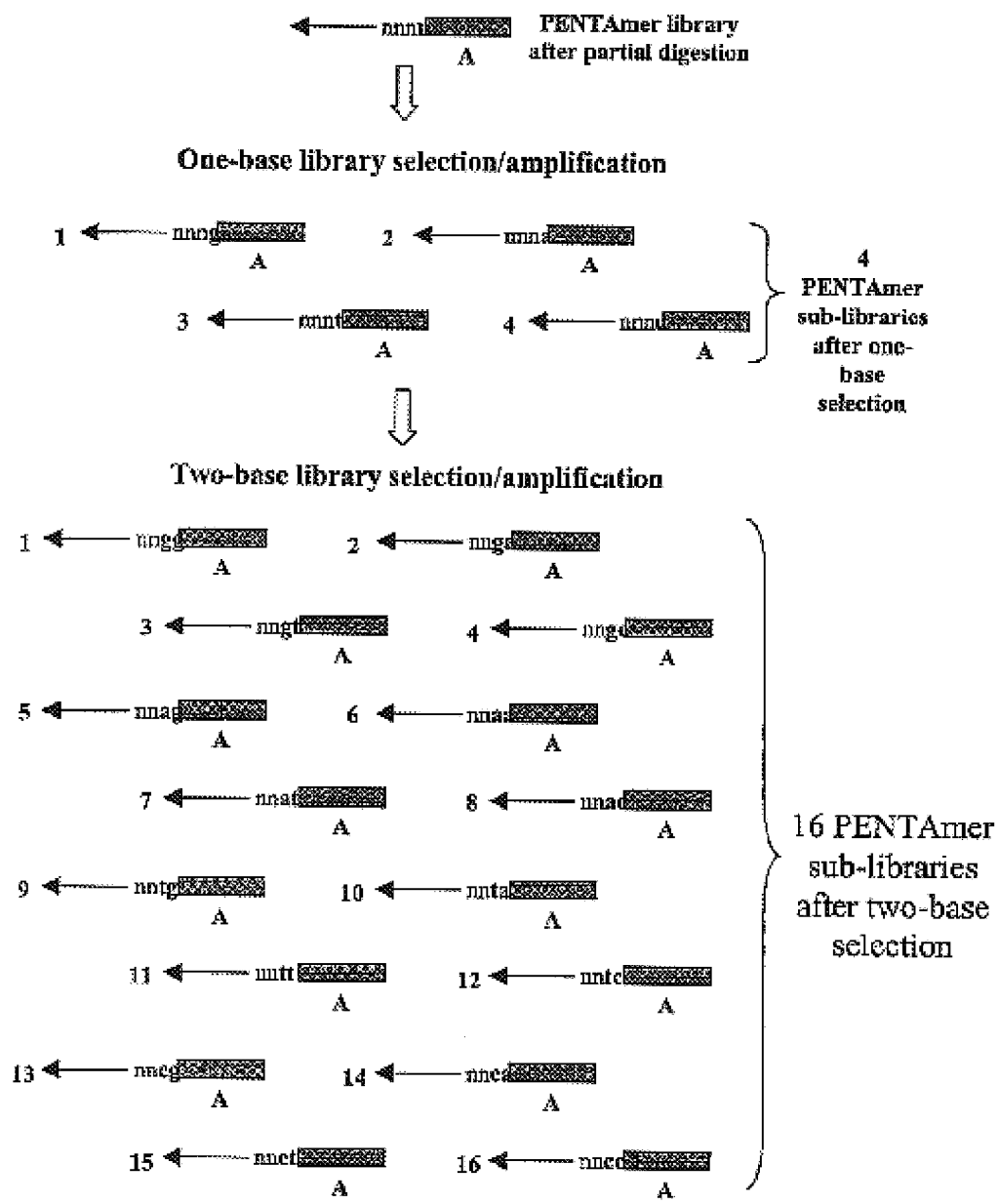
FIG. 9 demonstrates reducing the PENTAmer library complexity by primer extension/polymerase chain reaction with primer-selector A.

The next level of selection can be achieved by cleaving off the biotin moiety, releasing selected molecules into solution and repeating the selection step with a new set of selective primers. For example, after segregation of the PENTAmer library into 4 pools "G", "A", "T", and "C" using one-base selective primers, the sub-libraries can be further segregated into 16 pools using two-base selective primers (FIG. 9).

Walking with pre-selected sub-libraries is very similar to the walking process described previously herein, when multiple sub-libraries are created by cleavage with multiple restriction enzymes. Amplification of a selected sub-library with standard PCR using one sequence-specific and one universal primer would result in selection and amplification of a very limited number of molecules, presumably just one (largest) amplicon.

2. Sequence Analysis by the Size Fractionation Approach.

Figure 10:
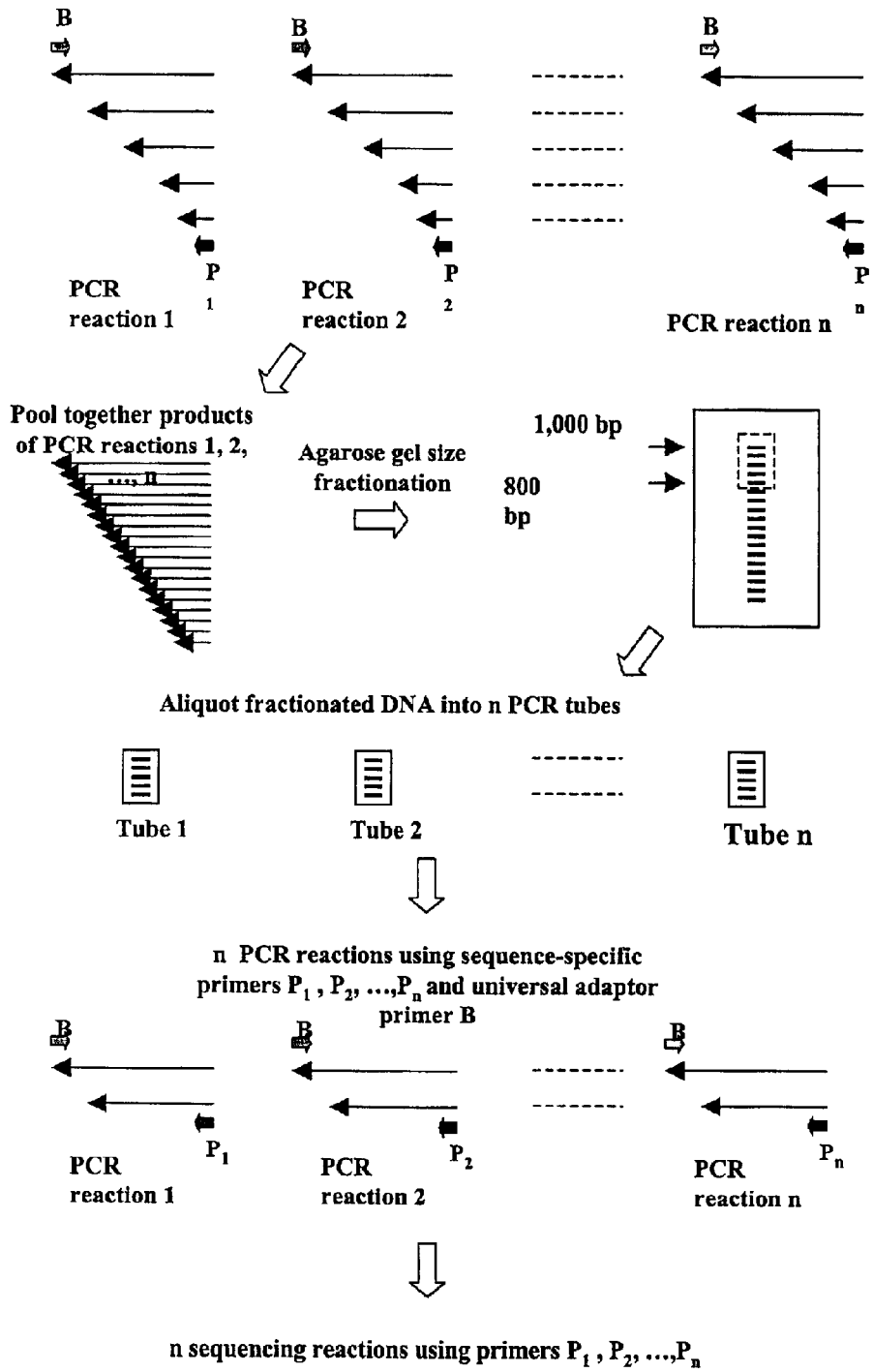
FIG. 10 illustrates genome walking using overlapping PENTAmer library, conventional PCR, and DNA size fractionation-pooling strategy.

Another solution to the problem is to fractionate the molecules after PCR by size using gel electrophoresis or chromatography and use for sequencing only DNA molecules larger than, for example, about 800 bp. To reduce the number of samples for preparative size fractionation, the PCR products generated by different sequence-specific primers $P_1$, $P_2$, ..., $P_n$ and one universal primer-adaptor B can be pooled together, size fractionated, aliquoted into n different tubes and re-amplified again using the same primers (FIG. 10).

The molecules for size fractionation can be generated also by n primer-extension reactions with sequence-specific primers $P_1$, $P_2$, ..., $P_n$ or even one multiplexed polymerase-extension reaction using primers $P_1$, $P_2$, ..., $P_n$ combined together in a one tube.

3. Sequence Analysis by the Suppression PCR Method

Figure 11:
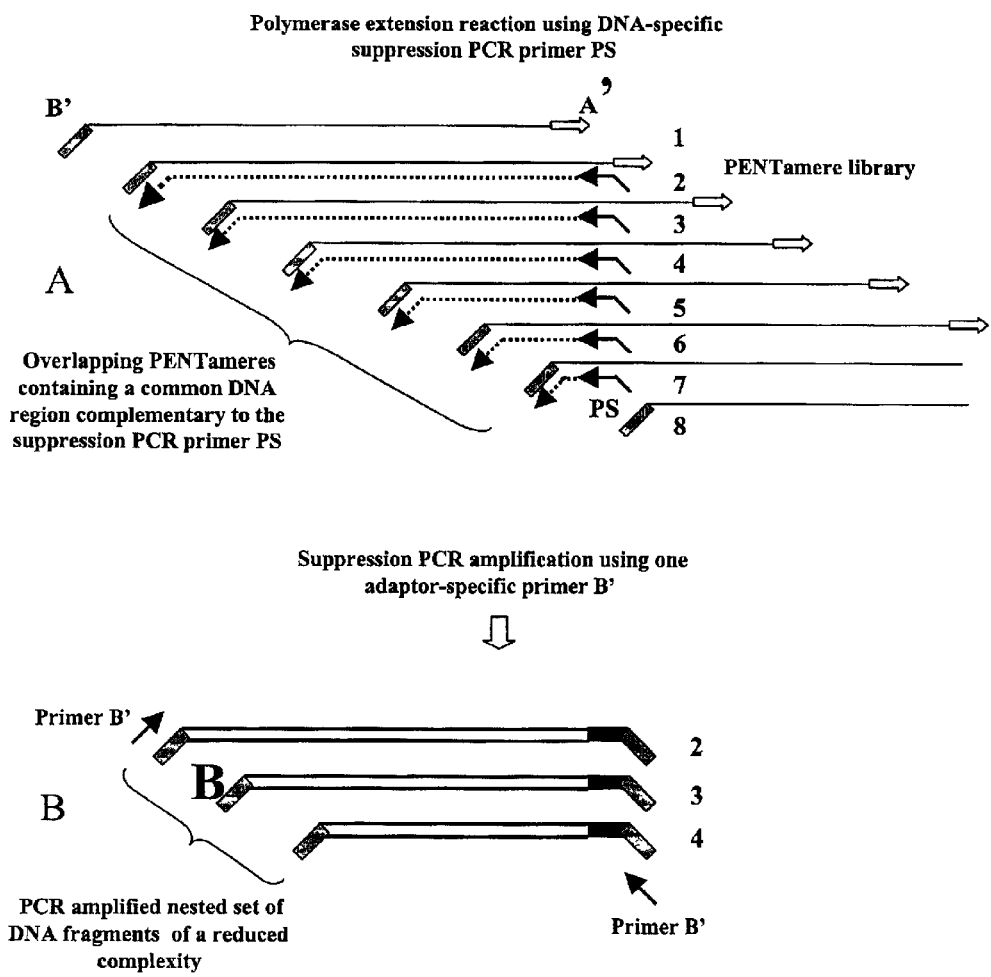
FIG. 11 illustrates amplification of the PENTAmer library produced by a partial restriction digestion using suppression PCR.

An additional approach to reduce the representation of short DNA fragments is to use a suppression PCR (Siebert et al., 1995) wherein the sequence-specific primer PS is designed to have an additional 5' sequence which is identical to the sequence of the universal adaptor primer B (FIG. 11). The reaction is initiated by limited number of linear amplifications using sequence-specific suppression-PCR primer PS (FIG. 11) and completed by using suppression PCR mode with the universal primer B (FIG. 11). Because of formation of a specific panhandle DNA structure at the ends of DNA fragments the amplification of the shortest DNA fragments is suppressed and only large DNA molecules would be amplified (FIG. 11). Suppression PCR offers an additional level of selection, namely, selection according to DNA fragment size.

4. Sequence Analysis by the Enzymatic Pre-Selection Approach

Figure 12:
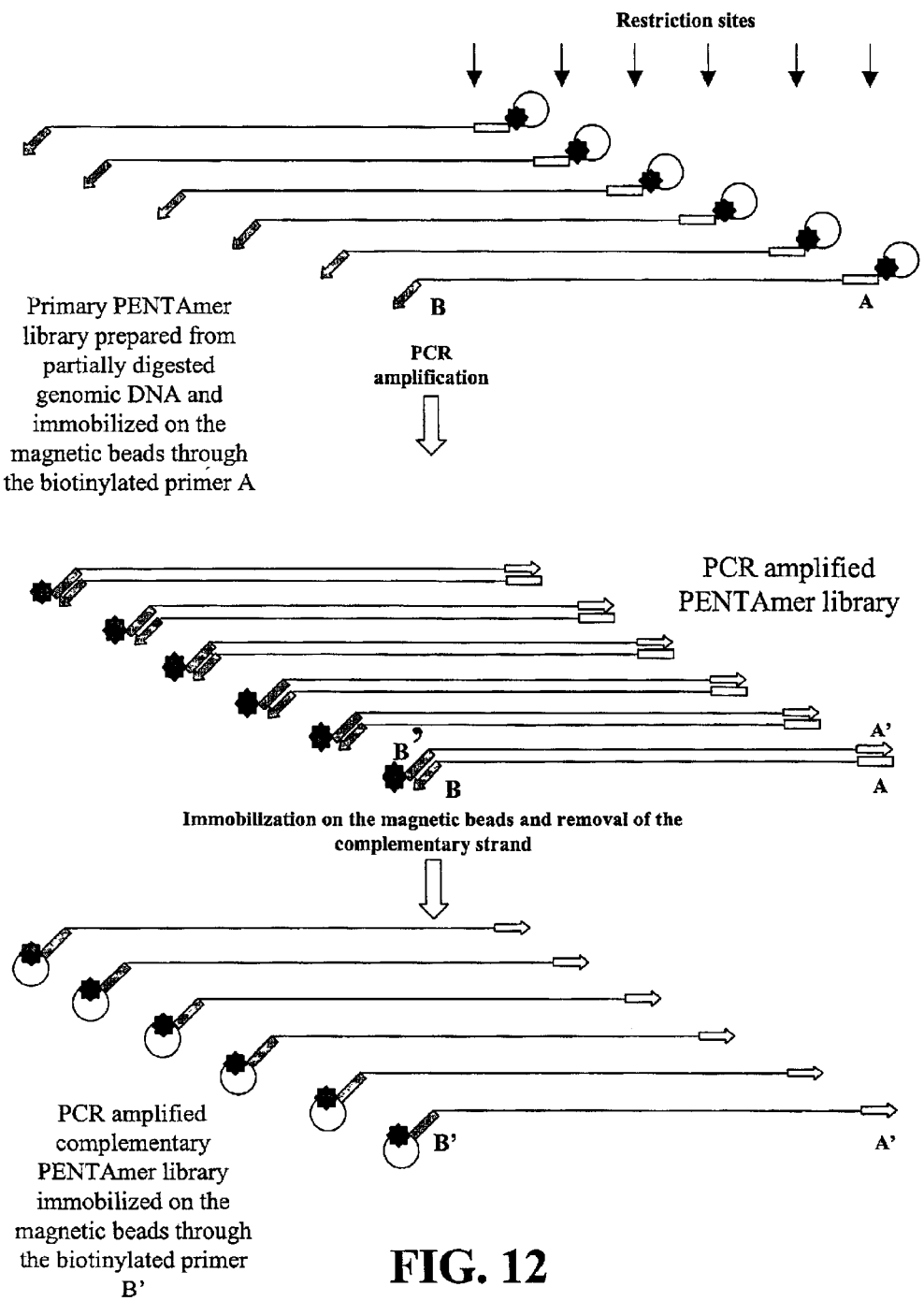
FIG. 12 illustrates preparation of the immobilized single-strand complementary PENTAmer library for the selection-amplification procedure.

It is also feasible to amplify only one nick-translate DNA molecule, namely, the largest molecule of the nested set shown on FIG. 7 by adding an additional enzymatic selection reaction. This type of selection can be achieved by targeted ligation-mediated amplification. The following section describes four different protocols of the targeted PENTAmer amplification. However, prior to the targeted PENTAmer amplification, the PENTAmers are preferably immobilized and rendered single stranded, such as is illustrated in FIG. 12.

a. Method 1

Figure 13A:
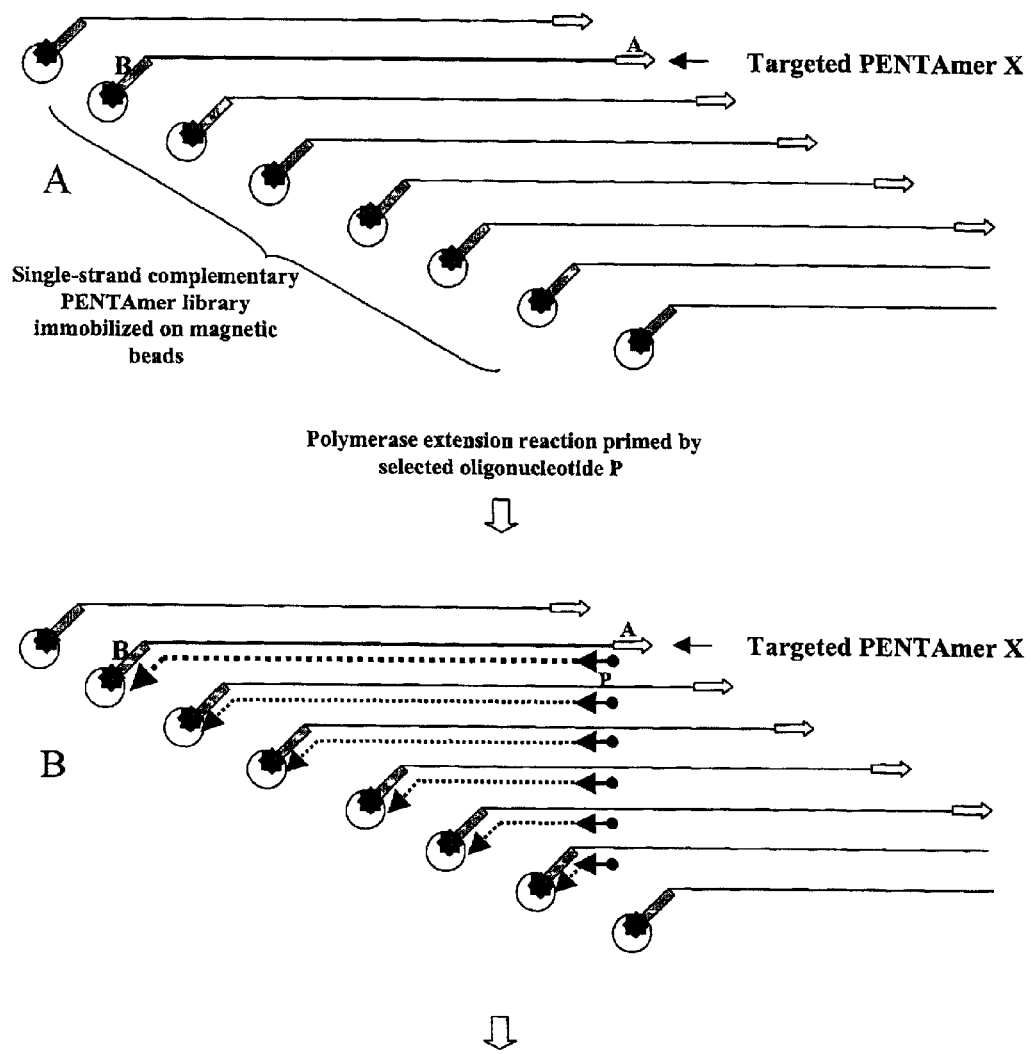
FIGS. 13A and 13B shows targeted PENTAmer amplification by primer extension-ligation-Method I.
Figure 13B:
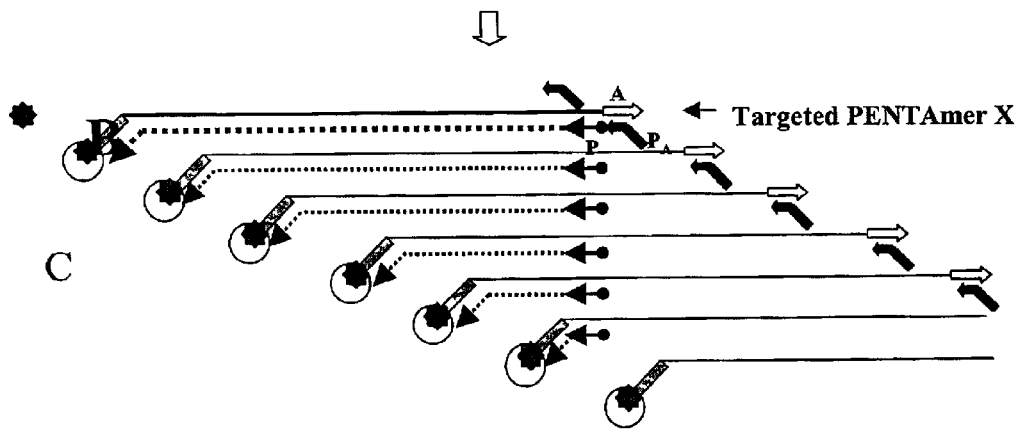
Figure 13B:
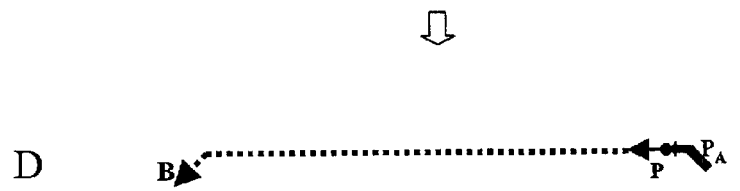
Figure 13B:
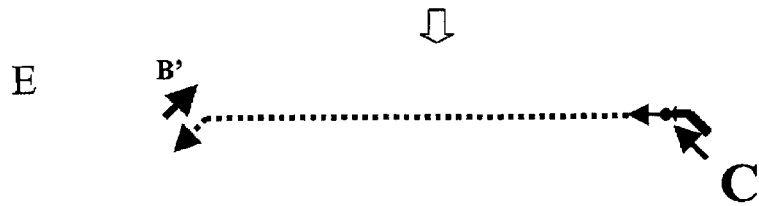
Figure 14A:
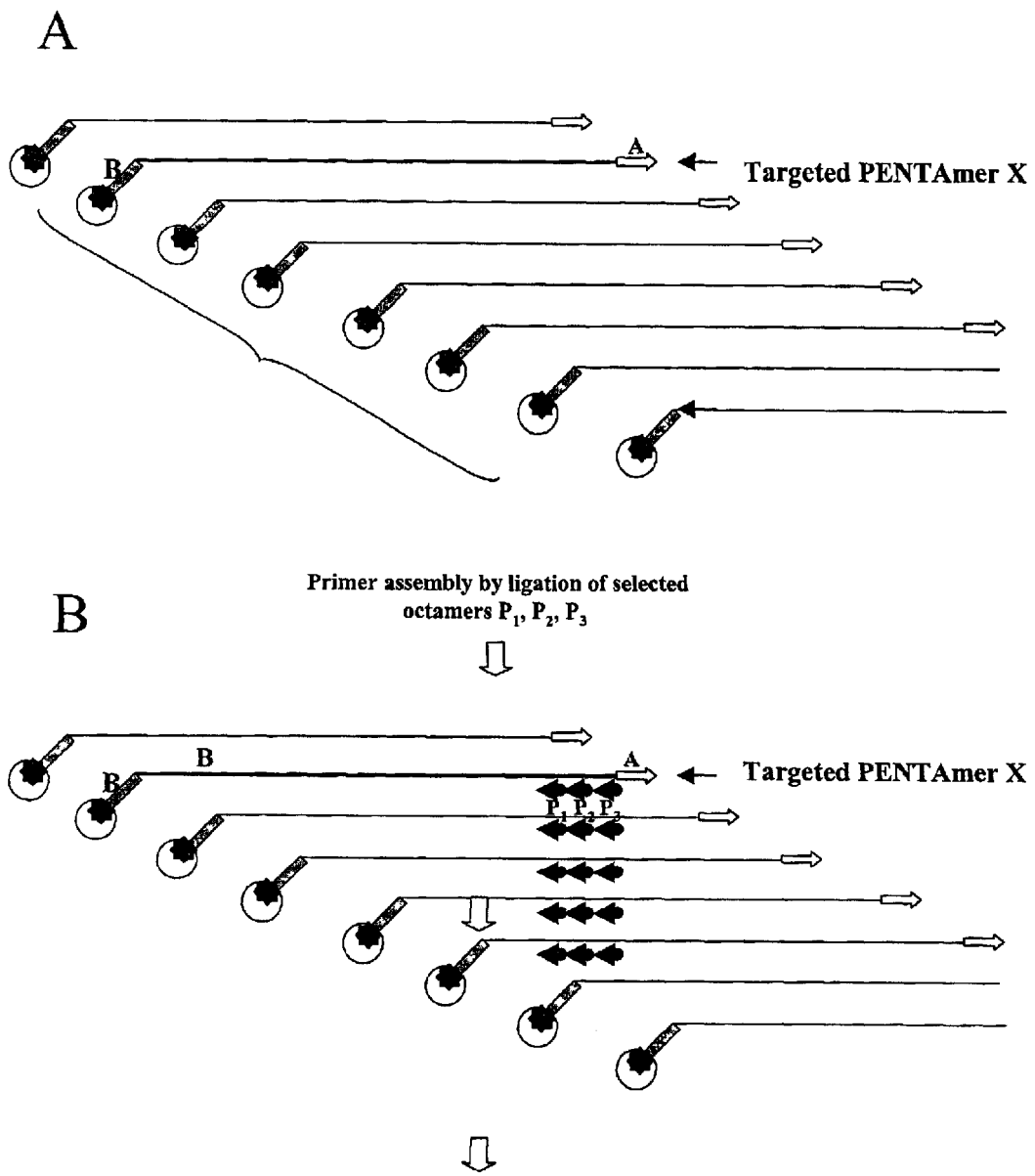

FIGS. 13A and 13B show the first targeted amplification method. It involves four major steps.

Step 1. Polymerase extension reaction with phosphorylated primer-selector $P_x$ complementary to the left side of the restriction site $R_x$ (FIGS. 13A and 13B). Priming occurs internally within several overlapping PENTAmer molecules except PENTAmer X where priming occurs at the "restriction" end of the DNA fragment in the region immediately adjacent to the adaptor sequence A.

Step 2. Ligation of the tagged oligonucleotide $P_A$ to the 5' end of the extension product. Oligonucleotide $P_A$ is complementary to the adaptor A, and it is ligated only to the terminally extended molecule on the targeted PENTAmer X (FIG. 13C).

Step 3. Degradation of the template PENTAmer DNA library by incubation with dU-glycosylase, followed by heating (FIG. 13D)

Step 4. PCR amplification using primers B and C (5' portion of the tagged oligo $P_A$) (FIG. 13E).

b. Method 2

FIGS. 14A through 14E illustrate second protocol for the targeted amplification of PENTAmers. It has five major steps.

Step 1. Ligation-assembly reaction using short phosphorylated oligonucleotides $P_1$, $P_2$, $P_3$ complementary to the left side of the restriction site $R_x$, thermostable ligase and moderate temperature. Primer assembly occurs internally within several overlapping PENTAmer molecules except PENTAmer X where priming occurs at the "restriction" end of the DNA fragment in the region immediately adjacent to the adaptor sequence A (FIG. 14B).

Step 2. Polymerase extension reaction at an elevated temperature.

Priming occurs internally within several overlapping PENTAmer molecules except PENTAmer X where priming initiated terminally (FIG. 14C).

Step 3. Ligation of the tagged oligonucleotide $P_A$ to the 5' end of the extension product. Oligonucleotide $P_A$ is complementary to the adaptor A and it is ligated only to the terminally extended molecule on the targeted PENTAmer X (FIG. 14D).

Step 4. Degradation of the template PENTAmer DNA library by incubation with dU-glycosylase followed by heating.

Step 5. PCR amplification using primers B and C (5' portion of the tagged oligo $P_A$) (FIG. 14E).

c. Method 3

FIGS. 15A through 15E show a third approach. It involves four major steps.

Figure 15A:
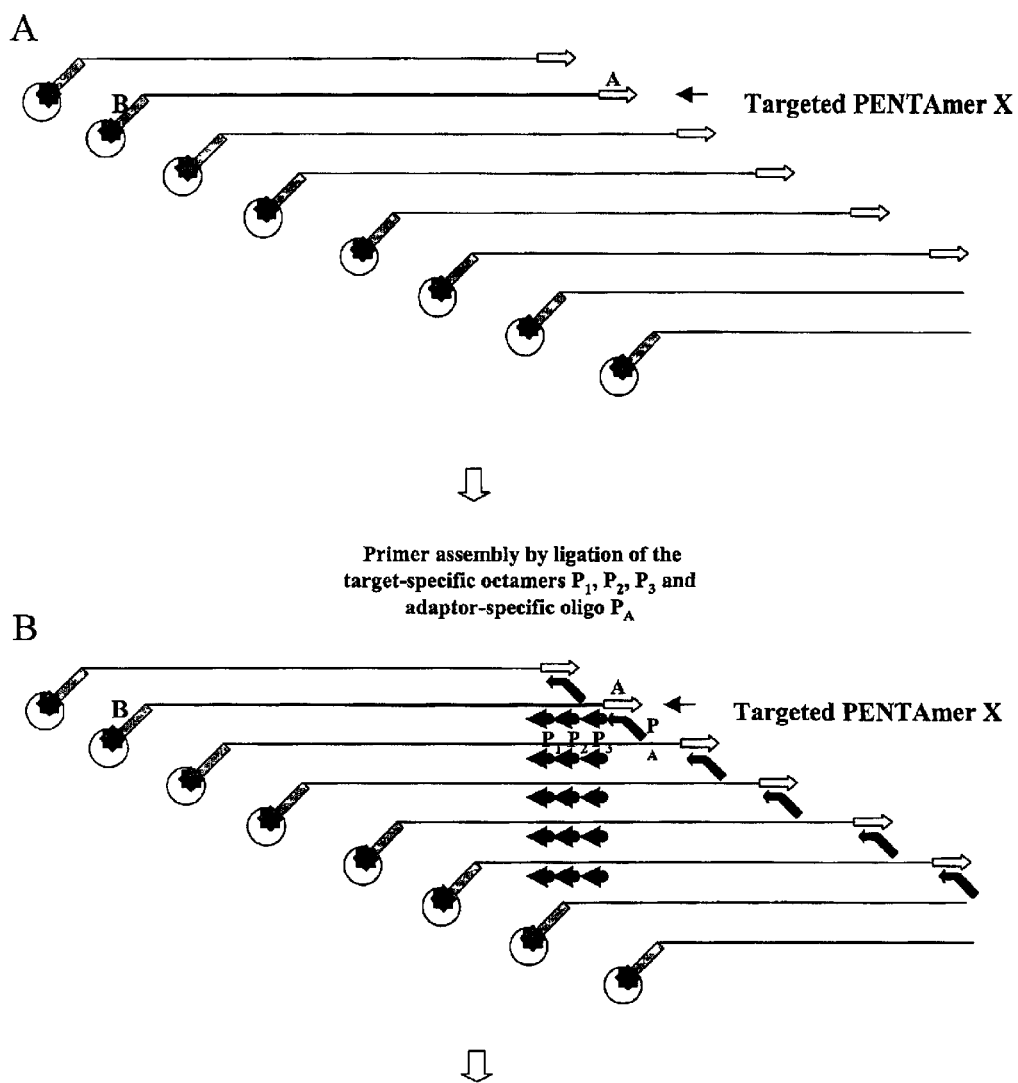
FIGS. 15A and 15B demonstrates targeted PENTAmer amplification by modular oligonucleotide assembly-Method III.
Figure 15B:
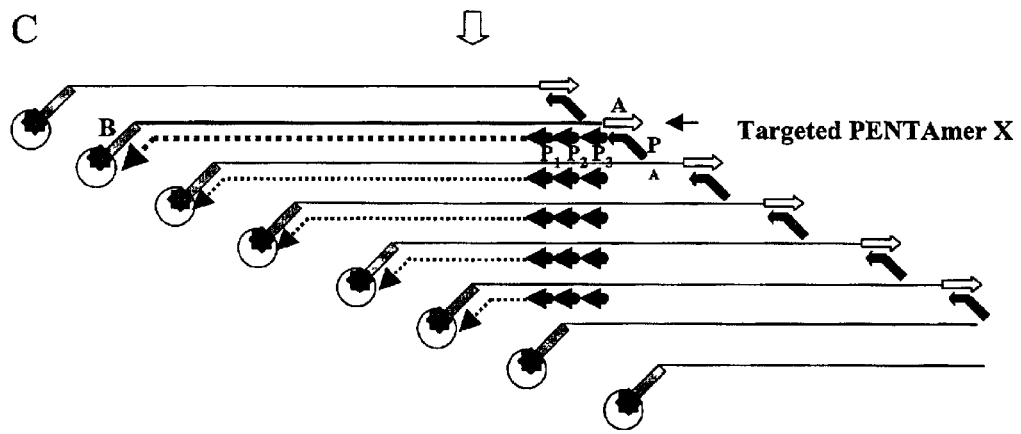

Step 1. Ligation-assembly reaction using short phosphorylated oligonucleotides $P_1$, $P_2$, $P_3$ complementary to the left side of the restriction site $R_x$ and the tagged oligonucleotide $P_A$ complementary to the adaptor A DNA sequence, thermostable ligase and moderate temperature. Assembly of larger oligomers from oligos $P_1$, $P_2$, $P_3$ occurs internally within several overlapping PENTAmer molecules but incorporation of the tailed oligo $P_A$ occurs only at the end of the PENTAmer X (FIG. 15B)

Step 2. Polymerase extension reaction at elevated temperature. Priming occurs internally within several overlapping PENTAmer molecules but only extension reaction with PENTAmer X as a template results in a full size product with $P_A$ tail (sequence C) at the 5' end (FIG. 15C).

Step 3. Degradation of the template PENTAmer DNA library by incubation with dU-glycosylase followed by heating (FIG. 15D).

Step 4. PCR amplification using primers B and C (5' portion of the tagged oligo $P_A$) (FIG. 15E).

The first three selection procedures suggests that:

(a) PENTAmer molecules have a single stranded form; b) the strand complementary to the primary PENTAmer is used for the selection, namely, the strand 5'B→3'A (the primary PENTAmer has an opposite orientation 5'A→3'B) (FIGS. 5A and 5B); c) molecules are immobilized through a 5'-biotin group (primer B) on the solid support (magnetic beads); and d) a fraction of dT nucleotides is replaced with dU nucleotides during preparation of the PENTAmer library Conditions a) and b) are important prerequisites of protocols #1, 2 and 3 for targeted PENTAmer amplification. Factor c) simplifies the removal of enzymes and triphosphates, but it is not detrimental. Factor d) allows elimination of original templates and reduces amplification of the non-specific products.

Figure 15B:
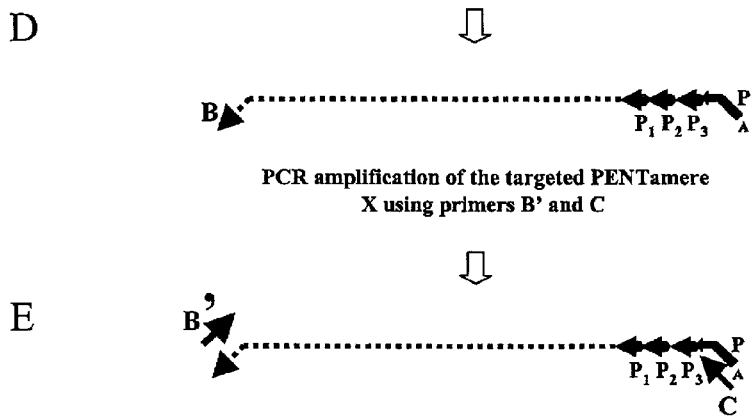

The first method utilizes a standard about 20–30 base long oligo-primer for the extension reaction. In the second approach, the primer is assembled by ligation of short (i.e. octamers) phosphorylated target-specific oligonucleotides $P_n$ from a pre-synthesized oligo-library. FIGS. 14 and 15 show the assembly of only three sequence-specific oligonucleotides $P_1$, $P_2$, $P_3$, but their number can be substantially higher. The third method combines into one step a ligation of the target-specific oligonucleotides $P_n$ and the adaptor-specific oligo $P_A$.

There are two reasons why the second and third selection protocols are preferable to the first protocol presented in FIGS. 13A–13E. First, they allow an increase in the stringency of the primer-extension step. Usually polymerases are more sensitive to the mismatches within the 3' region of the primer and can easily tolerate mis-pairing in the central and 5'-portion. Thermostable ligases are also better at discriminating mismatches located at the 3' end of the oligonucleotides during their ligation. Without wishing to be bound to one theory, the inventors believe that primer assembly by ligation of short DNA molecules allows increase in the specificity and the selection power of the targeted amplification method due to the higher mismatch discrimination of multiple internal base positions within the priming site.

Second, it offers a significant reduction of turn-around time and cost of the "walking" procedure. The library of all octamer oligonucleotides can be pre-synthesized, and the whole amplification-sequencing process can be completely automated.

d. Method 4

The fourth protocol is different in that it uses a non-immobilized DNA library and adds an additional selection step at the level of affinity capture of the ligation-selected primer-extended PENTAmer molecules (FIGS. 16A through 16E). Otherwise, it is similar to the Method 1. FIGS. 16A through 16E show the fourth targeted amplification method involving five major steps.

Figure 16A:
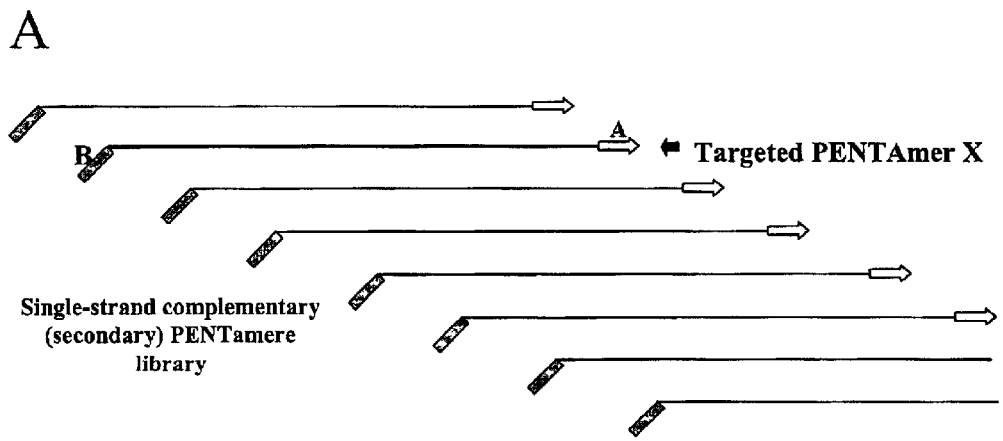
FIGS. 16A and 16B demonstrates PENTAmer selection by primer extension/ligation followed by magnetic bead capture.
Figure 16A:
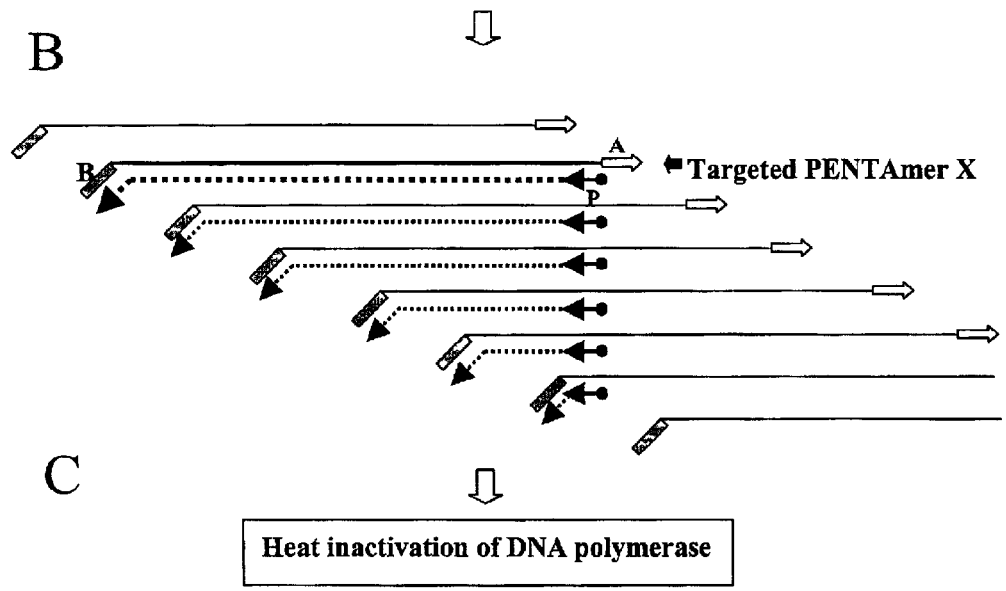
Figure 16B:
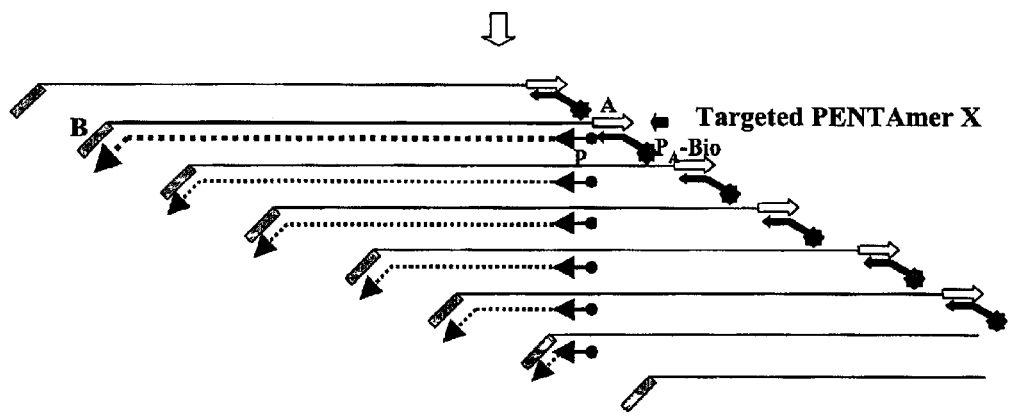
Figure 16B:
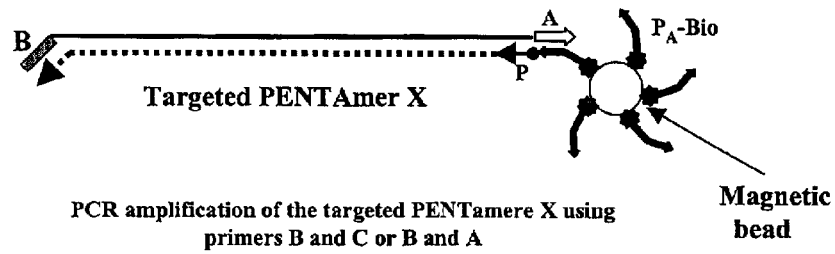
Figure 16B:
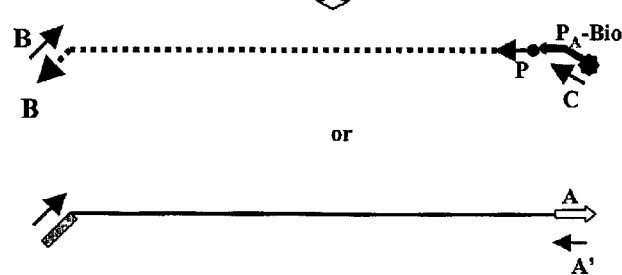

Step 1. Polymerase extension reaction with phosphorylated primer-selector P complementary to the left side of the restriction site R and Bst (heat sensitive) DNA polymerase (FIGS. 16A and 16B).

Priming occurs internally within several overlapping PENTAmer molecules except PENTAmer X where priming occurs at the "restriction" end of the DNA fragment in the region immediately adjacent to the adaptor sequence A.

Step 2. Heat inactivation of Bst DNA polymerase (FIG. 16C).

Step 3. Ligation of the tagged oligonucleotide $P_A$ to the 5' end of the extension product. Oligonucleotide $P_A$ is complementary to the adaptor A and it is ligated only to the terminally extended molecule on the targeted PENTAmer X (FIG. 16D).

Step 4. Magnetic bead capture of the targeted PENTAmer X (FIG. 16E).

Step 5. PCR amplification using primers B and C (5' portion of the tagged oligo $P_A$) or B and A (FIG. 16F).

e. Removal of dU-Containing DNA Molecules

A skilled artisan recognizes that it would be useful to separate a desired molecule, or more than one, from an undesired molecule, or more than one. For example, in the present invention it is useful to separate a selected primer extended molecule from a library of nick translate molecules. A skilled artisan is aware of a variety of means to achieve this, but in the present invention it is preferred to polymerize nick translate molecules in the presence of dU nucleotides, but alternatively polymerize a desired primer extension molecule having no incorporation of dU. In a preferred embodiment, this occurs in the absence of dU nucleotides in a reaction mixture. The dU-containing molecules are then subjected to a dU glycosylase, such as AmpErase Uracil N-glycosylase (UNG) (Applied Biosystems, Foster City, Calif.). When dUTP is substituted for dTTP in PCR amplification, exposure to UNG prevents the subsequent reamplification of dU-containing PCR products. UNG acts on single- or double-stranded dU-containing DNA by hydrolysis of uracil-glycosidic bonds (base excision) at dU-containing DNA sites, releasing uracil and creating an alkali-sensitive apyrimidinic site in the DNA. Thus, uracil N-glycosylase can be used to cleave DNA at any position where a deoxyuridine triphosphate has been incorporated.

D. Direct Sequencing Approach

Surprisingly, the inventors determined that the complex mixtures of nested molecules generated by PCR using one sequence-specific and one universal primer can be directly used for sequence analysis. Example 6 and FIG. 5 shows 55 different loci in the bacterial genome amplified using the PENTAmer library prepared by a partial digestion of the *E. coli* genomic DNA with the Sau3A I restriction enzyme (Example 5), universal primer B (Table VII) and 40 *E. coli*-specific primers (Table VII). As expected, the electrophoretic profiles show a complex multi-band pattern with a maximum size of 1 kb (the PENTAmer size). The PCR products have been subjected to the cycle sequencing protocol using fluorescent dye-terminators and the same primers as used for PCR and then analyzed using the MEGABASE capillary DNA sequencer. The sequencing data have been analyzed by the Megabase capillary sequencing machine (Amersham; Piscataway, N.J.).

Figure 17:
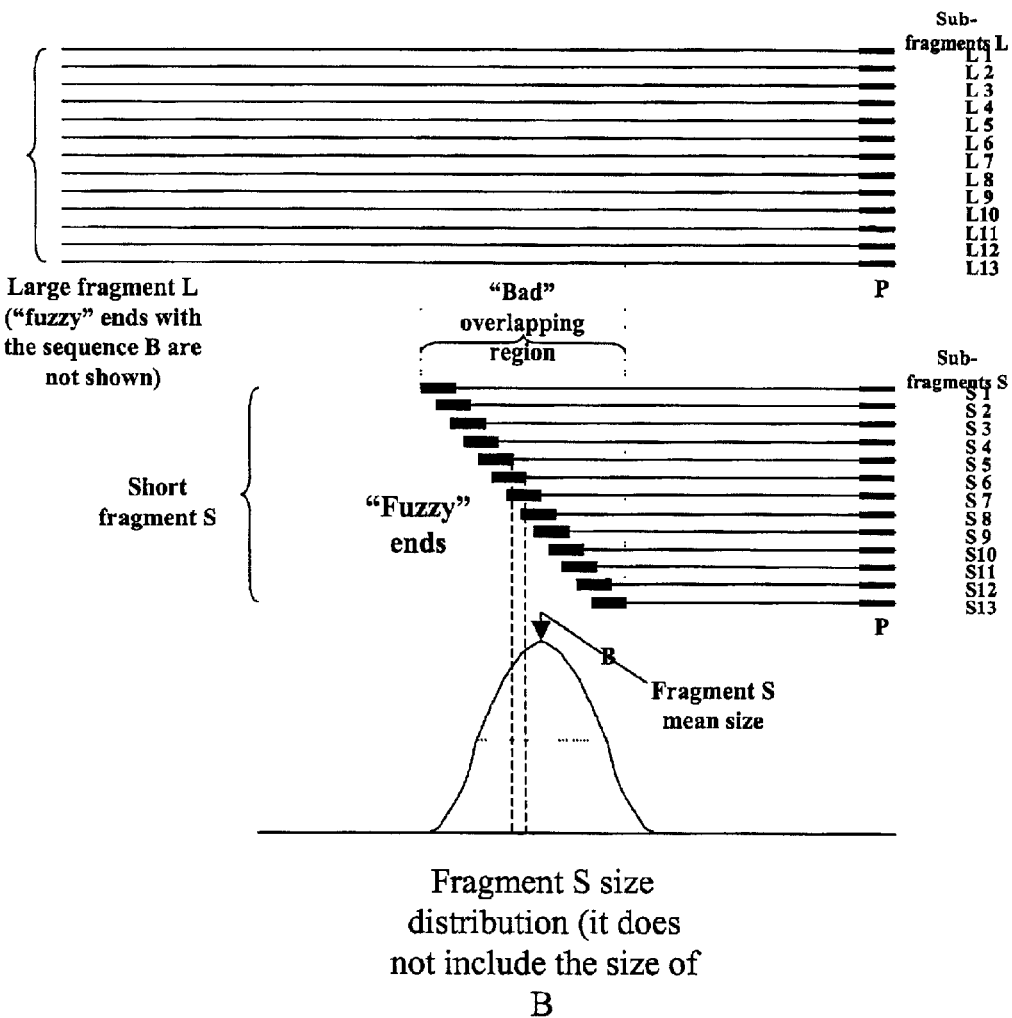
FIG. 17 shows sequencing of two overlapping fragments L and S generated by amplification of PENTAmer library (following partial restriction digestion) using unique primer P and universal primer B.

The adaptor B sequence, which is located at different distances for different fragments, does not noticeably affect the quality of the sequencing data. FIG. 17 shows the simplest case of only two overlapping fragments L (large) and S (short). It is expected that in the "bad" region where the sequence of the fragment L is overlapped with adaptor sequence B, the sequencing can be problematic. However, in the overlap area indicated by two vertical dashed lines, a total 18 DNA templates (L1–L13 from larger DNA fragment A plus S1–S5 from shorter fragment B) produces a correct DNA sequencing ladder. Only 3 DNA templates (B6–B8) will produce an unreadable signal generated by adaptor sequences B. The expected noise-to-signal ratio in the area is only about 3/18=17%.

In reality, the contribution of the adaptor DNA is very small because of two reasons: small size of the B region and the diffuse position of the "fuzzy" end with respect to the DNA priming site. If one assumes the same width of size distribution for both "fragments," it means there are the same number of molecules within a specific size subinterval. For example, for the interval shown on FIG. 17 by two dashed vertical lines, the total number of molecules with a correct DNA sequence is equal to 13 "molecules" originated from the "fragment" L plus 5 molecules originated from the "fragment" S, with total number 18. The number of short "fragments" within the same interval is equal to 3 giving the ratio of 0.17 for the contribution of the "bad" sequence B into the "good" signal. Practically, it can be estimated as a ratio between the adaptor B sequence length and the width of the PENTAmer size distribution. The latter is herein estimated as 150 bp and B is about 22 bp, giving the ratio of 0.15 very close to the hypothetical example shown on FIG. 17.

The diffuse size distribution of the PENTAmer molecules is inherent to the nick-translation process, and it is useful. It is sufficiently narrow to allow one to control the average size of PENTAmers, and it is broad enough to minimize the effect of the B adaptor on the quality of DNA sequencing. It is clear that contribution of the B sequence can be further minimized by shortening of its size or even complete physical elimination of the terminal B sequence from the ends of amplified DNA templates. The latter can be achieved by a) by a limited trimming of DNA samples after PCR with 5' exonuclease (λ exonuclease, or T7 gene 6 exonuclease); and/or b) by incorporation of the dU nucleotide or a ribonucleotide into the 3' portion of the B primer sequence and degradation of the B sequence using dU-glycosylase and/or alkaline hydrolysis, respectively.

E. Applications of the PENTAmer Chromosome Walking Technology

1. Filling Gaps in Genome Sequencing Projects

Figure 18:
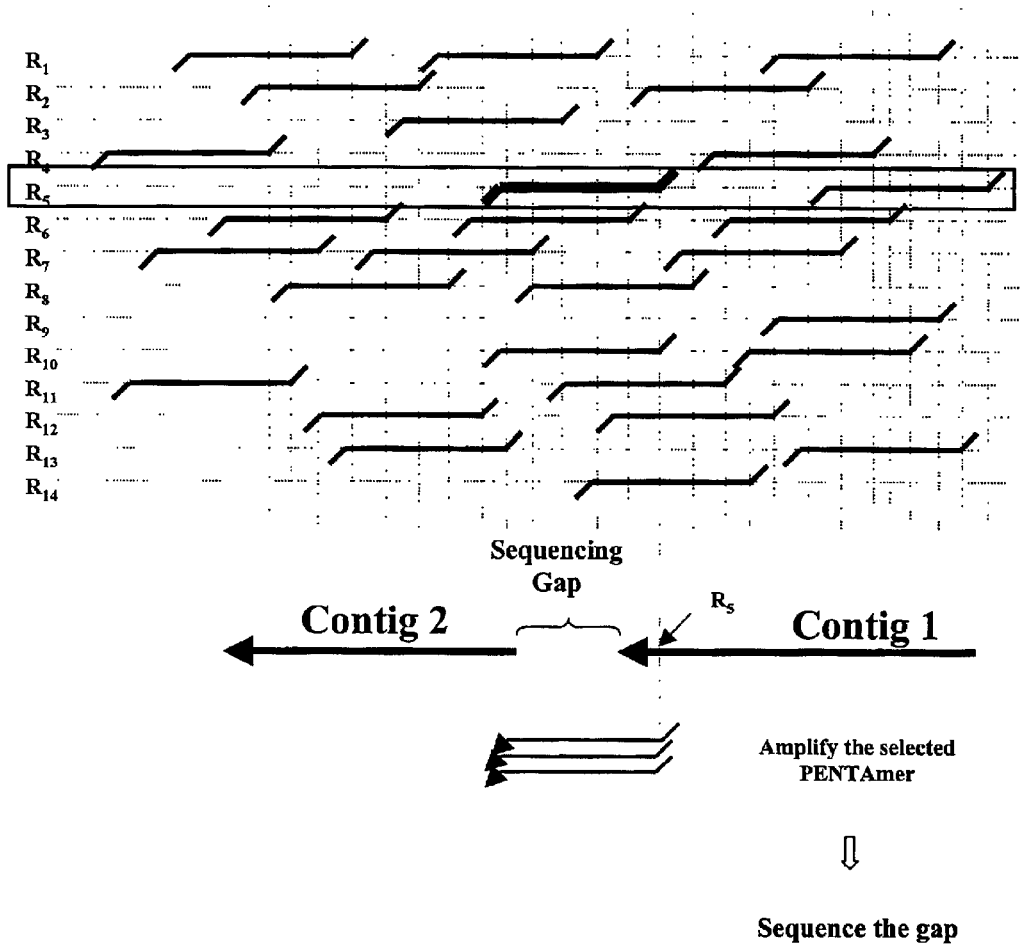
FIG. 18 illustrates sequencing gaps in a genome, such as a bacterial genome, using primary PENTAmer libraries.

It is obvious that the PENTAmer walking method described herein can be directly applied to fill gaps left after the shotgun phase. Usually, there are about 200–300 gaps in a bacterial sequencing project following 6–7 time redundancy sequencing. The human genome project currently has about 150,000 gaps. FIG. 18 illustrates the sequencing of gaps in a genome, such as a bacterial genome, using primary PENTAmer libraries.

2. 1–2 Time Redundancy Genomic Sequencing

The PENTAmer walking technology can be used to sequence bacterial genomes with a minimal redundancy. For example, in a first phase the genome can be sequenced randomly with 1 time redundancy and then finished using PENTAmer library. Because the library preparation is cheap, the cost would mostly be determined by the cost of one sequence-specific oligonucleotide, which is about $2–3 for a 24-mer. That means that at about 600 bases obtained at each step, the oligo cost per base is going to be 0.5 cent plus additional 0.5–1 cent per base for routine sequencing operation.

3. Sequencing Unculturable Microorganisms

The fact that the bacterial PENTAmer library can be diluted up to 1000 times, amplified and used for recovery DNA sequence information suggests that it is suitable for making libraries from a small amount of starting material, for example, unculturable bacteria or when there are other factors limiting the amount of DNA.

4. Sequencing Mixtures of Microorganisms

To the level the technology is applied to sequence more complex genomes, the PENTAmer libraries can be prepared from a complex mixture of different microorganisms. In this case, the walking process will allow (with some limitations) sequence of individual genomes within a mix with other DNA.

Figure 19:
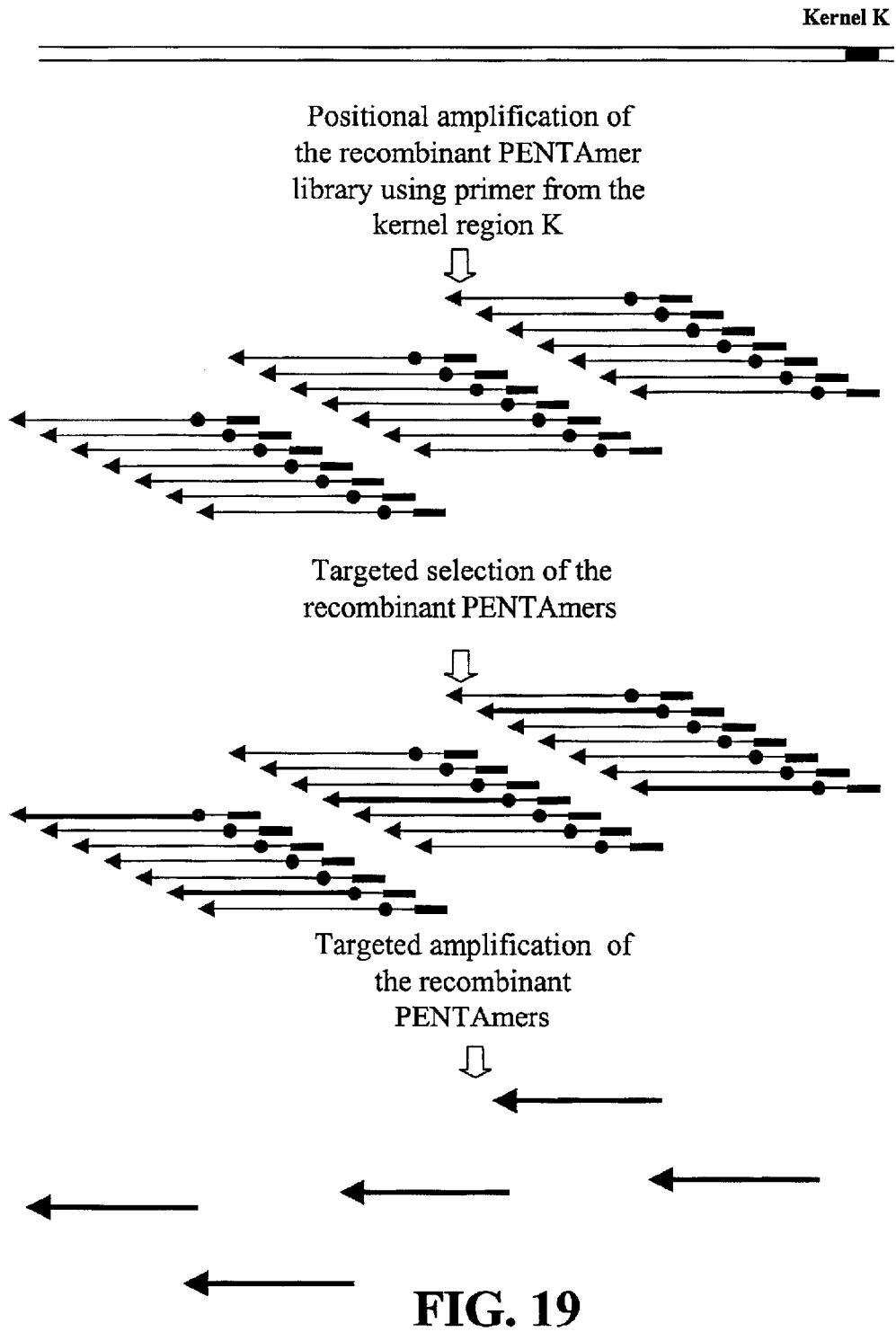
FIG. 19 demonstrates positional genome walking by targeted PENTAmer amplification.

Thus, as described in the previous sections, the fundamental nature of the present invention is illustrated in FIG. 19, wherein positional genome walking occurs by targeted PENTAmer amplification.

The next sections provide a brief overview of materials and techniques that a person of ordinary skill would deem important to the practice of the invention. These sections are followed by a more detailed description of the various embodiments of the invention.

III. Nucleic Acids

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA must be transported into the cytoplasm for the process of translation, which converts the code of the mRNA into a sequence of amino acids to form protein. In order to direct transport into the cytoplasm, the 3' ends of mRNA molecules are post-transcriptionally modified by addition of several adenylate residues to form the "polyA" tail. This characteristic modification distinguishes gene expression products destined to make protein from other molecules in the cell, and thereby provides one means for detecting and monitoring the gene expression activities of a cell.

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s)

towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

IV. Restriction Enzymes

Restriction-enzymes recognize specific short DNA sequences four to eight nucleotides long (see Table I), and cleave the DNA at a site within this sequence. In the context of the present invention, restriction enzymes are used to cleave DNA molecules at sites corresponding to various restriction-enzyme recognition sites. The site may be specifically modified to allow for the initiation of the PENT reaction. In another embodiment, if the sequence of the recognition site is known primers can be designed comprising nucleotides corresponding to the recognition sequences. These primers, further comprising PENT initiation sites may be ligated to the digested DNA.

Restriction-enzymes recognize specific short DNA sequences four to eight nucleotides long (see Table I), and cleave the DNA at a site within this sequence. In the context of the present invention, restriction enzymes are used to cleave cDNA molecules at sites corresponding to various restriction-enzyme recognition sites. Frequently cutting enzymes, such as the four-base cutter enzymes, are preferred as this yields DNA fragments that are in the right size range for subsequent amplification reactions. Some of the preferred four-base cutters are NlaIII, DpnII, Sau3AI, Hsp92II, MboI, NdeII, Bsp1431, Tsp509 I, HhaI, HinP1I, HpaII, MspI, Taq alphaI, MaeII or K2091.

As the sequence of the recognition site is known (see list below), primers can be designed comprising nucleotides corresponding to the recognition sequences. If the primer sets have in addition to the restriction recognition sequence, degenerate sequences corresponding to different combinations of nucleotide sequences, one can use the primer set to amplify DNA fragments that have been cleaved by the particular restriction enzyme. The list below exemplifies the currently known restriction enzymes that may be used in the invention.

TABLE I

RESTRICTION ENZYMES

| Enzyme Name | Recognition Sequence |
| --- | --- |
| AatII | GACGTC |
| Acc65I | GGTACC |
| AccI | GTMKAC |
| AciI | CCGC |
| AclI | AACGTT |
| AfeI | AGCGCT |
| AflII | CTTAAG |
| AflIII | ACRYGT |
| AgeI | ACCGGT |
| AhdI | GACNNNNNGTC |
| AluI | AGCT |
| AlwI | GGATC |
| AlwNI | CAGNNNCTG |
| ApaI | GGGCCC |
| ApaLI | GTGCAC |
| ApoI | RAATTY |
| AscI | GGCGCGCC |
| AseI | ATTAAT |
| AvaI | CYCGRG |
| AvaII | GGWCC |
| AvrII | CCTAGG |
| BaeI | NACNNNNGTAPyCN |
| BamHI | GGATCC |
| BanI | GGYRCC |
| BanII | GRGCYC |
| BbsI | GAAGAC |
| BbvI | GCAGC |
| BbvCI | CCTCAGC |
| BcgI | CGANNNNNNTGC |
| BciVI | GTATCC |
| BclI | TGATCA |
| BfaI | CTAG |
| BglI | GCCNNNNNGGC |
| BglII | AGATCT |
| BlpI | GCTNAGC |
| BmrI | ACTGGG |
| BpmI | CTGGAG |
| BsaAI | YACGTR |
| BsaBI | GATNNNNATC |
| BsaHI | GRCGYC |
| BsaI | GGTCTC |
| BsaJI | CCNNGG |
| BsaWI | WCCGGW |
| BseRI | GAGGAG |
| BsgI | GTGCAG |
| BsiEI | CGRYCG |
| BsiHKAI | GWGCWC |
| BsiWI | CGTACG |
| BslI | CCNNNNNNNGG |
| BsmAI | GTCTC |
| BsmBI | CGTCTC |
| BsmFI | GGGAC |
| BsmI | GAATGC |
| BsoBI | CYCGRG |
| Bsp1286I | GDGCHC |
| BspDI | ATCGAT |
| BspEI | TCCGGA |
| BspHI | TCATGA |
| BspMI | ACCTGC |
| BsrBI | CCGCTC |
| BsrDI | GCAATG |
| BsrFI | RCCGGY |
| BsrGI | TGTACA |
| BsrI | ACTGG |
| BssHII | GCGCGC |
| BssKI | CCNGG |
| Bst4CI | ACNGT |
| BssSI | CACGAG |
| BstAPI | GCANNNNTGC |
| BstBI | TTCGAA |

TABLE I-continued

RESTRICTION ENZYMES

| Enzyme Name | Recognition Sequence |
|---|---|
| BstEII | GGTNACC |
| BstF5I | GGATGNN |
| BstNI | CCWGG |
| BstUI | CGCG |
| BstXI | CCANNNNNNTGG |
| BstYI | RGATCY |
| BstZ17I | GTATAC |
| Bsu36I | CCTNAGG |
| BtgI | CCPuPyGG |
| BtrI | CACGTG |
| Cac8I | GCNNGC |
| ClaI | ATCGAT |
| DdeI | CTNAG |
| DpnI | GATC |
| DpnII | GATC |
| DraI | TTTAAA |
| DraIII | CACNNNGTG |
| DrdI | GACNNNNNNGTC |
| EaeI | YGGCCR |
| EagI | CGGCCG |
| EarI | CTCTTC |
| EciI | GGCGGA |
| EcoNI | CCTNNNNNAGG |
| EcoO109I | RGGNCCY |
| EcoRI | GAATTC |
| EcoRV | GATATC |
| FauI | CCCGCNNNN |
| Fnu4HI | GCNGC |
| FokI | GGATG |
| FseI | GGCCGGCC |
| FspI | TGCGCA |
| HaeII | RGCGCY |
| HaeIII | GGCC |
| HgaI | GACGC |
| HhaI | GCGC |
| HincII | GTYRAC |
| HindIII | AAGCTT |
| HinfI | GANTC |
| HinP1I | GCGC |
| HpaI | GTTAAC |
| HpaII | CCGG |
| HphI | GGTGA |
| KasI | GGCGCC |
| KpnI | GGTACC |
| MboI | GATC |
| MboII | GAAGA |
| MfeI | CAATTG |
| MluI | ACGCGT |
| MlyI | GAGTCNNNNN |
| MnlI | CCTC |
| MscI | TGGCCA |
| MseI | TTAA |
| MslI | CAYNNNNRTG |
| MspAlI | CMGCKG |
| MspI | CCGG |
| MwoI | GCNNNNNNNGC |
| NaeI | GCCGGC |
| NarI | GGCGCC |
| NciI | CCSGG |
| NcoI | CCATGG |
| NdeI | CATATG |
| NgoMIV | GCCGGC |
| NheI | GCTAGC |
| NlaIII | CATG |
| NlaIV | GGNNCC |
| NotI | GCGGCCGC |
| NruI | TCGCGA |
| NsiI | ATGCAT |
| NspI | RCATGY |
| PacI | TTAATTAA |
| PaeR7I | CTCGAG |
| PciI | ACATGT |
| PflFI | GACNNNGTC |
| PflMI | CCANNNNNTGG |
| PleI | GAGTC |

TABLE I-continued

RESTRICTION ENZYMES

| Enzyme Name | Recognition Sequence |
|---|---|
| PmeI | GTTTAAAC |
| PmlI | CACGTG |
| PpuMI | RGGWCCY |
| PshAI | GACNNNNGTC |
| PsiI | TTATAA |
| PspGI | CCWGG |
| PspOMI | GGGCCC |
| PstI | CTGCAG |
| PvuI | CGATCG |
| PvuII | CAGCTG |
| RsaI | GTAC |
| RsrII | CGGWCCG |
| SacI | GAGCTC |
| SacII | CCGCGG |
| SalI | GTCGAC |
| SapI | GCTCTTC |
| Sau3AI | GATC |
| Sau96I | GGNCC |
| SbfI | CCTGCAGG |
| ScaI | AGTACT |
| ScrFI | CCNGG |
| SexAI | ACCWGGT |
| SfaNI | GCATC |
| SfcI | CTRYAG |
| SfiI | GGCCNNNNNGGCC |
| SfoI | GGCGCC |
| SgrAI | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| TaqI | TCGA |
| TfiI | GAWTC |
| TliI | CTCGAG |
| TseI | GCWGC |
| Tsp45I | GTSAC |
| Tsp509I | AATT |
| TspRI | CAGTG |
| Tth111I | GACNNNGTC |
| XbaI | TCTAGA |
| XcmI | CCANNNNNNNNNTGG |
| XhoI | CTCGAG |
| XmaI | CCCGGG |
| XmnI | GAANNNNTTC |

Furthermore, a skilled artisan recognizes that it may be useful in the present invention to selectively render particular restriction enzyme sites uncleavable, such as by methylation of the recognition site prior to exposure to certain methylation-sensitive restriction enzymes. A skilled artisan recognizes that, for example, the dam and dcm genes of *E. coli* encode gene products which are methylases that methylate a nucleic acid in their specific recognition sequence. Some enzymes will not cleave methylated sites, whereas other enzymes, such as Dpn I, have a requirement for methylation at the recognition site. Examples of different classes of methylation requirements for specific enzymes are in Table II as follows:

TABLE II

CpG METHYLATION AND ENZYME CLEAVAGE

Cleavage Blocked at All Sites

| | | | | | | | |
|---|---|---|---|---|---|---|---|
| AatII | GACGTC | BsrFI | RCCGGY | HaeII | RGCGCY | NruI | TCGCGA |
| AciI | CCGC | BSSHII | GCGCGC | HgaI | GACGC | PmlI | CACGTG |
| AgeI | ACCGGT | BSTBI | TTCGAA | HhaI | GCGC | Psp1406I | AACGTT |
| AhaII | GRCGYC | BSTUI | CGCG | HinP1 I | GCGC | PvuI | CGATCG |
| AscI | GGCGCGCC | Cfr10I | RCCGGY | HpaII | CCGG | RsrII | CGGWCCG |
| AvaI | CYCGRG | ClaI | ATCGAT | KasI | GGCGCC | SacII | CGGCGG |
| BsaAI | YACGTR | EagI | CGGCCG | MluI | ACGCGT | SalI | GTCGAC |
| BsaHI | GRCGYC | Eco47III | AGCGCT | NaeI | GCCGGC | SmaI | CCCGGG |
| BsiEI | CGRYCG | Esp3I | CGTCTC(¼) | NarI | GGCGCC | SnaBI | TACGTA |
| BsiWI | CGTACG | FseI | GGCCGGCC | NgoM IV | GCCGGC | TaiI | ACGT |
| BspDI | ATCGAT | FspI | TGCGCA | Not I | GCGGCCGC | XhoI | CTCGAG |

Cleavage Blocked Only at Sites with Overlapping CG

| | | | | | | | |
|---|---|---|---|---|---|---|---|
| AccI | GTMKAC | BanI[3] | GGYRCC | Bsp120I | GGGCCC | NheI | GCTAGC |
| Acc65I | GGTACC | BsaB I[2] | GATN4ATC | Bst1 107I | GTATAC | RsaI[3] | GTAC |
| Alw26I | GTCTC | BsgI | GTGCAG | DrdI[1] | GACN6GTC | PshAI[3] | GACNNNNGTC |
| ApaI | GGGCCC | BslI | CCN7GG | EaeI | YGGCCR | Sau3AI | GATC |
| ApaLI | GTGCAC | BsmAI | GTCTC | Ecl136II | GAGCTC | Sau96I | GGNCC |
| AvaII | GGWCC | BsoFI[1] | GCNGC | HpaI[3] | GTTAAC | | |

Cleavage Not Blocked at Sites with Overlapping CG

| | | | | | | | |
|---|---|---|---|---|---|---|---|
| BamHI | GGATCC | BsrBI[2] | GAGCGG | EcoR V | GATATC | PmeI | GTTTAAAC |
| BanII | GRGCYC | BstEII | GGTNACC | FokI | GGATG | SacI | GAGCTC |
| BbsI | GAAGAC | BstYI | RGTACY | HaeIII | GGCC | StaNI | GCATG |
| BsaJI | CCNNGG | Csp6I | GTAC | HglAI | GWGCWC | SphI | GCATGC |
| BsaWI | WCCGGW | Eam1105I | GACN5GTC | HphI | GGTGA | TaqI | TCGA |
| BsmI | GATTGC | EarI | CCTCTTC | KpnI | GGTACC | TfiI | GAWTC |
| Bsp1286I | GDGCHC | EcoO1091 | RGGNCCY | MspI | CCGG | Tth111I | GACN3GTC |
| BspEI[2] | TCCGGA | EcoRI | GAATTC | PaeR7I | CTCGAG | XmaI | CCCGGG |
| BspMI | ACCTGC | | | | | | |

Examples of restriction enzyme sites sensitive to Dam and Dcm methylation in particular are in Table III as follows:

TABLE III

DAM AND DCM METHYLATION

Dam Methylation: G$^m$ATC
Blocked by Overlapping Dam:

| | |
|---|---|
| AlwI | GGATC |
| BclI | TGATCA |
| BsaB I | GAT<u>C</u>NNNATC |
| BspD I | ATCGATC |
| BspE I | TCCGGATC |
| BspH I | TCATGATC |
| ClaI | ATCGATC |
| Dpn II | GATC |
| HphI | GGTGATC |
| MboI | GATC |
| MboII | GAAGATC |
| NruI | TCGCGATC |
| TaqI | TCGATC |
| XbaI | TCTAGATC |

Not Blocked by Overlapping Dam:

| | |
|---|---|
| BamHI | GGATCC |
| BglII | AGATCT |
| BspMII | TCCGGATC |
| BstY I | (A/G)GATC(C/T) |
| PvuI | CGATCG |
| Sau3A I | GATC |

Dcm Methylation: C$^m$C(A/T)GG
Blocked by Overlapping Dcm:

| | |
|---|---|
| ACC65I | GGTACC(A/T)GG |
| AlwNI | CAGNN<u>C</u>CTGG |
| ApaI | GGGCCC(A/T)GG |
| AvaII | GG(A/T)CC(A/T)GG |
| BalI | TGGCCAGg |
| BpmI | CCTGGAG |
| BslI | CC(A/T)GGNNNNGG |
| Bsp120I | GGGCCC(A/T)GG |
| BssK I | CC(A/T)GG |
| EaeI | (C/T)GGCC<u>A</u>GG |
| EcoO109I | (A/G)GGNCC<u>T</u>GG |
| EcoRII | CC(A/T)GG |
| MscI | TGGCCAGG |
| PflM I | CCA<u>GG</u>NNNTGG |
| PpuM I | (A/G)GG(A/T)CC<u>T</u>GG |
| Sau96 I | GGNCC(A/T)GG |
| ScrF I | CC(A/T)GG |
| SexA I | ACC(A/T)GGT |
| Sfi I | GGCC(A/T)<u>GG</u>NNGGCC |
| StuI | AGGCCTGG |

Not Blocked by Overlapping Dcm

| | |
|---|---|
| BanII | G(A/G)GC<u>C</u>C(A/T)GG |
| BglI | GCC(A/T)<u>GG</u>NNGGC |
| BsaJI | CC(A/T)GGG |
| Bsp 1286I | G(A/G/T)GC<u>C</u>C(A/T)GG |
| BstNI | CC(A/T)GG |
| BstEII | GGTNACC(A/T)GG |
| EheI | GGCGCC(A/T)GG |
| HaeIII | GGCC(A/T)GG |
| KpnI | GGTACC(A/T)GG |
| NarI | GGCGCC(A/T)GG |
| SfiI | GGCCNNNNNGGCC(A/T)GG |

Other examples of methylation-sensitive enzymes, which may not be listed here, are obtainable by a skilled artisan.

V. Other Enzymes

Other enzymes that may be used in conjunction with the invention include nucleic acid modifying enzymes listed in the following tables.

TABLE IV

POLYMERASES AND REVERSE TRANSCRIPTASES

Thermostable DNA Polymerases:

OmniBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Tfl DNA Polymerase
Tli DNA Polymerase
Tth DNA Polymerase
DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase
Reverse Transcriptases:

AMV Reverse Transcriptase
M-MLV Reverse Transcriptase

TABLE V

DNA/RNA MODIFYING ENZYMES

Ligases:

T4 DNA Ligase
Kinases

T4 Polynucleotide Kinase

VI. DNA Polymerases

In the context of the present invention it is generally contemplated that the DNA polymerase will retain 5'–3' exonuclease activity. Nevertheless, it is envisioned that the methods of the invention could be carried out with one or more enzymes where multiple enzymes combine to carry out the function of a single DNA polymerase molecule retaining 5'–3' exonuclease activity. Effective polymerases which retain 5'–3' exonuclease activity include, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, Vent DNA polymerase, thermosequenase and wild-type or modified T7 DNA polymerases. In preferred embodiments, the effective polymerase is *E. coli* DNA polymerase I, *M. tuberculosis* DNA polymerase I or Taq DNA polymerase.

Where the break in the substantially double stranded nucleic acid template is a gap of at least a base or nucleotide in length that comprises, or is reacted to comprise, a 3' hydroxyl group, the range of effective polymerases that may be used is even broader. In such aspects, the effective polymerase may be, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, T4 DNA polymerase, vent DNA polymerase, thermosequenase or a wild-type or modified T7 DNA polymerase. In preferred aspects, the effective polymerase is *E. coli* DNA polymerase I, M tuberculosis DNA polymerase I, Taq DNA polymerase or T4 DNA polymerase.

VII. Hybridization

PENTAmer synthesis requires the use of primers which hybridize to specific sequences. Further, PENT reaction products may be useful as probes in hybridization analysis. The use of a probe or primer of between about 13 and 100 nucleotides, preferably between about 17 and 100 nucleotides in length, or in some aspects of the invention up to about 1–2 Kb or more in length, allows the formation of a duplex molecule that is both stable and selective. Molecules having complementary sequences over contiguous stretches greater than about 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Depending on the application envisioned, one would desire to employ varying conditions of hybridization to achieve varying degrees of selectivity of the probe or primers for the target sequence. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

VIII. Amplification of Nucleic Acids

Nucleic acids useful as templates for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTPs) and a thermostable polymerase, such as, for example, Taq (*Thermus aquaticus*) DNA polymerase. In a series (typically 30–35) of temperature cycles, the target DNA is repeatedly denatured (around 90° C.), annealed to the primers (typically at 50–60° C.) and a daughter strand extended from the primers (72° C.). As the daughter strands are created they act as templates in subsequent cycles. Thus the template region between the two primers is amplified exponentially, rather than linearly.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

A. LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

B. Qbeta Replicase

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

C. Isothermal Amplification

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Such an amplification method is described by Walker et al. 1992, incorporated herein by reference.

D. Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

E. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

F. Transcription-Based Amplification

Other nucleic acid amplification procedures include transcription-based amplification systems (TAS), including nucleic acid sequence based amplification (NASBA) and 3SR, Kwoh et al., 1989; PCT Patent Application WO 88/10315 et al., 1989, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

G. Other Amplification Methods

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Miller et al, PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "race" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

IX. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

X. Separation and Quantitation Methods

Following amplification, it may be desirable to separate the amplification products of several different lengths from each other and from the template and the excess primer for the purpose analysis or more specifically for determining whether specific amplification has occurred.

A. Gel Electrophoresis

In one embodiment, amplification products are separated by agarose, agarose-acrylamide or polyacrylamide gel electrophoresis using standard methods (Sambrook et al., 1989).

Separation by electrophoresis is based upon the differential migration through a gel according to the size and ionic charge of the molecules in an electrical field. High resolution techniques normally use a gel support for the fluid phase. Examples of gels used are starch, acrylamide, agarose or mixtures of acrylamide and agarose. Frictional resistance produced by the support causes size, rather than charge alone, to become the major determinant of separation. Smaller molecules with a more negative charge will travel faster and further through the gel toward the anode of an electrophoretic cell when high voltage is applied. Similar molecules will group on the gel. They may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer. The gel may be a single concentration or gradient in which pore size decreases with migration distance. In SDS gel electrophoresis of proteins or electrophoresis of polynucleotides, mobility depends primarily on size and is used to determined molecular weight. In pulse field electrophoresis, two fields are applied alternately at right angles to each other to minimize diffusion mediated spread of large linear polymers.

Agarose gel electrophoresis facilitates the separation of DNA or RNA based upon size in a matrix composed of a highly purified form of agar. Nucleic acids tend to become oriented in an end on position in the presence of an electric field. Migration through the gel matrices occurs at a rate inversely proportional to the $\log_{10}$ of the number of base pairs (Sambrook et al., 1989).

Polyacrylamide gel electrophoresis (PAGE) is an analytical and separative technique in which molecules, particularly proteins, are separated by their different electrophoretic mobilities in a hydrated gel. The gel suppresses convective mixing of the fluid phase through which the electrophoresis takes place and contributes molecular sieving. Commonly carried out in the presence of the anionic detergent sodium dodecylsulphate (SDS). SDS denatures proteins so that noncovalently associating sub unit polypeptides migrate independently and by binding to the proteins confers a net negative charge roughly proportional to the chain weight.

B. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

C. Microfluidic Techniques

Microfluidic techniques include separation on a platform such as microcapillaries, designed by ACLARA BioSciences Inc., or the LABCHIP™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 and 5,296,375, discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

D. Capillary Electrophoresis

In some embodiments, it may be desirable to provide an additional, or alternative means for analyzing the amplified genes. In these embodiment, micro capillary arrays are contemplated to be used for the analysis.

Microcapillary array electrophoresis generally involves the use of a thin capillary or channel that may or may not be filled with a particular separation medium. Electrophoresis of a sample through the capillary provides a size based separation profile for the sample. The use of microcapillary electrophoresis in size separation of nucleic acids has been reported in, for example, Woolley and Mathies, 1994. Microcapillary array electrophoresis generally provides a rapid method for size-based sequencing, PCR™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobsen et al., 1994; Effenhauser et al., 1994; Harrison et al., 1993; Effenhauser et al., 1993; Manz et al., 1992; and U.S. Pat. No. 5,904,824, here incorporated by reference. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

E. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the known in the art can be found summarized in Methods in Enzymology, Vol. 193: "Mass Spectrometry" (McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include Schram, 1990 and Crain, 1990 here incorporated by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al. 1987).

Two ionization/desorption techniques are electrospray/ionspray (ES) and matrix-assisted laser desorption/ionization (MALDI). ES mass spectrometry was introduced by Fenn, 1984; PCT Application No. WO 90/14148 and its applications are summarized in review articles, for example, Smith 1990 and Ardrey, 1992. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp 1990. Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams, 1989). More recently, this the use of infra red lasers (IR) in this technique (as opposed to UV-lasers) has been shown to provide mass spectra of larger nucleic acids such as, synthetic DNA, restriction enzyme fragments of plasmid DNA, and RNA transcripts up to a size of 2180 nucleotides (Berkenkamp, 1998). Berkenkamp also describe how DNA and RNA samples can be analyzed by limited sample purification using MALDI-TOF IR.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

F. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, 1948. The distance between donor and acceptor dyes at which energy transfer efficiency is 50% is referred to as the Forster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992. Academic Press, Inc., pgs. 311–352).

Homogeneous methods employing energy transfer or other mechanisms of fluorescence quenching for detection of nucleic acid amplification have also been described. Higuchi (1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee, 1993, discloses a real-time detection method in which a doubly-labeled detector probe is cleaved in a target amplification-specific manner during PCR™. The detector probe is hybridized downstream of the amplification primer so that the 5'–3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/Texas Red™. (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and maybe routinely used to link the donor and acceptor dyes at their respective sites in the detector nucleic acid.

G. Chip Technologies

DNA arrays and gene chip technology provides a means of rapidly screening a large number of DNA samples for their ability to hybridize to a variety of single stranded DNA probes immobilized on a solid substrate. Specifically contemplated are chip-based DNA technologies such as those described by Hacia et al., (1996) and Shoemaker et al. (1996). These techniques involve quantitative methods for analyzing large numbers of genes rapidly and accurately The technology capitalizes on the complementary binding properties of single stranded DNA to screen DNA samples by hybridization. Pease et al., 1994; Fodor et al., 1991. Basically, a DNA array or gene chip consists of a solid substrate upon which an array of single stranded DNA molecules have been attached. For screening, the chip or array is contacted with a single stranded DNA sample which is allowed to hybridize under stringent conditions. The chip or array is then scanned to determine which probes have hybridized. In the context of this embodiment, such probes could include synthesized oligonucleotides, cDNA, genomic DNA, yeast artificial chromosomes (YACs), bacterial artificial chromosomes (BACs), chromosomal markers or other constructs a person of ordinary skill would recognize as adequate to demonstrate a genetic change.

A variety of gene chip or DNA array formats are described in the art, for example U.S. Pat. Nos. 5,861,242 and 5,578,832 which are expressly incorporated herein by reference. A means for applying the disclosed methods to the construction of such a chip or array would be clear to one of ordinary skill in the art. In brief, the basic structure of a gene chip or array comprises: (1) an excitation source; (2) an array of probes; (3) a sampling element; (4) a detector; and (5) a signal amplification/treatment system. A chip may also include a support for immobilizing the probe.

In particular embodiments, a target nucleic acid may be tagged or labeled with a substance that emits a detectable signal; for example, luminescence. The target nucleic acid may be immobilized onto the integrated microchip that also supports a phototransducer and related detection circuitry. Alternatively, a gene probe may be immobilized onto a membrane or filter which is then attached to the microchip or to the detector surface itself. In a further embodiment, the immobilized probe may be tagged or labeled with a substance that emits a detectable or altered signal when combined with the target nucleic acid. The tagged or labeled species may be fluorescent, phosphorescent, or otherwise luminescent, or it may emit Raman energy or it may absorb energy. When the probes selectively bind to a targeted species, a signal is generated that is detected by the chip. The signal may then be processed in several ways, depending on the nature of the signal.

The DNA probes may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860 both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen, et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents. (Running, et al., 1990); Newton, et al. (1993)). When immobilized onto a substrate, the probes are stabilized and therefore may be used repeatedly. In general terms, hybridization is performed on an immobilized nucleic acid target or a probe molecule is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

Binding of the probe to a selected support may be accomplished by any of several means. For example, DNA is commonly bound to glass by first silanizing the glass surface, then activating with carbodimide or glutaraldehyde. Alternative procedures may use reagents such as 3-glycidoxypropyltrimethoxysilane (GOP) or aminopropyl-trimethoxysilane (APTS) with DNA linked via amino linkers incorporated either at the 3' or 5' end of the molecule during DNA synthesis. DNA may be bound directly to membranes using ultraviolet radiation. With nitrocellous membranes, the DNA probes are spotted onto the membranes. A UV light source (Stratalinker, from Stratagene, La Jolla, Calif.) is used to irradiate DNA spots and induce cross-linking. An alternative method for cross-linking involves baking the spotted membranes at 80° C. for two hours in vacuum.

Specific DNA probes may first be immobilized onto a membrane and then attached to a membrane in contact with a transducer detection surface. This method avoids binding the probe onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

XI. Identification Methods

Amplification products must be visualized in order to confirm amplification of the target-gene(s) sequences. One typical visualization method involves staining of a gel with for example, a fluorescent dye, such as ethidium bromide or Vista Green and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly, using a nucleic acid probe. Following separation of amplification products, a labeled, nucleic acid probe is brought into contact with the amplified gene(s) sequence. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of TAQMAN™ and MOLECULAR BEACON™ probes. In still other embodiments, solid-phase capture methods combined with a standard probe may be used as well.

The type of label incorporated in PCR™ products is dictated by the method used for analysis. When using capillary electrophoresis, microfluidic electrophoresis, HPLC, or LC separations, either incorporated or intercalated fluorescent dyes are used to label and detect the PCR™ products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the PCR™ can be labeled with a fluorophore, a chromophore or a radioisotope, or by associated enzymatic reaction. Enzymatic detection involves binding an enzyme to primer, e.g., via a biotin:avidin interaction, following separation of PCR™ products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If PCR™ products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, and some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

XII. Sequencing

It is envisioned that amplified product will commonly be sequenced for further identification. Sanger dideoxy-termination sequencing is the means commonly employed to determine nucleotide sequence. The Sanger method employs a short oligonucleotide or primer that is annealed to a single-stranded template containing the DNA to be sequenced. The primer provides a 3' hydroxyl group which allows the polymerization of a chain of DNA when a polymerase enzyme and dNTPs are provided. The Sanger method is an enzymatic reaction that utilizes chain-terminating dideoxynucleotides (ddNTPs). ddNTPs are chain-terminating because they lack a 3'-hydroxyl residue which prevents formation of a phosphodiester bond with a succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP.

Although a variety of polymerases may be used, the use of a modified T7 DNA polymerase (SEQUENASE™) was a significant improvement over the original Sanger method (Sambrook et al., 1988; Hunkapiller, 1991). T7 DNA polymerase does not have any inherent 5'–3' exonuclease activity and has a reduced selectivity against incorporation of ddNTP. However, the 3'–5' exonuclease activity leads to degradation of some of the oligonucleotide primers. SEQUENASE™ is a chemically-modified T7 DNA polymerase that has reduced 3' to 5' exonuclease activity (Tabor et al., 1987). SEQUENASE™ version 2.0 is a genetically engineered form of the T7 polymerase which completely lacks 3' to 5' exonuclease activity. SEQUENASE™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures during electrophoresis are alleviated. In contrast, does not incorporate these analogs as efficiently.

The use of Taq DNA polymerase and mutants thereof is a more recent addition to the improvements of the Sanger method (U.S. Pat. No. 5,075,216). Taq polymerase is a thermostable enzyme which works efficiently at 70–75° C. The ability to catalyze DNA synthesis at elevated temperature makes Taq polymerase useful for sequencing templates which have extensive secondary structures at 37° C. (the standard temperature used for Klenow and SEQUENASE™ reactions). Taq polymerase, like SEQUENASE™, has a high degree of processivity and like Sequenase 2.0, it lacks 3' to 5' nuclease activity. The thermal stability of Taq and related enzymes (such as Tth and THERMOSEQUENASE™) provides an advantage over T7 polymerase (and all mutants thereof) in that these thermally stable enzymes can be used for cycle sequencing which amplifies the DNA during the sequencing reaction, thus allowing sequencing to be performed on smaller amounts of DNA. Optimization of the use of Taq in the standard Sanger Method has focused on modifying Taq to eliminate the intrinsic 5'–3' exonuclease activity and to increase its ability to incorporate ddNTPs to reduce incorrect termination due to secondary structure in the single-stranded template DNA (EP 0 655 506 B1). The introduction of fluorescently labeled nucleotides has further allowed the introduction of automated sequencing which further increases processivity.

XIII. DNA Immobilization

Immobilization of the DNA may be achieved by a variety of methods involving either non-covalent or covalent interactions between the immobilized DNA comprising an anchorable moiety and an anchor. In a preferred embodiment of the invention, immobilization consists of the non-covalent coating of a solid phase with streptavidin or avidin and the subsequent immobilization of a biotinylated polynucleotide (Holmstrom, 1993). It is further envisioned that immobilization may occur by precoating a polystyrene or glass solid phase with poly-L-Lys or poly L-Lys, Phe, followed by the covalent attachment of either amino- or sulfhydryl-modified polynucleotides using bifunctional crosslinking reagents (Running, 1990 and Newton, 1993).

Immobilization may also take place by the direct covalent attachment of short, 5'-phosphorylated primers to chemically modified polystyrene plates ("Covalink" plates, Nunc)

Rasmussen, (1991). The covalent bond between the modified oligonucleotide and the solid phase surface is introduced by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid molecules in the presence of a salt or cationic detergent on a hydrophilic polystyrene solid support containing a hydrophilic moiety or on a glass solid support. The support is contacted with a solution having a pH of about 6 to about 8 containing the synthetic nucleic acid and a cationic detergent or salt. The support containing the immobilized nucleic acid may be washed with an aqueous solution containing a non-ionic detergent without removing the attached molecules.

Another commercially available method envisioned by the inventors to facilitate immobilization is the "Reacti-Bind.TM. DNA Coating Solutions" (see "Instructions—Reacti-Bind.TM. DNA Coating Solution" 1/1997). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND™" or Immobilon-AV Affinity Membrane (IAV, Millipore, Bedford, Mass.) are equally applicable to immobilize the respective fragment.

XIV. Analysis of Data

Gathering data from the various analysis operations will typically be carried out using methods known in the art. For example, microcapillary arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Scanning devices of this kind are described in U.S. Pat. Nos. 5,143,854 and 5,424,186.

Following the data gathering operation, the data will typically be reported to a data analysis operation. To facilitate the sample analysis operation, the data obtained by a reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, e.g., U.S. Pat. Nos. 4,683,194; 5,599,668; and 5,843,651, each of which is incorporated herein by reference.

XV. Plants

The term "plant," as used herein, refers to any type of plant. The inventors have provided below an exemplary description of some plants that may be used with the invention. However, the list is not in any way limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, Swiss chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fibre plants (cotton, flax, hemp, jute), lauraceae (cinnamon, camphor), or plants such as coffee, sugarcane, tea, and natural rubber plants.

Still other examples of plants include bedding plants such as flowers, cactus, succulents and ornamental plants, as well as trees such as forest (broad-leaved trees and evergreens, such as conifers), fruit, ornamental, and nut-bearing trees, as well as shrubs and other nursery stock.

XVI. Animals

The term "animal," as used herein, refers to any type of animal. The inventors have provided below an exemplary description of some animals that may be used with the invention. However, the list is not in any way limiting, as other types of animals will be known to those of skill in the art and could be used with the invention.

For the purpose of the instant invention, the term animal is expressly construed to include humans.

In addition to humans, other animals of importance in the context of the instant invention are those animals deemed of commercial relevance. Animals of commercial relevance specifically include domesticated species including companion and agricultural species.

XVII. Bacteria

The present invention is useful in sequencing the genome of bacteria. Bacteria is herein defined as a unicellular prokaryote. Examples include, but are not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans,* other viridans streptococci, peptostreptococci, other related species of streptococci, enterococci such as *Enterococcus faecalis, Enterococcus faecium,* Staphylococci, such as *Staphylococcus epidermidis, Staphylococcus aureus, Hemophilus influenzae,* pseudomonas species such as *Pseudomonas aeruginosa, Pseudomonas pseudomallei, Pseudomonas mallei,* brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi,* etc. *Listeria monocytogenes, Nocordia asteroides,* Bacteroides species, Actinomycetes species, *Treponema pallidum,* Leptospirosa species and related organisms. The invention may also be useful for determining genomic sequences of gram negative bacteria such as *Klebsiella pneumoniae, Escherichia coli,* Serratia species, Acinetobacter, *Francisella tularensis,* Enterobacter species, Bacteriodes and like.

Other bacteria species include *Bacteroides forsythus, Porphyromonas gingivalis, Prevotella intermedia* and *Prevotella nigrescens, Actinobacillus actinomycetemcomitana*, Actinomyces, *A. viscosus, A. naeslundii, Bacteroides forsythus, Streptococcus intermedius, Campylobacier rectus* and *Campylobacter jejuni*, Peptostreptococcus, *Eikenella corrondens, P. anaerobius*, Eubacterium, *P. micros, E. alactolyticum, E. brachy*, Fusobacterium, *F. alocis, F. nucleatum, Porphyromonas gingivalis*, Prevotella, *P. intermedia, P. nigrescens, Selenomonas sputigena*, Treponema, *T. denticola*, and *T. socranskii*.

Other bacterial species include Campylobacter species, such as Cryptosporidium, Giardia, Leptospira, Pasteurella, Proteus, Shigella, Vibrio species, such as *Vibrio cholerae, V. alginolyticus, V. fluvialis, V. mimicus, V. parahaemolyticus, V. vulnificus* and other Vibrio spp., *Salmonella typhimurium, S. typhi*, Proteus sp., *Yersinia enterocolitica, Vibrio parahaemo-lyticus, Acinetobacter calcoaceticus, Aeromonas hydrophila, A. sobria, A. caviae, C. coli, Chromobacterium violaceum*, Citrobacter spp., *Clostridium perfringens, Flavobacterium meninogsepticum, Francisella tularensis, Fusobacterium necrophorum, Legionella pneumophila* and other Legionella spp., *Morganella morganii, Mycobacterium tuberculosis, M. marinum* and other Mycobacterium spp., *Plesiomonas shigelloides, Salmonella enteritidis, S. montevideo* B, *S. typhimurium* and other Salmonella serotypes, *S. paratyphi* A and B, *S. typhi, Serratia marcesens, Enterobacter aerogenes, Proteus mirabills, Proteus vulgaris, Pseudomonas aeruginosa, Streptococcus faecalis, mycobactin, Clostridium botulinum, Streptococcus faecalis, Proteus vulgaris, Pseudomonas aeruginosa*, Enterobacteriaceae, *Yersinia pestis, Yersinia pseudotuberculosis, Stenotrophomonas maltophilia, burkholderia cepacia, Gardnerella vaginalis*, Bartonella spp., Hafnia spp., Buttlauxella, Cedecea, Ewingella, Providencia, *C. psittaci*, and *C. trachomatis*.

Bacterial plant pathogens include species of Agrobacteria (e.g., *Agaricus bisporus* (Lange) Imbach or *Agrobacterium tumefaciens*), Clavibacter, Corynebacterium, Erwinia (e.g., *Erwinia carotovora* subsp. *Carotovora*), Pseudomonas (e.g., *Pseudomonas tolaasii* Paine, *Pseudomonas solanacearum, Pseudomonas syringae* pv.) and Xanthomonas (e.g., *Xanthomonas campestris* pv. Malvacearum).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and Analysis of PENTAmer Library from *E. Coli* BamH I Complete Genomic Digest In the following examples, primary genomic PENTAmer library is defined as library produced from complete or partial restriction digest after ligation of nick-translation adaptor A from which a time-controlled nick-translation is performed, followed by ligation of nick-attaching adaptor B to the 3'-terminus of synthesized PENT product. Primary genomic libraries are highly representative since no amplification bias has been imposed on them.

This example describes a protocol for preparation of primary PENTAmer library from *E. coli* genomic DNA with upstream nick-translation BamH I compatible adaptor A and downstream nick-attaching adaptor B having randomized bases at the strand used to direct ligation at the 3' end of nick-translated PENT molecules.

Genomic DNA from *E. coli* MG-1655 is prepared by standard procedure. Ten micrograms of DNA are digested at 37° C. for 4 hours with 120 units of BamH I restriction enzyme (NEB) in total volume of 150 $\mu$l. The sample is split into two tubes, diluted twice with water, supplemented with 1× Shrimp Alkaline Phosphatase (SAP) buffer (Roche; Nutley, N.J.), and the DNA is dephosphorylated with 10 units of SAP (Roche; Nutley, N.J.) for 20 min at 37° C. SAP is heat-inactivated for 15 min at 65° C. and DNA is purified by extraction with equal volume of phenol:chloroform:isoamyl alcohol (25:24:1) followed by precipitation with ethanol. Digested DNA is dissolved in 50 $\mu$l of 10 mM Tris-HCl, pH 7.5.

The sample is mixed with 3 pmoles of pre-assembled BamH I nick-translation adaptor (adaptor A3 consisting of primers 11, 12, and 13), and ligation is carried out overnight at 16° C. with 1200 units of T4 ligase (NEB) in 60 $\mu$l volume. To remove ligase and excess free adaptor, the sample is extracted with equal volume of phenol:chloroform:isoamyl alcohol (25:24:1), supplemented with ¼ volume of QF buffer (final concentrations of 240 mM NaCl, 3% isopropanol, and 10 mM Tris-HCl, pH 8.5) in a volume of 400 $\mu$l and centrifuged at 200×g to a volume of approximately 100 $\mu$l. The sample is washed 3 times with 400 ml of TE-L buffer (10 mM Tris-HCl, 0.1 mM EDTA, pH 7.5) at 200×g and concentrated to a final volume of 80 $\mu$l.

TABLE VI

ADAPTOR STRUCTURES

Adaptor A3 (Bam HI, Sau 3AI)

(5') P     gatctgaggttgttgaagcgttuacccaautcgatuaggcaa N-C7 (3') (SEQ ID NO:29)
(3') N-C7   actccaacaacttc gcaaaugggtuaagcuaatccgtt Biotin (5') (SEQ ID NO:30)
Adaptor B1 (Poly N universal)

(5') P     aagtctgcaagatcatcgcggaaggtgacaaagactcgtatcgtaaNNNNc N-C7(3') (SEQ ID NO:31)
(3') N-C7   ttcagacgttctagtagcgccttccactgtttctgagcatagcatt-P(5') (SEQ ID NO:32)

wherein N-C7 = Amino C7 Blocking group
P = 5' phosphate

The purified sample is subjected to nick-translation with 20 units of wild type Taq polymerase in 1× Perkin Elmer (Norwalk, Conn.) PCR buffer buffer II containing 2 mM $MgCl_2$ and 200 mM of each dNTP for 5 min at 50° C. The reaction is stopped by addition of 5 μl of 0.5 M EDTA pH 8.0, and products are analyzed on 6% TBE-urea gel (Novex; San Diego, Calif.) after staining with SYBR GOLD™.

To increase representativity of single-stranded PENT molecules bound to streptavidin beads and to prevent their reassociation with the strand used as template for nick-translation in the region of the adaptor, an oligonucleotide complementary to the template strand spanning the entire adaptor sequence (primer 15) is added at a final concentration of 0.8 mM, and the sample is denatured by boiling at 100° C. for 3 min and cooling on ice for 5 min. Eight hundred micrograms of streptavidin-coated DYNA-BEADS™ M-280 (Dynal) are prewashed with TE-L buffer and resuspended in 2×BW buffer (20 mM Tris-HCl, 2 mM EDTA, 2 M NaCl, pH 7.5). Denatured DNA is mixed with equal volume of beads suspension in 2×BW buffer and placed on a rotary shaker for 1 hr at room temperature. The beads are bound to magnet and washed with 3×100 μl each of 1×BW buffer and TE-L buffer. Non-biotinylated DNA is removed by incubating the beads in 100 ml of 0.1 N NaOH for 5 min at room temperature. Beads are neutralized by washing with 5×100 μl of TE-L buffer and resuspended in 20 μl of water.

Adaptor B1 is ligated to the single-stranded library of PENT molecules bound to magnetic beads. Adaptor B1 consists of two oligonucleotides: one is 5'-phosphorylated and 3'-blocked (primer 16); and a second is its complement, which has a 3'-extension of four random bases and is also 3'-blocked (primer 17). The latter oligonucleotide will anneal and direct the phosphorylated adaptor strand to the free 3'-end of single-stranded genomic PENT library molecules. The library DNA from the previous step is mixed with 40 pmoles of each adaptor B1 oligonucleotide (primers 16 and 17) in 1×T4 ligase buffer and 1200 units of T4 ligase (NEB) in final volume of 30 μl. Ligation is performed at room temperature for 1 hour on an end-to-end rotary shaker to keep the beads in suspension. Beads are bound to magnet, washed with 2×100 μl each of 1×BW buffer and TE-L buffer and nonbiotinylated DNA molecules are removed by incubating the beads in 100 μl of 0.1 N NaOH for 5 min at room temperature. Beads are neutralized by washing with 5×100 μl of TE-L buffer, resuspended in 100 μl of storage buffer (SB buffer, containing 0.5 M NaCl, 10 mM Tris-HCl, 10 mM EDTA, pH 7.5) and stored at 4° C.

Figure 20:
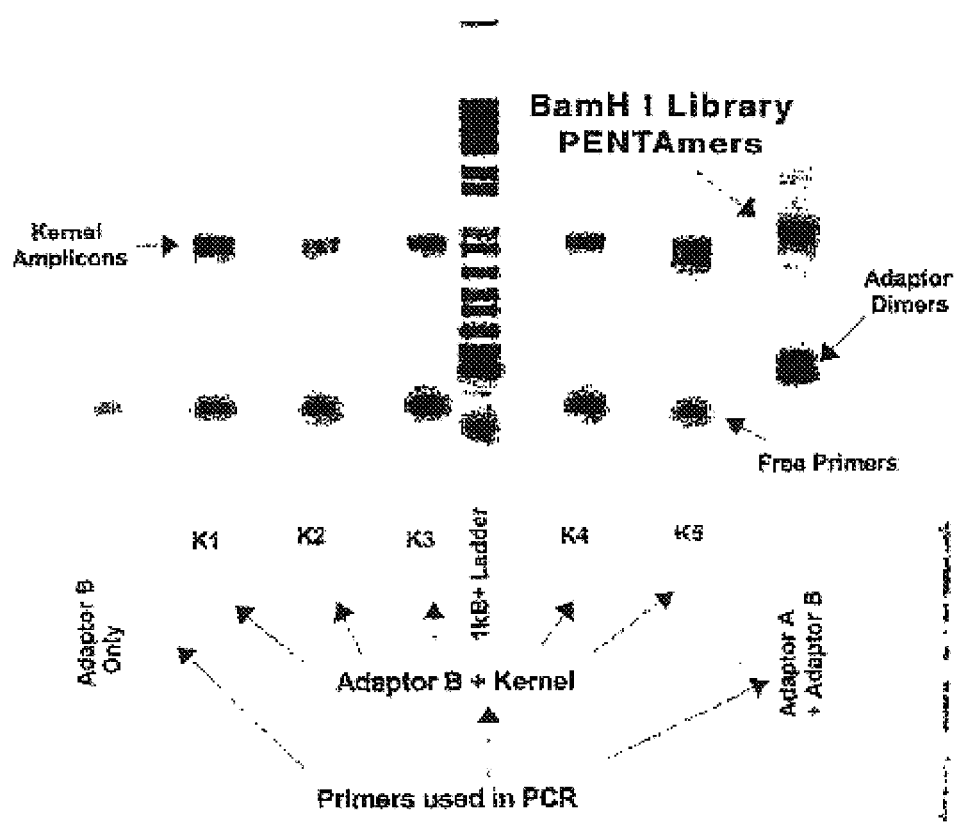
FIG. 20 demonstrates PCR amplification of genomic BamH I PENTAmer E. coli library and selected kernel sequences.

FIG. 20 shows analysis of 5 selected random sequences in the *E. coli* genome adjacent to BamH I sites to assess the quality and representativity of the library. One microliter of library beads diluted 10× in water (approximately 0.1% of the total library DNA) are used as template in PCR amplification reactions with universal adaptor B1 primer primer 18) and 5 specific *E. coli* primers adjacent to BamH I sites. A negative control with adaptor B1 primer alone and a positive control with adaptor B1 and adaptor A3 primers (primers 14 and 18) are also included. After initial denaturing at 95° C. for 1 min, 30 cycles of 94° C. for 10 sec and 68° C. for 75 sec are carried out. Aliquots of the PCR reactions are separated on 1% agarose gel and visualized on Fluor S MultiImager (Bio Rad) after staining with Sybr Gold. All five analyzed *E. coli* sequences are present in the library and are amplified as 1 Kb fragments. The sequences are confirmed by Thermo Sequenase Cy5.5 Dye Terminator Cycle Sequencing kit (Amersham Pharmacia Biotech; Piscataway, N.J.) protocol on OpenGene sequencing system (Visible Genetics) as described in Example 6 with the same kernel primers used in PCR.

Example 2

Preparation of Secondary *E. Coli* Genomic BamHI PENTAmer Library

Secondary library in the following examples is defined as a library derived from primary genomic PENTAmer library by either exponential or linear amplification, which is primarily used as template for selection by ligation and/or extension directed from adaptor A toward adaptor B and thus for the purpose of this application is the strand complementary to the PENT (nick-translation) strand of the primary library form which it is derived. Secondary libraries are potentially biased in representation of genomic sequences.

This example describes the preparation of secondary library derived by PCR amplification of the primary PENTAmer *E. coli* BamH I library described in Example 1. The library is diluted and amplified by PCR in the presence of dUTP and biotinylated B1 adaptor oligonucleotide. Biotinylated dU containing strands are captured to magnetic streptavidin beads. Finally, to prevent the free 3' ends from self-priming during primer extension reactions, 3'-ends are blocked by transfer of dideoxy adenosine with terminal transferase. The library is used as template for selection by assembly, ligation, and extension of contigs of short oligonucleotides at specific positions or for direct primer extension of kernel sequences.

One microliter of primary PENTAmer *E. coli* BamH I genomic library beads diluted 10 times in water (approximately 0.1% of the total primary library) is used as PCR template with biotinylated adaptor B1 primer (primer 19) and adaptor A3 PCR primer (primer 14) in the presence of 0.2 mM of each dNTP and 0.2 mM dUTP. After 25 cycles at 94° C. for 10 sec and 68° C. for 75 sec, three reaction tubes of 25 μl each are combined. The sample is diluted to 300 μl with TE-L buffer (10 mM Tris-HCl, 0.1 mM EDTA, pH 7.5), supplemented with ¼ volume of QF buffer (final concentrations of 240 mM NaCl, 3% isopropanol, and 10 mM Tris-HCl, pH 8.5) and centrifuged at 200×g in Microcon YM-100 (Millipore; Bedford, Mass.) filter to a volume of 100 μl. The sample is then washed 2 times with 400 μl of TE-L buffer at 200×g and concentrated to a final volume of 120 μl. Three hundred micrograms of streptavidin-coated DYNABEADS™ M-280 (Dynal) are prewashed with TE-L buffer and resuspended in 2×BW buffer (20 mM Tris-HCl, 2 mM EDTA, 2 M NaCl, pH 7.5). The DNA sample is mixed with equal volume of beads suspension in 2×BW buffer and placed on rotary shaker for 1 hr at room temperature. The beads are bound to magnet and washed with 3×100 μl each of 1=BW buffer and TE-L buffer. Non-biotinylated DNA is removed by incubating the beads in 100 μl of 0.1 N NaOH for 5 min at room temperature. Beads are neutralized by washing with 5×100 μl of TE-L buffer and then resuspended in 20 ml of water.

To block free 3' termini the beads are supplemented with 1× terminal transferase buffer (Roche; Nutley, N.J.), 0.25 mM $CoCl_2$, 0.1 mM ddATP, and 200 units of terminal transferase (NEB) in a final volume of 50 μl and reaction is carried out at 37° C. for 30 min. Beads are washed with 2×100 μl each of TE-L buffer and 1×BW buffer, resuspended in 50 μl of SB buffer (0.5 M NaCl, 10 mM Tris-HCl, 10 mM EDTA, pH 7.5) and stored at 4° C.

Example 3

Assembly of Short Oligonucleotides at Specific *E. Coli* Genomic Kernel Sequence by Thermo-Stable DNA Ligase Using Secondary *E. Coli* Genomic BamHI PENTAmer Library as Template This example describes the assembly of contigs of 5 or 8 nonamer oligonucleotides at specific *E. coli* kernel sequence adjacent to BamH I restriction site by using thermo-stable ligase and secondary *E. coli* genomic BamHI PENTAmer library described in Example 2 as template.

Figure 21:
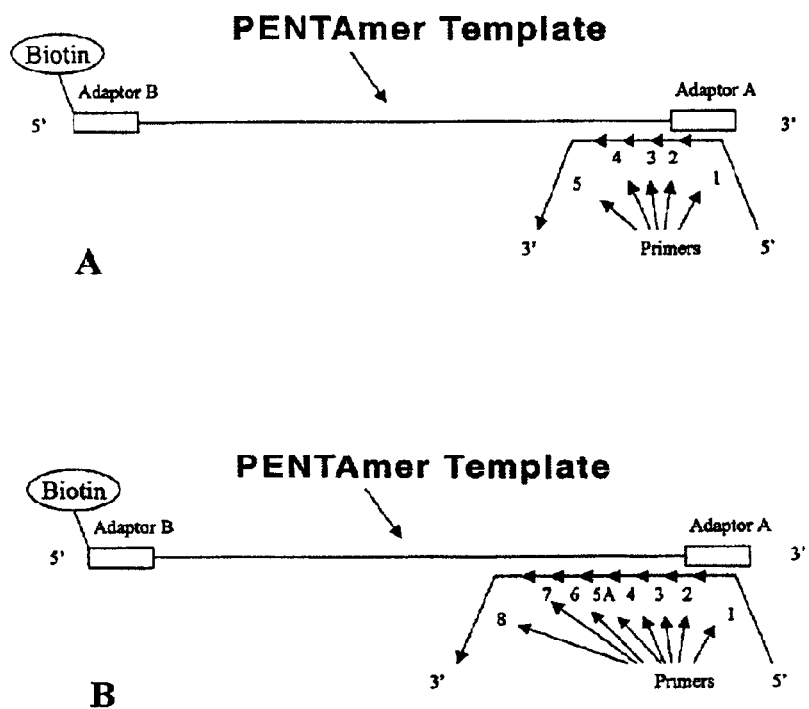
FIG. 21 illustrates schematic presentation of assembly of short oligonucleotides on E. coli BamH I PENTAmer library template.

Two sets of oligonucleotides complementary to a kernel sequence adjacent to BamH I restriction site are mixed in 1×Tsc ligase buffer (Roche; Nutley, N.J.) as follows:

Set 1. Oligonucleotides 1, 2, 3, 4, and 5 annealing at the selected kernel as contig (FIG. 21A, Table VII) are mixed at final concentration of 10 nM each, except oligonucleotide 5, at 50 nM. Oligonucleotide 1 is complementary in its twelve 3'-terminal bases to adaptor A3 sequence immediately upstream from the BamH I restriction site and has an unique 5' extension of 23 bases used as PCR priming site. Oligonucleotide 5 is complementary in its nine 5'-terminal bases to the sequence being selected and has a unique 3'-extension of 23 bases used as second priming site for PCR. All oligonucleotides except oligonucleotide 1 are 5'-phosphorylated.

Set 2. Oligonucleotides 1, 2, 3, 4, 5A, 6, 7 and 8 annealing at the selected kernel as contig (FIG. 21B, Table VII) are mixed at final concentration of 10 nM each except oligonucleotides 5A and 8, at 50 nM. Oligonucleotide 1 is complementary in its twelve 3'-terminal bases to adaptor A3 sequence immediately upstream from the BamH I restriction site and has a unique 5' extension of 23 bases used as PCR priming site. Oligonucleotide 8 is complementary in its nine 5'-terminal bases to the sequence being selected and has a unique 3'-extension (identical to the extension of oligonucleotide 5) of 23 bases used as second priming site for PCR. All oligonucleotides except oligonucleotide 1 are 5'-phosphorylated.

TABLE VII

OLIGONUCLEOTIDES*

| Number | Sequence (5'–3') | Length (bases) and Modifications | Application |
|---|---|---|---|
| 1. | cgg tgc atg tgt atc gtc cgsa gtt caa caa cct ca (SEQ ID NO:1) | 35 | Universal primer for selection by ligation |
| 2. | gat ccc cat (SEQ ID NO:2) | 9$^b$ | selective contig assembly |
| 3. | ttc cag acg (SEQ ID NO:3) | 9$^b$ | selective contig assembly |
| 4. | ata agg ctg (SEQ ID NO:4) | 9$^b$ | selective contig assembly |
| 5. | cat taa atc atc gca gta gca ttg act cag cc (SEQ ID NO:5) | 32$^b$ | selective contig assembly with unique 3' extension |
| 5A. | cat taa atc (SEQ ID NO:6) | 9$^b$ | selective contig assembly |
| 6. | gag cgg gcg (SEQ ID NO:7) | 9$^b$ | selective contig assembly |
| 7. | cag tac gcc (SEQ ID NO:8) | 9$^b$ | selective contig assembly |
| 8. | ata caa gcc atc gca gta gca ttg act cag cc(SEQ ID NO:9) | 32$^b$ | selective contig assembly with unique 3' extension |
| 8A. | ata caa gcc (SEQ ID NO:10) | 9$^b$ | selective contig assembly |
| 9. | cgg tgc atg tgt atc gtc cga gt (SEQ ID NO:11) | 23 | Upstream PCR primer used to amplify sequences selected by assembly of short oligos |
| 10. | ggc tga gtc aat gct act gcg at (SEQ ID NO:12) | 23 | Downstream PCR primer used to amplify sequences selected by assembly of short oligos |
| 11. | gat ctg agg ttg ttg aag cgt (SEQ ID NO: 13) | 42$^{b,\ c}$ | Adaptor A3 backbone tua ccc |
| 12. | Ttg cct aau cga aut ggg uaa acg (SEQ ID NO:14) | 24$^d$ | Adaptors A3 nick-translation primer |
| 13. | ctt caa caa cct ca (SEQ ID NO:15) | 14$^c$ | Adaptor A3 blocking primer |
| 14. | ttg cct aat cga att ggg taa acg (SEQ ID NO:16) | 24 | Adaptors A3 PCR primer |
| 15. | ttg cct aat cga att ggg taa acg ctt caa caa cct cag atc (SEQ ID NO:17) | 42$^c$ | AdaptorA3 backbone complement block |
| 16. | tta cga tac gag tct ttg tca cct tcc gcg atg atc ttg cag act t (SEQ ID NO:18) | 46$^{b,\ c}$ | Adaptor B1 phosphorylated strand |
| 17. | aag tct gca aga tca tcg cgg aag gtg aca aag act cgt atc gta aNNNNc (SEQ ID NO:19) | 51$^c$ | Adaptor B1 poly N strand |
| 18. | aag tct gca aga tca tcg cgg aa (SEQ ID NO:20) | 23 | Adaptor B1 distal PCR primer |
| 19. | aag tct gca aga tca tcg cgg aa (SEQ ID NO:21) | 23$^d$ | Adaptor B1 PCR primer with 5' biotin |
| 20. | acg ggc tag caa aat agc gct gtc c(N)g atc tga ggt tgt tga agc g (SEQ ID NO:22) | 46$^c$ | Blocking primer to prevent adaptor A3–B1 dimers formation |
| 21. | gga cag cgc tat ttt gct agc ccg t (SEQ ID NO:23) | 25$^c$ | Blocking primer to prevent adaptor A3–B1 dimers formation |
| 22. | ggt gac aaa gac tcg tat cgt aa (SEQ ID NO:24) | 23 | Adaptor B1 proximal PCR primer |

TABLE VII-continued

OLIGONUCLEOTIDES*

| Number | Sequence (5'–3') | Length (bases) and Modifications | Application |
|---|---|---|---|
| 23. | ttg cct aat cga att ggg taa acg (SEQ ID NO:25) | 24[b] | Adaptors A3 PCR primer |
| 24. | gat ctg agg ttg ttg aag cgt tta ccc aat tcg att agg caa agg tct gca aga tca tcg (SEQ ID NO:26) | 60[c] | Bridging oligonucleotide for circularization of single-stranded PENTamere libraries |
| 25. | tta ccc aat tcg att agg caa (SEQ ID NO:27) | 21 | Adaptor A3 circular PCR primer |
| 26. | cgc ttc aac aac ctc aga tc (SEQ ID NO:28) | 20 | Adaptor A3 circular PCR primer |

*All oligonucleotides are synthesized at Integrated DNA Technologies
[a]5' Cy 5.0 labeled
[b]5' phosphorylated
[c]3' C7 amino blocked
[e]5' fluorescein labeled
[d]5' biotinylated
N random base Three microliters of 2.5-fold diluted secondary *E. coli* genomic BamHI PENTAmer library beads prepared as described in Example 2 are added to the prepared sets of oligonucleotides together with 7.5 units of Tsc ligase (Roche; Nutley, N.J.) or 1×Tsc buffer as control in final volume of 30 µl. Incubation is carried out at 32° C. or 45° C. for 3 hours. Beads are washed 2 times with 50 ml each of 2× BW buffer and TE-L buffer and non-biotinylated DNA is eluted with 20 µl of 0.1 N NaOH for 3 min at 37° C. Beads are bound to magnet and supernatants neutralized with 10 ml of 0.2 N HCl and 3 µl of 1 M Tris-HCl, pH 8.0. Samples are diluted to 100 µl with water, split in 2 aliquots of 50 µl and one aliquot is treated with 1 unit of heat-labile uracil-DNA glycosylase (UDG, Roche; Nutley, N.J.) for 2 hours at 20° C. UDG is inactivated for 10 min at 95° C. and 1 µl of 3-fold diluted aliquot of each sample is used as template for PCR with primer identical to the unique 5' extension of oligonucleotide 1 (primer 9) and primer complementary to the unique 3' extension of oligonucleotides 5 and 8 (primer 10).

Figure 22:
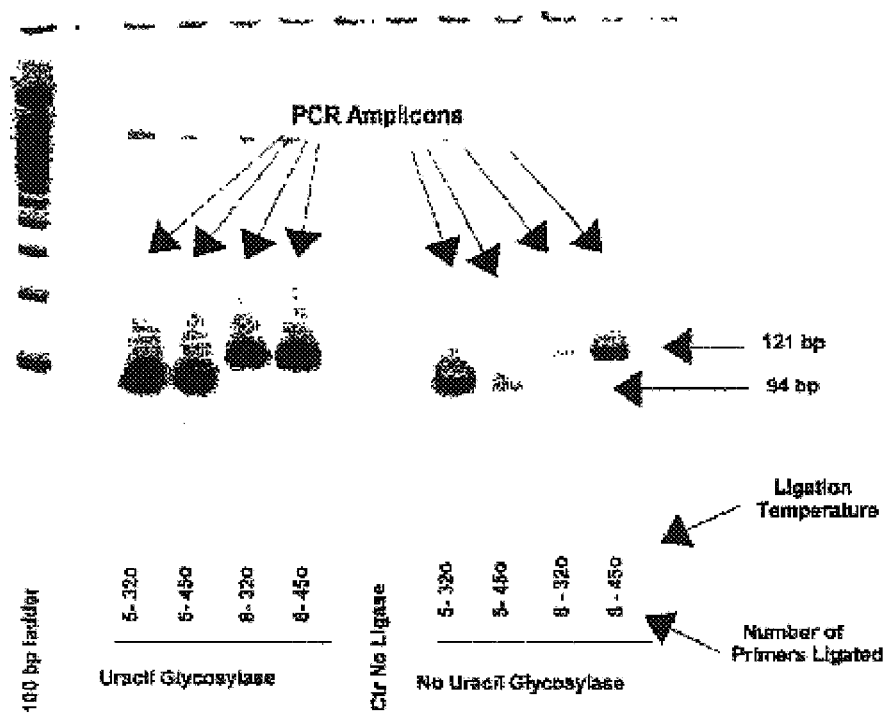
FIG. 22 demonstrates assembly of short oligonucleotides at specific E. coli genomic kernel sequence by thermo-stable DNA ligase using secondary E. coli genomic BamH I PENTamer library as template.

FIG. 22 shows analysis of 10 µl aliquots of the PCR reactions by electrophoresis on 10% TBE acrylamide gel (Novex; San Diego, Calif.) after staining with SYBR GOLD™ on Bio-Rad (Hercules, Calif.) Fluor S MultiImager. Both 5 oligonucleotide and 8 oligonucleotide contigs were assembled as evidenced by 94 bp and 121 bp amplicons obtained by PCR respectively.

This example demonstrates that contigs of short oligonucleotides can be successfully assembled at specific kernel positions using secondary *E. coli* PENTAmer library as template. Assembled contigs are stable upon washing in low salt buffer (TE-L) and can be extended with DNA polymerase at high temperature as shown in Example 4. Selected sequences can be used for walking, sequencing, and for gap filling after destroying any residual dU-containing PENTAmer molecules with uracil DNA glycosylase.

Example 4

Selection of Specific *E. Coli* Pentamer Sequence by Assembly of Short Oligonucleotides Followed by Extension with DNA Polymerase and Ligation of Universal Oligonucleotide at Adaptor A Using Secondary *E. Coli* Genomic BamHI PENTAmer Library as Template This example describes amplification of specific *E. coli* PENTAmer sequence by assembly of short oligonucleotides, followed by extension and ligation of universal adaptor A oligonucleotide having unique 5'-terminal extension used as priming site for PCR.

Oligonucleotides 2, 3, 4, 5A, 6, 7 and 8A annealing as contig at specific kernel sequence adjacent to BamH I restriction site (Example 3, FIG. 21B) are mixed in 1×Tsc ligase buffer (Roche; Nutley, N.J.) at final concentration of 10 nM each except oligonucleotides 5A and 8A, at 50 nM. All oligonucleotides are 5'-phosphorylated. Four microliters of 2.5-fold diluted secondary *E. coli* genomic BamHI PENTAmer library beads prepared as described in Example 2 are added to the oligonucleotide mix in total volume of 100 ml. The sample is divided into 3 aliquots. 7.5 units of Tcs DNA ligase (Roche; Nutley, N.J.) are added to tube #1 and tube #2 whereas tube #3 (control) receives 1.5 µl of 1×Tsc ligase buffer. Incubation is carried out at 45° C. for 2 hours. Beads are washed 2 times with 50 ml each of 2× BW buffer and TE-L buffer and resuspended in 5 µl of water. Samples are then supplemented with 1×ThermoPol buffer (NEB), 10 mM MgCl₂, 5 units of Bst DNA polymerase (NEB) and 0.2 mM of each dNTP in final volume of 60 ml and extension reaction is carried out at 55° C. for 3 min. Reactions are stopped by addition of 1 ml of 0.5M EDTA, pH 8.0 and beads are washed with 2×50 µl of 2× BW buffer, 2×50 µl of TE-L buffer and 50 µl of water. Beads are then resuspended in 25 µl of water.

Samples are supplemented with 1×Tsc ligase buffer (Roche; Nutley, N.J.) and 10 nM of oligonucleotide 1 (Table VII) in final volume of 30 µl. Oligonucleotide 1 is complementary in its twelve 3'-terminal bases to adaptor A3 sequence adjacent to the assembled contig and has an unique 5' extension of 23 bases used later as PCR priming site. Five units of Tsc DNA ligase (Roche; Nutley, N.J.) are added to samples #1 and #3 whereas sample #2 receives 1 µl of 1×Tsc ligase buffer. Ligation is carried out at 45° C. for 1 hour. Beads are washed sequentially with 2×50 µl of 2× BW buffer, 2×50 µl TE-L buffer, 50 µl of water, 2×50 µl of 2× BW buffer, and 50 µl of TE-L buffer. Non-biotinylated DNA is eluted with 20 µl of 0.1 N NaOH for 3 min at 37° C. Beads are removed on magnet and supernatant is neutralized with 10 µl of 0.2 N HCl and 3 µl of 1 M Tris-HCl, pH 8.0. Samples are diluted to 100 µl with water, split into two aliquots of 50 µl and one half treated with 1 unit of heat-labile uracil-DNA-glycosylase (UDG, Roche; Nutley, N.J.) for 2 hours at 20° C. UDG is inactivated for 10 min at 95° C. and 1 µl of 3-fold diluted aliquot of each sample is used as template for PCR. Amplification is performed with primer identical to the unique 5' extension of oligonucleotide 1 (primer 9) or kernel primer adjacent to the Bam H I site of the selected PENTAmer and universal adaptor B1 primer (primer 18).

Figure 23:
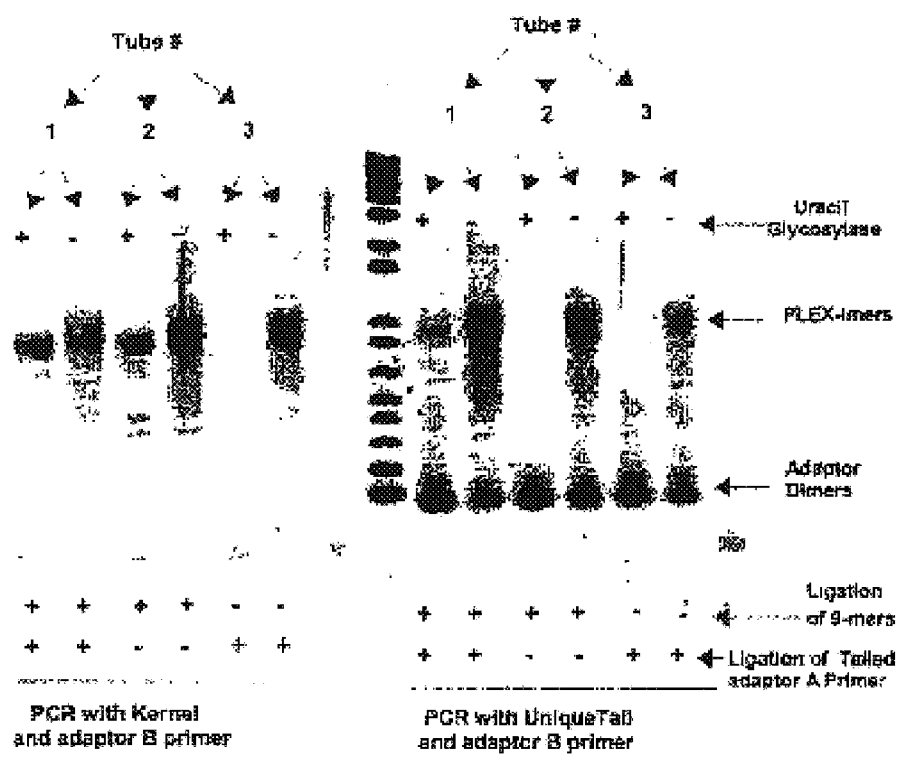
FIG. 23 shows selection of specific E. coli PENTAmer sequence by assembly of short oligonucleotides followed by extension with DNA polymerase and ligation of universal adaptor oligonucleotide at adaptor A using secondary E. coli genomic BamH I PENTAmer library as template.

FIG. 23 shows analysis of 12 µl aliquots of the PCR reactions by electrophoresis on 10% TBE acrylamide gel (Novex; San Diego, Calif.) after staining with Sybr Gold performed on Bio-Rad (Hercules, Calif.) Fluor S MultiImager. PCR amplification with both sets of primers from samples which have the contig of 9-mer oligonucleotides ligated produced a 1 Kb amplicon corresponding to the specific PENTAmer (lanes 1, 3, and 9). The control (tube #3) in which short oligos are present but no ligase is added does not have the amplicon, indicating that no extension from short oligos occurs in the absence of ligation (lanes 5 and 13). The sample which did not have adaptor A tailed oligonucleotide ligated (tube #2) is negative when probed by PCR with the tail primer 9 (lane 11). This validates the specificity of the second ligation step. In all controls in which dU containing strands have not been destroyed by uracil glycosylase, non-specific PENTAmers are amplified indicating release of some biotinylated strands by NaOH treatment (lanes 2, 4, 6, 10, 12, and 14).

This example demonstrates that contigs of short oligonucleotides can be successfully assembled and extended at specific kernel positions using *E. coli* PENTAmer library as template. Ligation of universal adaptor A oligonucleotide with unique 5'-tail and destruction of dU containing PENTAmer with uracil glycosylase allows additional level of selective specificity.

Example 5

Preparation and Analysis of Primary PENTAmer Library from *E. Coli* Sau3A I Partial Genomic Digest This Example describes preparation of primary PENTAmer library from *E. coli* genomic DNA using partial digest with frequently cutting enzyme. As shown in the following examples, this library can be used for filling gaps and de novo sequencing of genomes having the complexity of an average bacterial genome.

After performing an experiment to test the efficiency of partial restriction digestion, aliquots of 2 µg of *E. coli* genomic DNA prepared by standard purification are digested in three separate tubes with 4, 2, or 1 unit(s) of Sau3A I (New England Biolabs; Beverly, Mass.) for 20 min at 37° C. in final volume of 100 ml. Samples are combined and DNA fragments are size-fractionated by Reverse Phase Isodimensional Focusing RF-IDF) electrophoresis. Combined sample is loaded in preparative lane on 0.55% pulse-field grade agarose gel (Bio-Rad; Hercules, Calif.) along with 1 Kb+ ladder (Life Technologies; Rockville, Md.). Electrophoresis in the forward direction is performed at 6 V/cm in interrupted mode (60 sec on, 5 sec off) for 1.5 hours. Section of the gel containing a lane of standards and a lane of the DNA sample is excised, stained with Sybr Gold and bands are visualized on Dark Reader Blue Light Transilluminator (Clare Chemical Research). Region of the gel containing DNA molecules smaller than 2 Kb is cut out and removed. The remaining portion of the stained slice is aligned back with the unstained gel and used as a landmark for cutting and removing of the fraction containing DNA fragments bellow 2 Kb. The unstained gel is then run in reverse direction in interrupted field of 6 V/cm (60 sec on, 5 sec off) for 85% of the forward time. After electrophoresis is complete the gel is stained with Sybr Gold. The band of interest now focused in a sharp narrow region is cut out and recovered from the agarose using Gel Extraction kit (Qiagen; Valencia, Calif.) in 10 mM Tris-HCl pH 8.5.

The sample is split into two tubes, supplemented with 1×SAP buffer (Roche; Nutley, N.J.), and DNA is dephosphorylated with 15 units of SAP (Roche; Nutley, N.J.) for 20 min at 37° C. SAP is heat-inactivated for 15 min at 65° C., and DNA is purified by extraction with equal volume of phenol:chloroform:isoamyl alcohol (25:24:1) and precipitation with ethanol. Digested DNA is dissolved in 100 µl of TE-L buffer.

The sample is mixed with 40 pmoles of pre-assembled BamH I nick-translation adaptor (adaptor A3 consisting of primers 11, 12, and 13; Table VI) and ligation is carried out overnight at 16° C. with 2,800 units of T4 ligase (NEB). To remove ligase and excess free adaptor the sample is extracted with equal volume of phenol:chloroform:isoamyl alcohol (25:24:1), mixed with ¼ vol of QF buffer (final concentrations of 240 mM NaCl, 3% isopropanol, and 10 mM Tris-HCl, pH 8.5) in a volume of 400 µl and centrifuged at 200×g to a volume of approximately 100 µl on Microcon YM-100. The sample is washed 3 times with 400 µl of TE-L buffer at 200×g and concentrated to a final volume of 135 µl.

The purified sample is subjected to nick-translation with 38 units of wild type Taq polymerase in 1× Perkin Elmer (Norwalk, Conn.) PCR buffer buffer II containing 4 mM MgCl$_2$ and 200 mM of each dNTP in final volume of 240 µl for 5 min at 50° C. Reaction is stopped by addition of 6 µl of 0.5 M EDTA pH 8.0 and products are analyzed on 6% TBE-urea gel (Novex; San Diego, Calif.) after staining with SYBR GOLD™.

The sample is supplemented with blocking oligonucleotide complementary to the nick-translation template strand adaptor sequence (primer 15) at a final concentration of 1 mM, denatured by boiling at 100° C. for 3 min, and cooled on ice for 5 min. Twelve hundred micrograms of streptavidin coated DYNABEADS™ M-280 (Dynal) are prewashed with TE-L buffer and resuspended in 2×BW buffer (20 mM Tris-HCl, 2 mM EDTA, 2 M NaCl, pH 7.5). Denatured DNA is mixed with equal volume of beads suspension in 2×BW buffer and placed on rotary shaker for 2 hr at room temperature. The beads are bound to magnet and washed with 2×100 µl each of 1×BW buffer and TE-L buffer. Non-biotinylated DNA is removed by incubating the beads in 100 ml of 0.1 N NaOH for 5 min at room temperature. Beads are washed with 100 µl of 0.1 N NaOH, neutralized by washing with 5×100 µl of TE-L buffer, and resuspended in 150 µl of TE-L buffer.

One half of the prepared library DNA is then processed for ligation with adaptor B1. To minimize formation of adaptor A-B dimers on magnetic beads, the suspension (75 µl) is supplemented with 1× T4 ligase buffer (NEB) incubated with 50 pmoles of 3'-blocked oligonucleotides one of which is complementary to the biotinylated adaptor A strand and has 3'-extension of 24 bases (primer 20) to which the second oligonucleotide (primer 21) is complementary. The suspension is heated for 1 min at 60° C., cooled to room temperature and incubated for 10 min at room temperature to anneal the blocking oligonucleotides to residual free adaptor A3 molecules bound to magnetic beads. Beads are then washed with 50 µl of 1×T4 ligase buffer and resuspended in 50 µl of the same buffer. Adaptor B1 is then ligated to the library DNA. The sample from the previous step is supplemented with 40 pmoles of each adaptor B oligonucleotide (primers 16 and 17) in 1×T4 ligase buffer and 4000 units of T4 ligase (NEB) in final volume of 55 µl. Ligation is performed at room temperature for 3 hours on end-to-end rotary shaker. Beads are bound to magnet, washed with 2×100 µl each of 1×BW buffer and TE-L buffer and nonbiotinylated DNA removed by incubating the beads in 100 µl of 0.1 N NaOH for 5 min at room temperature. Beads are washed with 100 µl of 0.1 N NaOH, neutralized by washing with 5×100 ml of TE-L buffer, resuspended in 90 ml of SB buffer and stored at 4° C.

Figure 24:
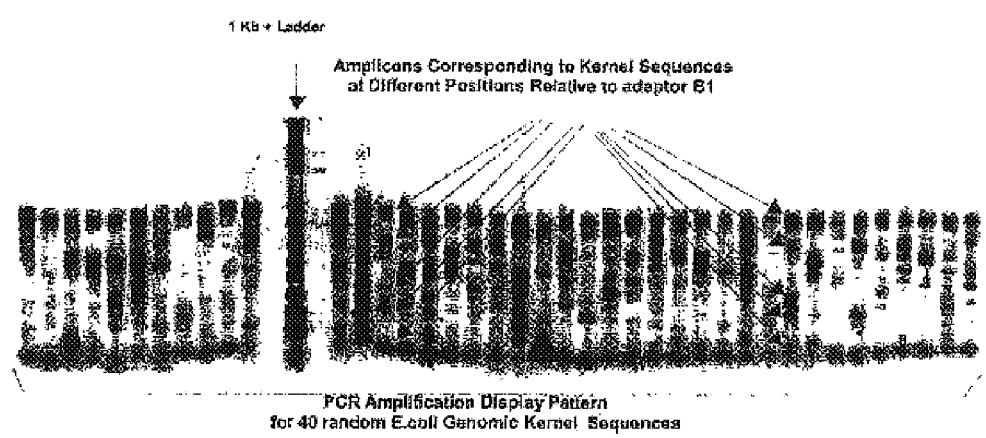
FIG. 24 demonstrates PCR analysis of forty kernel sites in primary PENTAmer library from E. coli Sau3A I partial genomic digest.

Representativity of the PENTAmer library from *E. coli* Sau3A I partial genomic digest is analyzed by PCR amplification with 50 random kernel primers and universal adaptor B1 primer. Kernel primers specific for regions of the *E. coli* genome located approximately 50–250 bp downstream of Sau3A I restriction sites are designed to have high internal stability and low frequency of their six 3'-terminal bases matched against *E. coli* genomic frequency database (Oligo Primer Analysis software, Molecular Biology Insights). Magnetic beads containing library DNA are prewashed with water and 1 ml (1.1% of the total library DNA) used as template for PCR amplification with 100 nM of universal adaptor B primer (primer 18) and 100 nM of each *E. coli* kernel primer in a final volume of 25 ml. After initial denaturing at 95° C. for 1 min, 32 cycles are carried out at 94° C. for 10 sec and 68° C. for 75 sec. Five ml aliquots are separated on 1% agarose gel and visualized on Fluor S MultiImager (Bio Rad) after staining with Sybr Gold. FIG. 24 shows the amplification patterns obtained with 40 representative kernel primers. The bands of different size in each lane correspond to amplified PENTAmers having the kernel sequence at different positions relative to the nick-translation termination sites (ligated adaptor B1). Although PENTAmer molecules are size-fractionated and are all in the range of 1 Kb, the relative position of any kernel sequence will be shifted in individual PENT molecules originating at given Sau3A I restriction site. Thus the pattern of amplification reflects the frequency of Sau3A I sites located upstream from each kernel.

This example demonstrates that representative normalized primary PENTAmer library can be produced from from PENTAmer library prepared from partial Sau3A I restriction digest.

Example 6

Genome Walking Sequencing of 50 Sample Sequences in *E. Coli* Using Primary PENTAmer Library Prepared from Partial Sau3A I Restriction Digest This example validates a direct genome walking sequencing strategy for gap filling and de novo sequencing of genomes of the complexity of *E. coli* from PENTAmer library prepared with frequently cutting restriction enzyme.

Fifty random oligonucleotides specific for regions of the *E. coli* genome located approximately 50–250 bp downstream of Sau3A I restriction sites are designed using Oligo Primer Analysis software (Molecular Biology Insights). Magnetic beads containing *E. coli* PENTAmer library DNA described in Example 4 are prewashed with water and 1 ml (approximately 1.1% of the total library DNA) used as template for PCR amplification with 100 nM of universal adaptor B primer (primer 18) and 100 nM of each *E. coli* kernel primer in a final volume of 25 µl. After initial denaturing at 95° C. for 1 min, 32 cycles are carried out at 94° C. for 10 sec and 68° C. for 75 sec. Five ml aliquots of 40 representative reactions are separated on 1% agarose gel and visualized on Fluor S MultiImager (Bio Rad) after staining with SYBR GOLD™. As shown in Example 5 (FIG. 24) specific patterns of fragments are generated for each sequence.

PCR amplicons are purified free of polymerase, nucleotides and primers by Qiaquick PCR purification kit (Qiagen; Valencia, Calif.) and are eluted in 30 µl of EB buffer (Qiagen (Valencia Calif.), 100 mM Tris-HCl, pH 8.5). DNA is quantitated by mixing 15 µl of serial dilutions of the purified samples with equal volume of 1:200 diluted Pico Green reagent (Molecular Probes; Eugene, Oreg.) in TE buffer, incubating at room temperature for 5 min and spotting 20 µl aliquots along with standard amounts of DNA (low DNA Mass Ladder, Life Technologies; Rockville, Md.) on Parafilm (American National Can). DNA is quantitated on Bio-Rad (Hercules, Calif.) Fluor S MultiImager using the volume tool of Quantity One software (Bio Rad).

Cycle sequencing is performed by mixing 11 µl of DNA samples containing 55–80 ng of total DNA with 1 µl of 5 mM of each kernel primer used originally in PCR (above) and 8 µl of DYEnamic ET teminator reagent mix (Amersham Pharmacia Biotech; Piscataway, N.J.) in 96 well plates in final volume of 20 µl. Amplification is performed for 30 cycles at: 94° C. for 2 sec, 58° C. for 15 sec, and 60° C. for 75 sec. Samples are precipitated with 70% ethanol and analyzed on MegaBACE 1000 capillary sequencing system (Amersham Pharmacia Biotech; Piscataway, N.J.) under the manufacturer's protocol.

Alternatively, cycle sequencing is done using the Thermo Sequenase Cy5.5 Dye Terminator Cycle Sequencing kit (Amersham Pharmacia Biotech; Piscataway, N.J.) by mixing 24 µl of template containing 20–50 ng of DNA with 1 µl of 10 mM primer, 1 µl of each individual Cy5.5 dye-labeled ddNTP teminator, 3.5 µl of reaction buffer concentrate, and 20 units of Thermo Sequenase DNA polymerase in total volume of 31.5 µl. After initial denaturing at 94° C. for 1 min, amplification is performed for 30 cycles at: 94° C. for 10 sec, 58° C. for 30 sec, and 72° C. for 1 min. Samples are purified by DyeEx dye terminator removal kit (Qiagen; Valencia, Calif.) and analyzed on OpenGene sequencing system (Visible Genetics).

Table VIII shows a summary of the sequencing results obtained with fifty *E. coli* kernel primers on the MegaBACE 1000 sequence analyzer in a single run. On average read lengths of the analyzed sequences are in the order of 500 bases. A sequence is considered to be a failure if about 100 or less bases are called. At a preset threshold score of >20 using the Phred algorithm (Codon Code Corporation; Dedham, Mass.) which corresponds to an error probability of 1%, twenty two percent of the sequences failed, whereas at a Phred value of 10 (90% accuracy), the failure rate is 20%.

TABLE VIII

Summary of 50 E.coli Kernel Sites Sequenced Directly from Primary PENTAmer library of Partial Sau3A I Restriction Digest

| Sequence ID[a] | Read length (bases):[b] Phred > 20 (99% accuracy); failure: <100 bases called | Read length (bases):[c] Phred > 10 (90% accuracy); failure: <100 bases called | Read length (bases):[a] Cimarron 1.53 Slim Phredify/Quality Index failure: <100 bases called |
|---|---|---|---|
| S1 | | | |
| S2 | 614 | 677 | 651/95 |
| S3 | 557 | 593 | 706/95 |
| S4 | failure* | failure* | failure* |
| S5 | 399 | 421 | 414/96 |
| S6 | 665 | 757 | 844/91 |
| S7 | failure* | failure* | failure* |
| S8 | 673 | 706 | 435/95 |
| S9 | failure* | failure* | failure* |
| S10 | 383 | 423 | 453/95 |
| S11 | 569 | 605 | 618/94 |
| S12 | 449 | 533 | 629/92 |
| S13 | 494 | 533 | 627/93 |
| S14 | 527 | 540 | 550/97 |
| S15 | 573 | 619 | 633/96 |
| S16 | 111 | 129 | 549/90 |
| S17 | failure* | failure* | failure* |
| S18 | 679 | 765 | 773/91 |
| S19 | 611 | 682 | 812/93 |
| S20 | 676 | 741 | 906/93 |
| S21 | 609 | 628 | 631/96 |
| S22 | 683 | 712 | 733/97 |
| S23 | failure* | 141 | 178/81 |
| S24 | 533 | 584 | 673/95 |
| S25 | 670 | 711 | 780/96 |
| S26 | 489 | 698 | 398/88 |
| S27 | 580 | 618 | 736/94 |
| S28 | 628 | 663 | 689/97 |
| S29 | failure* | failure* | failure* |
| S30 | 438 | 501 | 429/93 |
| S31 | failure* | failure* | failure* |
| S32 | 565 | 620 | 574/96 |
| S33 | 109 | 153 | 248/87 |
| S34 | 174 | 267 | 341/86 |
| S35 | 210 | 314 | 301/89 |
| S36 | 456 | 530 | 596/91 |
| S37 | 607 | 636 | 729/95 |
| S38 | 565 | 612 | 608/97 |
| S39 | 490 | 593 | 586/94 |
| S40 | failure* | failure* | failure* |
| S41 | 163 | 267 | 320/87 |
| S42 | 500 | 577 | 397/93 |
| S43 | 573 | 610 | 618/95 |
| S44 | failure* | failure* | 415/85 |
| S45 | failure* | failure* | 306/84 |
| S46 | failure* | failure* | 321/86 |
| S47 | 480 | 543 | 553/93 |
| S48 | 460 | 526 | 506/92 |
| S49 | 498 | 554 | 713/91 |
| S50 | 234 | 406 | 239/86 |
| | Failure rate: 22% Average read length: 495 (not including failures) | Failure rate: 20% Average read Length 546 (not including failures) | Failure rate: 14% Average read length 554 (not including failures) Average quality index: 92 |

[a]Specific kernel E. coli primers annealing 1–250 bases downstream from a Sau3A I sites used in cycle sequencing.
[b]Number of bases the Phred (Codon Code Corporation, Dedham, MA) algorithm considers above the threshold score of 20. A Phred score of 20 corresponds to an error probability of 1%.
[c]Number of bases the Phred (Codon Code Corporation, Dedham, MA) algorithm considers above the threshold score of 10. A Phred score of 10 corresponds to an error probability of 10%.
[d]Number of bases called by the Cimarron 1.53 Slim Phredify basecaller (Amersham Pharmacia Biotech Inc., Piscataway, NJ). The Quality Index corresponds to the accuracy rate of the called bases.
*A sequence is considered a failure when less than 100 bases are called.

In addition, forty six PCR samples out of the fifty analyzed in Table VIII are sequenced using the Thermo Sequenase Cy5.5 Dye Terminator Cycle Sequencing kit (Amersham Pharmacia Biotech) as described above and analyzed on OpenGene sequencing system (Visible Genetics). Average data from two independent amplification and cycle sequencing reactions at threshold score of >20 using the Phred algorithm produced read lengths of 291 bases. The failure rate of samples yielding read lengths of less than 100 bases in this sequencing protocol at Phred value of >20 is 17%.

Combining the results from the two sets of direct sequencing experiments from primary PENTAmer library yielded a total of 6 failed samples out of 50, representing a success rate of 88% at a Phred value of >20. This result suggests that almost half of the failed samples on any of the two sequencing protocols are random failures.

Five of the samples that failed in the first sequencing attempt (FIG. 24, samples S7, S9, S23, S29, and S40) are re-sequenced through the Visible Genetics protocol, using same primers in PCR amplification but nested sequencing primers. All of them produced good sequence data, with an average read length of 234 bases at Phred of >20.

This example demonstrates that an average of 88% of random genomic $E.$ $coli$ sequences can be amplified directly from primary PENTAmer library of partial restriction digest with frequently cutting enzyme. Read lengths are on average 250 bases for the Visible Genetics instrument and 500 for the MegaBACE instrument respectively, at accuracy level of 99%. All of the failed samples that were attempted for re-sequencing by using nested primers during cycle sequencing were successful. Due to the length variation in the termination positions of PENT products during nick-translation ("fuzzy ends"), the concentration of intervening adaptor B sequences originating from Sau3A sites upstream of a given kernel is apparently diluted to a point where no significant interference occurs and the read length and quality of the sequencing reactions are comparable to sequencing uniformly sized PCR fragments. However, some sequences containing very short fragments (for example, see FIG. 24, lane 21) have reduced concentration of the full length and intermediate size amplicons due to PCR bias in favor of the shorter fragment. These are usually kernel sequences which happen to fall in the range of 800 bp to 1 Kb downstream of clusters of Sau3A I restriction sites. Initiation of PENT synthesis from such clustered Sau3A I sites brings the kernel sequence in close proximity of adaptor B resulting in short amplicons. In other cases, excessive mis-priming and/or incomparability between kernel and universal primers is the probable reason for failure. Whatever the reason for sequencing failures, it should be mentioned that no simple correlation between the pattern of PCR fragments on FIG. 24 and the failure of sequencing can be established. In cases where amplification of only short fragments is the suspected reason for sequencing failure, size fractionation of the PCR products followed by reamplification is performed as described in Example 7.

Example 7

Genome Walking Sequencing in $E.$ $Coli$ After Size Fractionation of PCR Amplicons Obtained from Primary PENTAmer Library of Partial Sau3AI Restriction Digest This Example shows that samples amplified directly from primary PENTAmer library of partial Sau3A I restriction digest can be size-separated and re-amplified by PCR to eliminate interference of very short fragments on the read length and/or the quality of the sequencing data. Selected sequences among the 55 originally studied in Example 6 are analyzed by creating a pool of the PCR products from the first amplification followed by size fractionation to reduce the bias against large fragments.

Figure 25:
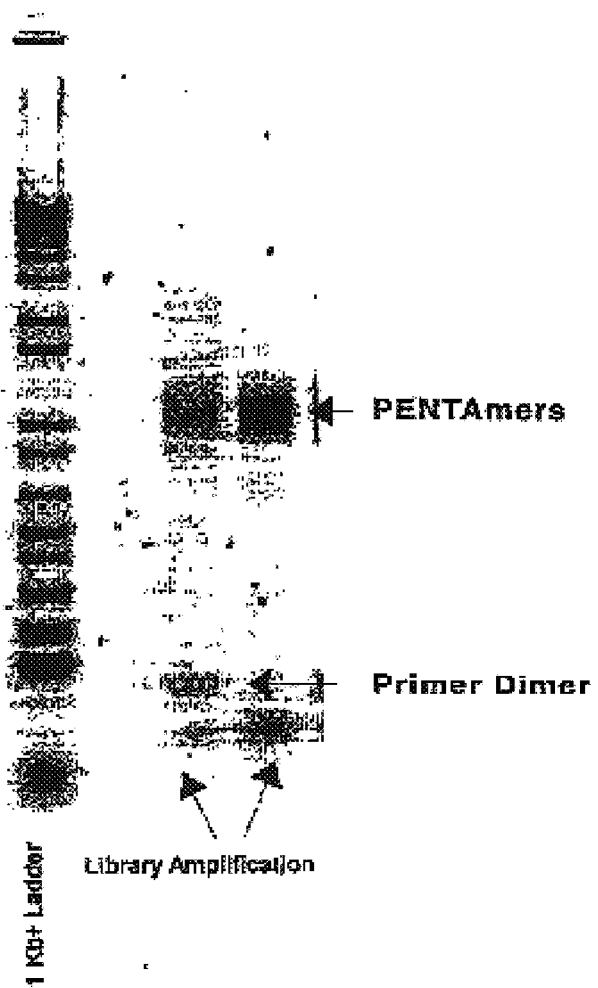
FIG. 25 shows PCR analysis of two kernel sites in PENTAmer library from E. coli Sau3A I partial genomic digest after size separation.

After amplification of fifty-five $E.$ $coli$ kernel sequences described in Example 5, aliquots of 1 $\mu$l of each individual PCR sample are combined and 12 $\mu$l subjected to Reverse Field Isodimensional Focusing (RF-IDF) electrophoresis as follows: Combined sample is run on 1% agarose gel electrophoresis in forward direction at 6 V/cm. Section of the gel containing a lane of standards (1 Kb+, Life Technologies; Rockville, Md.) and a lane of the DNA sample is excised, stained with SYBR GOLD™ and bands are visualized on Dark Reader Blue Light Transilluminator (Clare Chemical Research). The region of the gel bellow 700 bp is then cut out and removed. The remaining portion of the stained slice is aligned back with the unstained gel and used as a landmark for cuffing and removing of the fraction containing undesired small molecules. The unstained gel is run in reverse direction in at 6 V/cm for 85% of the forward time. After electrophoresis is complete the gel is stained with SYBR GOLD™. The band PENTAmer molecules now focused in a narrow region is excised and eluted at 5,000×g for 15 min using Ultrafree-DA gel extraction device (Milipore). Sample is diluted between 10,000 and 50,000-fold and used as template for re-amplification by PCR using individual kernel primers and universal adaptor B1 primer (primer 18). FIG. 25 shows an example of two $E.$ $coli$ genomic sequences amplified after size fractionation. Essentially all short fragments are eliminated in the second amplifications step.

PCR amplified samples are purified by Qiaquick PCR purification kit (Qiagen; Valencia, Calif.), eluted in 30 ml of EB buffer (Qiagen; Valencia, Calif.) and sequenced as described in Example 6.

Three failed samples from the first approach are resequenced through the Visible Genetics sequencing protocol, using the size-fractionated library as template. One sequence had a read length of 259 bases (Phred >20), a second sequence produced a read length of less than 100 bases at Phred value of >20. However, this sample (Table VIII, sample S31) was base called by the Visible Genetics software and had a contig of 346 bases matching 99% the published $E.$ $coli$ database sequence. The third sequence did not yield useful sequence data but was among the samples successfully sequenced through the MegaBACE protocol directly from the primary library (Table VIII, sample S13). The only sample producing ambiguous result in both sequencing attempts (Table VIII, sample S31) not only contains a cluster of five Sau3A I restriction sites within 0.8–1 Kb upstream of the kernel but also the 12 bases at its 5' terminus are part of repetitive element in the $E.$ $coli$ genome.

To test the overall performance of sequencing following size fractionation, fourteen additional samples from the size-fractionated pool were analyzed on the MegaBACE 1000 sequencer. Seven samples had an average read length of 575 bases (Phred >20) and seven had red lengths under 100 bases (Phred >20) thus yielding a success rate of only 50%.

In summary, combining the three approaches for sequencing $E.$ $coli$ genomic sequences from primary PENTAmer library of partial Sau3A I restriction digest: (i) direct sequencing after PCR from primary library with kernel and universal primer, (ii) nested kernel primers during cycle sequencing, and (iii) size-fractionation of pooled PCR amplicons, followed by PCR re-amplification, collectively yielded 100% success rate for the 50 *E. coli* sequences analyzed in Example 6 and Example 7 with only one ambiguous sequence.

Example 8

Preparation and Analysis of Secondary PENTAmer Library from *E. Coli* Sau3A I Partial Genomic Digest This example describes the preparation of secondary library derived from the PENTAmer *E. coli* BamH I library shown in Example 5. The library is prepared by PCR amplification of the primary library in the presence of dUTP and biotinylated B adaptor oligonucleotide, capture of the biotinylated strand on magnetic beads and blocking of its 3' end by transfer of dideoxy adenosine with terminal transferase.

One microliter of primary PENTAmer *E. coli* Sau3A I Genomic library beads (appr. 1% of the total library) is used as PCR template with biotinylated adaptor B1 primer (primer 19) and adaptor A3 PCR primer (primer 14) in the presence of 0.2 mM of each dNTP and 0.3 mM dUTP. After 23 cycles at 94° C. for 10 sec and 68° C. for 75 sec, eleven reaction tubes of 25 µl are combined. The sample is purified using Qiaquick PCR purification kit (Qiagen; Valencia, Calif.) and eluted in 100 µl of EB buffer (10 mM Tris-HCl, pH 8.5. Library DNA is further size-fractionated by RF-IDF electrophoresis. Sample is loaded on preparative 0.7% pulse-field grade agarose gel (Bio Rad) along with 1 Kb+ ladder (Life Technologies; Rockville, Md.). Electrophoresis in the forward direction is performed at 6 V/cm in interrupted mode (60 sec on, 5 sec off) for 1.4 hours. A section of the gel containing a lane of standards and a lane of the DNA sample is excised, stained with SYBR GOLD™ and bands are visualized on Dark Reader Blue Light Transilluminator (Clare Chemical Research). The DNA size region smaller than 1 Kb is cut out and removed. The remaining portion of the stained slice is aligned back with the unstained gel and used as landmark for cutting and removing of the fraction containing molecules below 1 Kb in size. The unstained gel is then run in reverse direction in interrupted field of 6 V/cm (60 sec on, 5 sec off) for 1.1 hour. After electrophoresis is complete, the gel is stained with SYBR GOLD™. The bands of interest focused in sharp narrow region are cut out and recovered from the agarose using Gel Extraction kit (Qiagen; Valencia, Calif.) in 10 mM Tris-HCl pH 8.5.

Seven hundred and fifty micrograms of streptavidin coated DYNABEADS™ M-280 (Dynal) are prewashed with TE-L buffer and resuspended in 2×BW buffer (20 mM Tris-HCl, 2 mM EDTA, 2 M NaCl, pH 7.5). The DNA sample is mixed with equal volume of beads suspension in 2×BW buffer and placed on rotary shaker for 1 hr at room temperature. The beads are bound to magnet and washed with 3×100 ml each of 1×BW buffer and TE-L buffer. Non-biotinylated DNA is removed by incubating the beads with 100 µl of 0.1 N NaOH for 5 min at room temperature. Beads are washed with 100 µl of 0.1 N NaOH, neutralized by washing with 5×100 ml of TE-L buffer, and resuspended in 66 µl of water.

To prevent free 3' termini from mispriming during primer extension, library beads are supplemented with 1× terminal transferase buffer (Roche; Nutley, N.J.), 0.25 mM $CoCl_2$, 0.1 mM ddATP, and 60 units of terminal transferase (NEB) in a final volume of 100 µl and reaction is carried out at 37° C. for 30 min. Beads are washed with 2×100 µl each of TE-L buffer 1×BW buffer, resuspended in 120 µl of storage buffer (0.5 M NaCl, 10 mM Tris-HCl, 10 mM EDTA, pH 7.5) and stored at 4° C.

Example 9

Multiplexed Linear Amplification of *E. Coli* Genomic Kernel Sequences from Secondary *E. Coli* PENTAmer Library Derived from Sau3A I Partial Digest This Example describes the amplification of three *E. coli* sequences in multiplexed linear amplification cycling reaction from secondary dU-containing Sau3A I PENTAmer library bound to magnetic beads, prepared as described in Example 8. Linear amplification is performed in the presence of 3'-blocked oligonucleotide annealing in the region of adaptor B to prevent newly synthesized single stranded molecules from self-priming. The second strand is extended by adding an excess of unblocked adaptor B primer. After removal of magnetic beads full-size products are purified by size fractionation, dU-containing molecules are destroyed by treatment with uracil DNA glycosylase and the sequences enriched by multiplexed linear amplification are segregated by PCR amplification with individual kernel primers and universal adaptor B1 primer.

Three oligonucleotides specific for *E. coli* kernel sequences adjacent to Sau3A I restriction sites are mixed in 1×AdvanTaq+buffer (Clontech; Palo Alto, Calif.) at final concentration of 40 nM each with 100 nM of 3'-blocked oligonucleotide (primer 17), 10 mM each dNTP, 10 ml of secondary dU containing Sau3A I PENTAmer library beads (Example 8) and 1×AdvanTaq+hot start DNA polymerase in final volume of 60 µl. Identical control reaction is assembled which lacks DNA polymerase. After initial denaturing at 94° C. for 1 min, samples are subjected to 29 cycles at 94° C. for 10 sec, and 68° C. for 75 sec. Adaptor B1 PCR primer (primer 18) is added at final concentration of 330 nM and two more cycles are performed at 94° C. for 10 sec, and 68° C. for 75 sec to fill up second strand.

Samples are subjected to electrophoresis on 1% agarose gel, stained with Sybr Gold and bands are visualized on Dark Reader Blue Light Transilluminator (Clare Chemical Research). The bands of 1 Kb are cut out and eluted at 5,000×g for 15 min using Ultrafree-DA gel extraction filter (Millipore; Bedford, Mass.). After 30-fold dilution in 10 mM Tris-HCl, pH 7.5, aliquots of 50 ml are supplemented with one unit of heat labile uracil DNA glycosylase (UDG, Roche; Nutley, N.J.) and incubated for 45 min at 20° C. UDG is heat-inactivated at 95° C. for 10 min and samples are analyzed by PCR.

Figure 26:
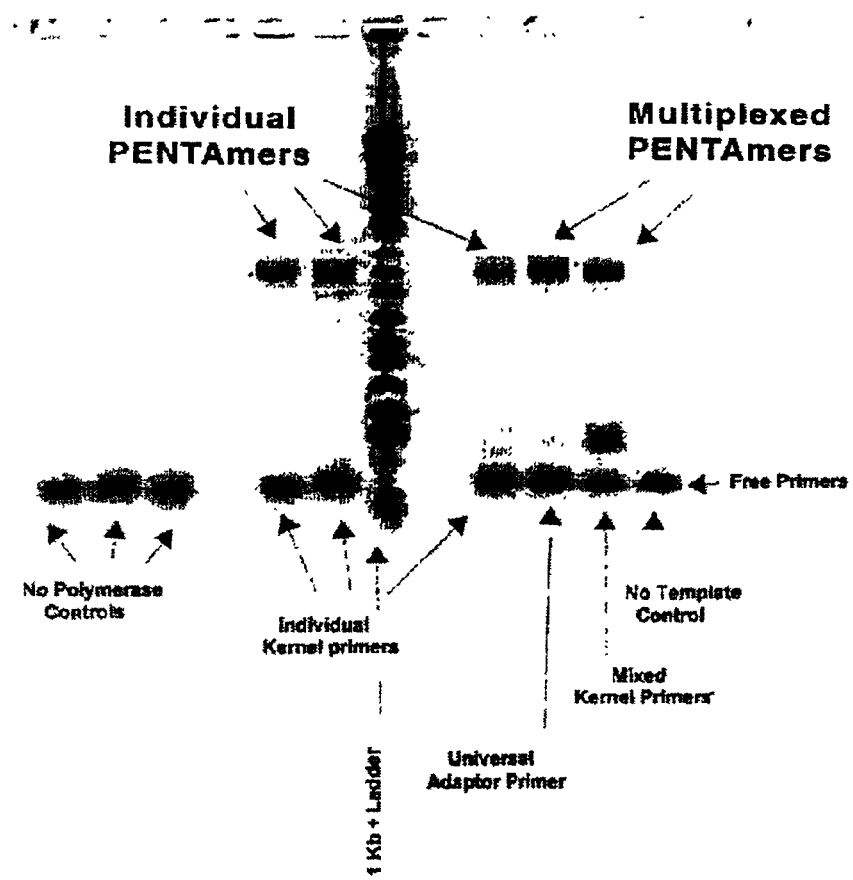
FIG. 26 demonstrates PCR analysis of three kernel sequences selected by multiplexed linear amplification from secondary E. coli PENTAmer library derived from Sau3A I partial digest.

One microliter of each sample is applied as template for PCR with 200 nM of each individual kernel primer used for linear amplification and 200 nM universal adaptor B1 primer (primer 18). In multiplexed mode, a mixture of the three primers at 80 nM each and 200 nM of universal adaptor B1 primer (primer 18) are used. PCR samples are analyzed on 1% agarose gel after staining with Sybr Gold. FIG. 26 shows the result of this analysis. All three sequences are amplified as full-size fragments. The products of the PCR amplification are purified by Qiaquick PCR purification (Qiagen; Valencia, Calif.) eluted in 30 µl 10 mM Tris-HCl, pH 8.5 and aliquots containing 20–50 ng of DNA are sequenced with Thermo Sequenase Cy5.5 Dye Terminator Cycle Sequencing kit (Amersham Pharmacia Biotech) on OpenGene sequencing system (Visible Genetics) as described in Example 6 with the same kernel primers used in linear amplification and PCR. All three sequences are confirmed.

Example 10

Preparation and Analysis of PENTAmer Libraries from Human Genomic DNA After Complete BamH I or Partial Sau3A I Digestion This example describes the preparation of primary human genomic PENTAmer libraries bound to magnetic beads and their amplification with universal adaptor primers.

Aliquots of 10 micrograms of genomic DNA prepared by standard purification from fresh human lymphocytes are digested with 140 units of BamH I (NEB) for 6 hours at 37° C. or with 20 units of Sau3A I (New England Biolabs; Beverly, Mass.) for 35 min at 37° C. Twenty μg of BamH I or 50 μg of Sau3A I digested DNA are treated with 3 units/mg of SAP (Roche; Nutley, N.J.) for 20 min at 37° C. SAP is heat-inactivated for 15 min at 65° C. and DNA is purified by extraction with equal volume of phenol:chloroform:isoamyl alcohol (25:24:1) and precipitation with ethanol. DNA fragments are size-fractionated by preparative RF-IDF in 0.75% pulse-field grade agarose (Bio-Rad; Hercules, Calif.) gel. Electrophoresis in forward direction is performed at 6 V/cm in interrupted mode (60 sec on, 5 sec off) for 2 hours. After cutting the section of the gel containing DNA molecules below 2 Kb, reverse field of 6 V/cm (60 sec on, 5 sec off) is applied for 1.7 hours. Bands are excised and recovered from the agarose by Gel Extraction Kit (Qiagen; Valencia, Calif.) in 10 mM Tris-HCl pH 8.5.

Samples are mixed with 1.2 pmoles (BamH I) or 6 pmoles (Sau3A I) of pre-assembled BamH I nick-translation adaptor (adaptor A3 consisting of primers 11, 12, and 13) and after heating at 65° C. for 1 min ligation is carried out at 20° C. for 2.5 hours with 4,800 units of NEB T4 ligase (BamH I) or 11,200 units of NEB T4 ligase (Sau3A I). To remove ligase and excess free adaptor the sample is extracted with equal volume of phenol:chloroform:isoamyl alcohol (25:24:1), mixed with ¼ vol of QF buffer (240 mM NaCl, 3% isopropanol, and 10 mM Tris-HCl, pH 8.5 final concentrations) in a volume of 400 μl and centrifuged at 200×g to a volume of 100 μl in Microcon YM-100 filtration units. The samples are washed 3 times with 400 μl of TE-L buffer at 200×g and concentrated to a final volume of 65 μl (BamH I) or 120 ml (Sau3A I).

The purified samples are subjected to nick-translation with 19 units (BamH I) or 38 units (Sau3A I) of wild type Taq polymerase in 1× Perkin Elmer (Norwalk, Conn.) PCR buffer buffer II containing 4 mM $MgCl_2$ and 200 mM of each dNTP in final volume of 120 μl (BamH I) or 240 μl (Sau3A I) for 5 min at 50° C. Reactions are stopped by addition of EDTA to a final concentration of 20 mM and products are analyzed on 6% TBE-urea gel (Novex; San Diego, Calif.) after staining with SYBR GOLD™.

Samples are supplemented with blocking oligonucleotide complementary to the nick-translation template strand at the region of the adaptor (primer 15) at a final concentration of 1 mM, denatured by boiling at 100° C. for 3 min and cooled on ice for 5 min. Eighteen hundred micrograms of streptavidin coated Dynabeads M-280 (Dynal) are prewashed with TE-L buffer and resuspended in 2× BW buffer (20 mM Tris-HCl, 2 mM EDTA, 2 M NaCl, pH 7.5). Denatured DNA samples are mixed with equal volume of beads (⅓ of the total beads with BamH I and ⅔ with Sau3A I sample) in 2× BW buffer and placed on rotary shaker for 1.5 hr at room temperature. The beads are bound to magnet and washed 2× with 100 μl each of 1×BW buffer and TE-L buffer. Nonbiotinylated DNA is removed by incubating the beads in 100 ml of 0.1 N NaOH for 5 min at room temperature. Beads are washed with 100 μl of 0.1 N NaOH, neutralized by washing with 5×100 μl of TE-L buffer, and resuspended in TE-L buffer.

Library DNA samples are then processed for ligation with adaptor B. To minimize formation of adaptor A-B dimers on magnetic beads the beads suspensions are supplemented with 1× T4 ligase buffer (NEB) and incubated with 50 pmoles of 3'-blocked oligonucleotides (primers 20 and 21) as described in Example 5. The suspensions are heated for 1 min at 60° C., cooled to room temperature and incubated for 10 min at room temperature to anneal the blocking oligonucleotides to residual adaptor A molecules bound to magnetic beads. Beads are then washed with 50 μl of 1× T4 ligase buffer and resuspended in 50 μl of the same buffer. The samples are supplemented with 40 pmoles (BamH I) or 80 pmoles (Sau3A I) of each adaptor B1 oligonucleotide (primers 16 and 17) in 1× T4 ligase buffer and 4000 units (BamH I) or 8000 units (Sau3A I) of T4 ligase (NEB) in final volume of 100 μl (BamH I) or 200 μl (Sau3A I). Ligation is performed at room temperature for 3.5 hours on end-to-end rotary shaker to keep the beads in suspension. Beads are bound to magnet, washed with 2×100 μl each of 1×BW buffer and TE-L buffer and nonbiotinylated DNA is removed by incubating the beads in 100 μl of 0.1 N NaOH for 5 min at room temperature. Beads are washed with 100 μl of 0.1 N NaOH, neutralized by washing with 5×100 μl of TE-L buffer, resuspended in 160 μl (Bam H I) or 280 μl (Sau3A I) of SB buffer and stored at 4° C.

Figure 27:
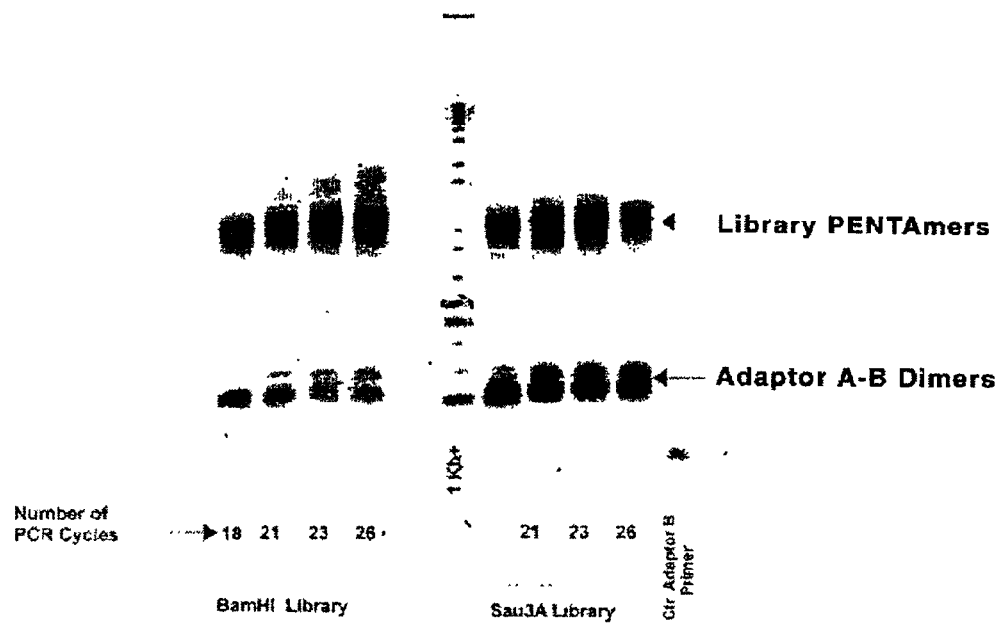
FIG. 27 shows PCR amplification of PENTAmer libraries prepared from human genomic DNA after partial Sau3A I or complete BamH I restriction digest.

FIG. 27 shows amplification of the primary PENTAmer libraries from human genomic DNA prepared by complete BamH I or partial Sau3AI digestion. Magnetic beads containing library DNA are prewashed in water and 0.5 μl of each library used as template for PCR amplification with 100 nM of universal adaptor A3 and adaptor B I primers (primers 13 and 18) in final volume of 25 μl. After initial denaturing the indicated number of cycles are carried out at 94° C. for 10 sec and 68° C. for 75 sec. Ten μl aliquots are separated on 1% agarose gel and visualized on Fluor S MultiImager (Bio Rad) after staining with Sybr Gold.

This example demonstrates that primary PLEX-imer libraries can be prepared and amplified from eukaryotic genomic DNA.

Example 11

Preparation and Analysis of Single-Stranded Circular PENTAmer Libraries from from Human Genomic DNA After Complete BamH I or Partial Sau3A I Digestion This example describes the preparation of circular single-stranded derivatives of primary human genomic Sau3AI and BamH I libraries described in Example 10. These circular libraries are used as template for reverse PCR amplification with kernel human sequences keeping intact the adaptor tags which will allow simultaneous analysis of single nucleotide polymorphic (SNP) regions in multiple individuals.

Magnetic beads containing primary human BamH I or Sau3A I library DNA (Example 10) are pre-washed in water and 0.5 μl of each library is used as template for PCR amplification in 16 individual tubes for each library with 200 nM of 5'-biotinylated adaptor B1 primer (primer 19) and 5'-phosphorylated adaptor A3 primer (primer 23) in final volume of 50 ml. After initial denaturing at 95° C., eighteen cycles of PCR are performed at 94° C. for 10 sec and 68° C. for 75 sec. Beads are removed on magnet and the individual PCR samples for each library are pooled.

Samples are purified free of primers and Taq polymerase on Qiaquick PCR purification filters (Qiagen; Valencia, Calif.) and eluted in 150 μl of 10 mM Tris-HCl, pH 8.5. DNA is polished with 4 units of T4 DNA Polymerase (Roche; Nutley, N.J.) in the presence of 200 nM of each dNTP for 30 min at 25° C. DNA samples are purified on Qiaquick PCR purification filters (Qiagen; Valencia, Calif.), supplemented with ¼ volume of QF buffer (240 mM NaCl, 3% isopropanol, and 10 mM Tris-HCl, pH 8.5 final concentrations) in a volume of 400 μl, and centrifuged at 200×g to a volume of 100 μl in Microcon YM-100 filtration units. The samples are washed 3 times with 400 μl of TE-L buffer at 200×g and concentrated to a final volume of 130 μl.

Sixteen hundred micrograms of streptavidin-coated DYNABEADS M-280 (Dynal) are prewashed with TE-L buffer and resuspended in 2×BW buffer (20 mM Tris-HCl, 2 mM EDTA, 2 M NaCl, pH 7.5). Denatured DNA samples are mixed with equal volume of beads in 2×BW buffer and placed on rotary shaker for 1 hr at room temperature. The beads are bound to magnet and washed 2× with 100 ml each of 1×BW buffer and TE-L buffer. Beads are resuspended in 100 μl of SB buffer and stored at 4° C.

One half of the Sau3A I library DNA is incubated with 20 μl of 0.1 N NaOH for 5 min at room temperature. Eluted non-biotinylated DNA strands are neutralized with 10 ml of 0.2 N HCl and 3 μl of 1 M Tris-HCl, pH 8.0. Sample is diluted to 100 μl with water and any residual biotin-containing DNA is removed by incubation with 200 μg of fresh streptavidin beads for 30 min at room temperature. Single-stranded DNA is purified on Qiaquick PCR purification filters (Qiagen; Valencia, Calif.) and eluted in 60 μl of 10 mM Tris-HCl, pH 8.5.

Sau3A I library single-stranded DNA is incubated with 3'-C7 amino blocked bridging oligonucleotide (primer 24) bringing together adaptor A3 (5' terminus) and adaptor B1 (3'-terminus) to form circular molecules by ligation. DNA is aliquoted into four 200 ng samples and incubated with bridging oligonucleotide (primer 24) at 0, 15, 75, or 150 μl final concentration in 1×Tsc ligase buffer (Roche; Nutley, N.J.) and final volume of 30 μl. After initial denaturing at 95° C. for 1 min, ligation is performed for 24 cycles at 94° C. for 20 sec and 65° C. with 5 units of Tsc DNA ligase (Roche; Nutley, N.J.).

Figure 28:
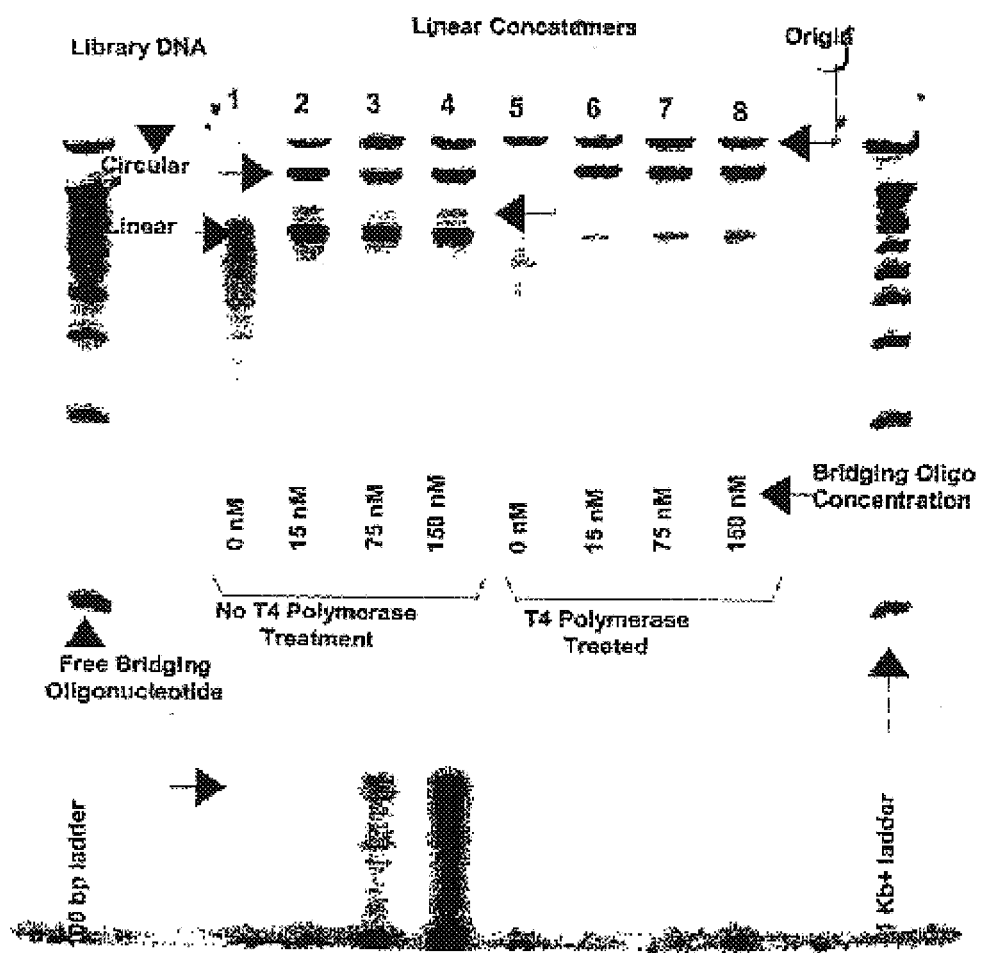
FIG. 28 shows circularization of single-stranded human genomic DNA Sau3A I PENTAmer library.

Samples are split into two aliquots of 15 μl and one half is treated with 0.7 units of T4 DNA polymerase (Roche; Nutley, N.J.) for 1 hr at 37° C. in the absence of dNTPs to destroy linear DNA molecules. The remaining half is left untreated. Aliquots of each treated and untreated sample are analyzed on 6% TBE urea acrylamide gel (Novex; San Diego, Calif.) after staining with SYBR GOLD™ (Molecular Probes; Eugene, Oreg.). FIG. 28 shows the result of this analysis. In the samples receiving bridging oligonucleotide, a low mobility band appears corresponding to circularized PENTAmer molecules. Close to 50% of the single-stranded DNA is converted to circular form in the samples having high concentration of bridging oligonucleotide. A faint band with intermediate mobility also appears in the samples ligated in the presence of bridging oligonucleotide, presumably corresponding to linear concatamers. Unlike the circular form, both linear species as well as the bridging oligonucleotide are sensitive to T4 3'-exonuclease activity since considerable reduction in the intensity of these bands occurs after T4 DNA polymerase treatment (compare lanes 5, 6, 7, and 8 with 1, 2, 3, and 4).

Figure 29:
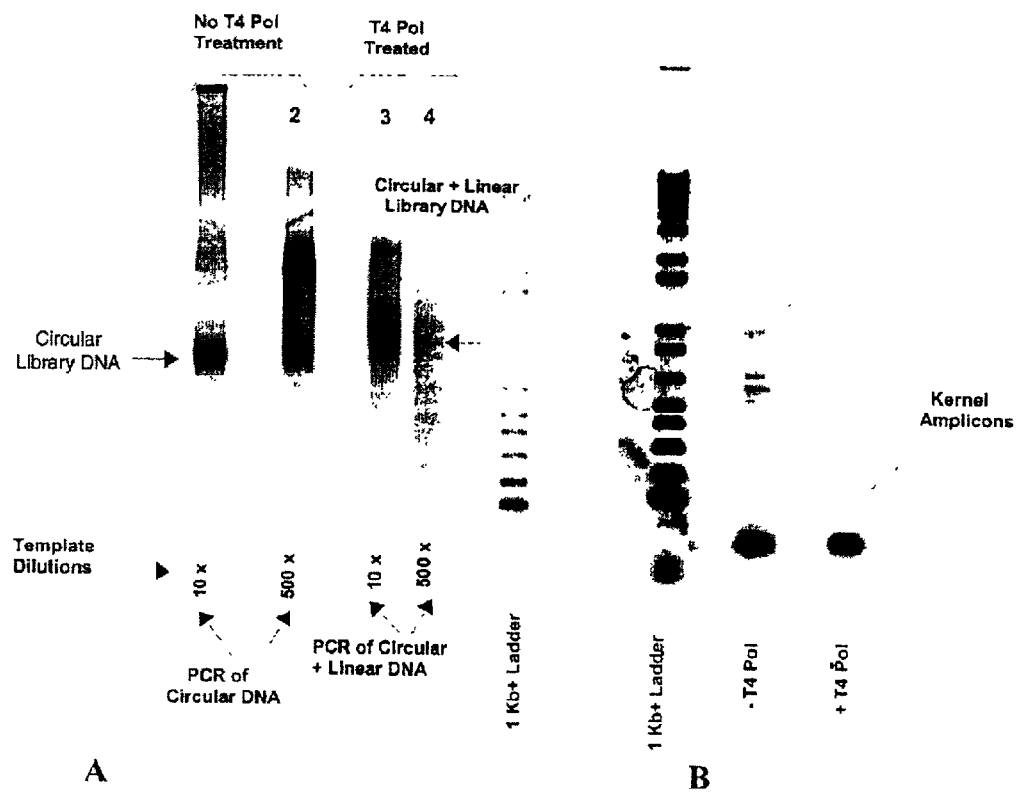
FIG. 29 demonstrates PCR amplification of single-stranded circular Sau3A I human PENTAmer library and a kernel sequence.

To test the efficiency of amplification from human circular Sau3A I library the remainder of the samples analyzed on FIG. 28 are purified by ethanol precipitation and dissolved in 20 μl of TE buffer. One microliter aliquots of 10-fold or 500-fold dilutions of the samples ligated in the presence of 75 nM bridging oligonucleotide are then used as template for amplification in 30 cycles of PCR. Primers annealing at adaptor A3 which will amplify only circular DNA molecules (primers 25 and 26) or primers which anneal at adaptor A3 and adaptor B 1 and will amplify both circular and linear molecules (primers 18 and 26) are used. FIG. 29A shows that the amount of circular DNA molecules before treatment with the exonuclease activity of T4 polymerase is higher than the amount of circular and linear DNA after such treatment combined (compare lanes 2 and 4). This result independently validates the formation of circular single-stranded library molecules. FIG. 29B shows an attempt for amplification of kernel human sequence in circular mode with a pair of primers specific for exon 10 of the human tp53 gene. The same template as in the experiment on FIG. 29A but without dilution was used before or after treatment with exonuclease in 35 cycles of PCR amplification. The products of such amplification would be expected to have relatively uniform size distributed around the average length of termination of nick-translation of PENT molecules in the parental primary library. However, amplicons of multiple discrete lengths varying from 200 bp to 1 Kb are amplified, indicating more complex events compared to kernel amplification from linear library in nested mode (Example 12).

Example 12

Amplification of Human Genomic Kernel Sequences from Primary PENTAmer Libraries of Complete BamH I or Partial Sau3A I Digests by Nested PCR This example shows amplification of genomic kernel sequences from primary human BamHI and Sau3A I libraries by nested PCR. In the first PCR reaction limited number of cycles are performed using the distal adaptor B1 primer (primer 18) and a kernel specific primer up to 500 bp downstream of BamH I or Sau3A I restriction sites. Following purification of the amplicons second PCR is performed with the proximal adaptor B1 primer (primer 22) and nested kernel primers.

Figure 30:
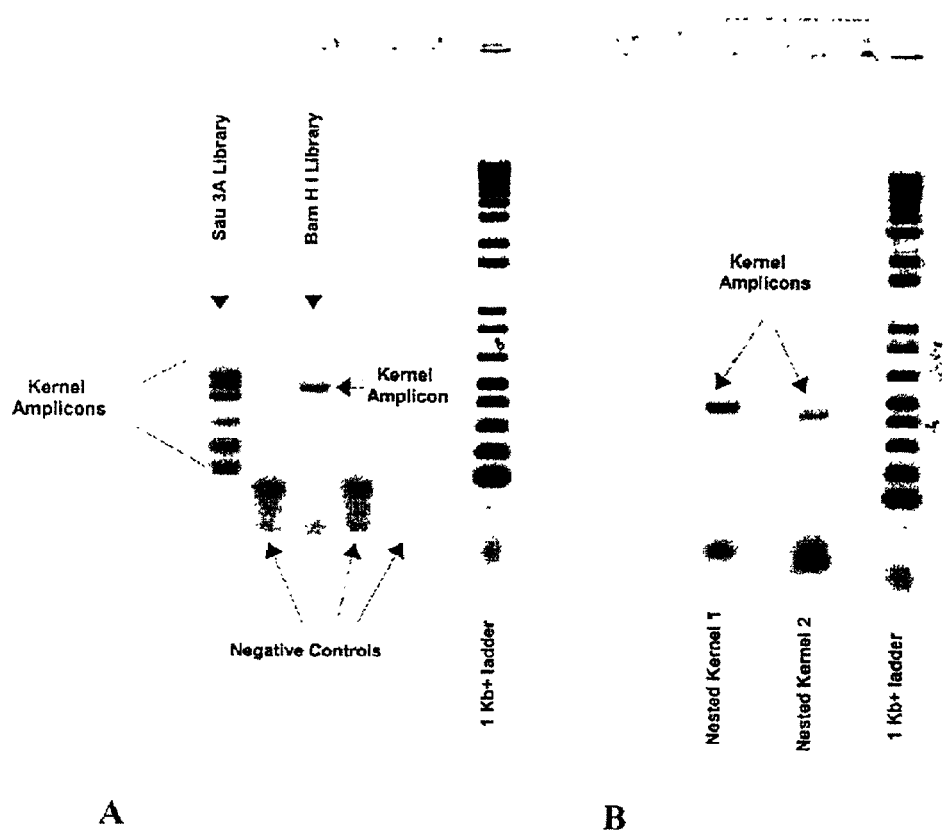
FIG. 30 shows nested PCR amplification of kernel human genomic sequence from primary BamH I and Sau3A I PENTAmer libraries.

One microliter of library beads of BamH I or Sau3A I primary human libraries prepared as described in Example 10 are used as template for PCR amplification with 50 nM distal adaptor B1 primer (primer 18) and 200 nM kernel primer specific for exon 10 of the human tp53 gene in two aliquots of 25 ml each. After initial denaturing at 94° C. for 1 min samples are subjected to 12 cycles at 94° C. for 10 sec and 68° C. for 75 sec. The two aliquots are combined and DNA samples are purified through Qiaquick PCR purification kit (Qiagen; Valencia, Calif.) and eluted in 50 μl of EB buffer (10 mM Tris-HCl, pH 8.5). One microliter aliquots of the purified DNA samples from the first amplification are used as templates in second PCR with 50 nM proximal B1 adaptor primer (primer 22) and 200 nM nested kernel primer specific for exon 10 of the human tp53 gene which anneals 45 bp downstream of the kernel primer used in the first PCR amplification. After initial denaturing at 94° C. for 1 min, samples are subjected to 33 cycles at 94° C. for 10 sec, and 68° C. for 75 sec and 10 μl aliquots are analyzed on 1% agarose gel after staining with SYBR GOLD™ (FIG. 30A). Multiple discrete bands are amplified from primary library of Sau3A I partial digest and a single band of approximately 500 bp from the library of BamH I complete digest respectively. In addition, a second nested kernel primer annealing 83 bp downstream of the primer in the first PCR is used with BamH I template under the conditions for nested amplification described above. Comparison of the two nested kernel primers for BamH I template (FIG. 30B) shows that, as expected, single amplicons differing by approximately 50 bp are produced. The PCR product of nested primer 1 (FIG. 30B; lane 1) is purified by Qiaquick PCR purification kit (Qiagen; Valencia, Calif.) and used as template for sequencing with both nested primers, 1 and 2 with DYEnamic ET terminator reagent mix (Amersham Pharmacia Biotech) and analyzed on MegaBACE 1000 capillary sequencing system (Amersham Pharmacia Biotech) as described in Example 6.

Figure 31:
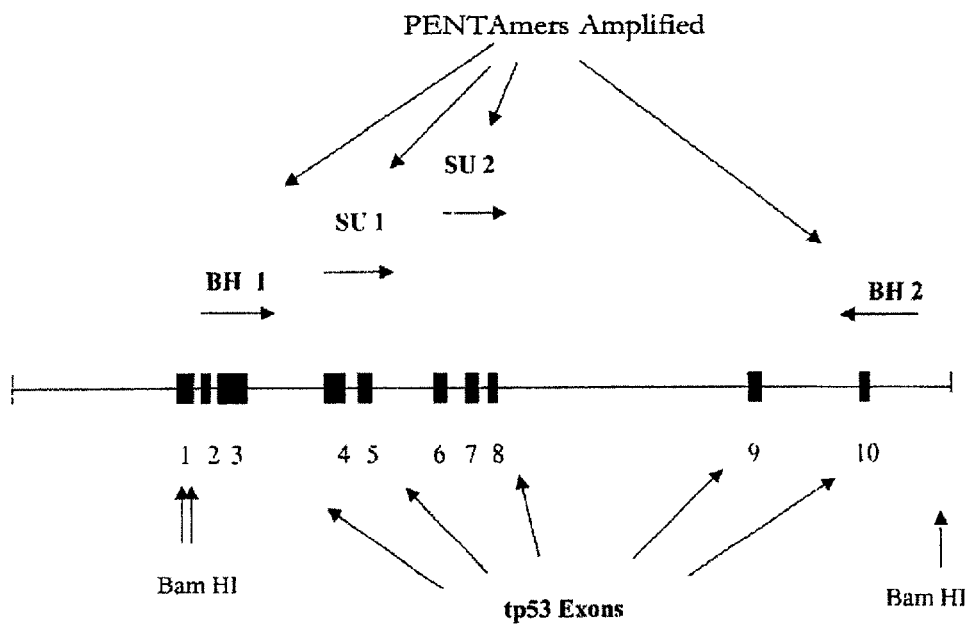
FIG. 31 illustrates schematic presentation of regions in the 10 Kb human tp53 gene amplified by nested PCR from primary BamH I and Sau3A I libraries.

Additional sequences are amplified by PCR with adaptor B1 universal primers (primers 18 and 22) and the following pairs of nested primers: one specific for PENTAmer covering exons 2 and 3 of the human tp53 gene using BamHI library as template, and two covering exons 4 and 5, and 6, 7, and 8 respectively, using Sau3A I library as template (FIG. 31). Primary and secondary (nested) PCR rounds are carried out as described above. In the cases where multiple fragments are obtained (Sau3A I) the bands are excised from the agarose gel, extracted with Ultrafree DA gel extraction kit (Millipore; Bedford, Mass.) and appropriate dilutions are used as templates for re-amplification in individual PCR reactions with the same primers used in secondary PCR. The amplification products are purified with Qiaquick PCR purification kit (Qiagen; Valencia, Calif.) and sequenced as above with the corresponding nested primers used in PCR.

An average read length of 509 bases is achieved with the four human tp53 samples sequenced at a quality index of 94 (accuracy of 94%) using the Cimmaron 1.53 Slim Phredify Basecaller algorithm (Amersham Pharmacia Biotech).

This example demonstrates that kernel genomic sequences can be amplified after nested PCR from primary genomic human PENTAmer libraries prepared by complete or partial restriction digestion.

REFERENCES

The following references, to the extent that they provide exemplary procedural or other details supplementary to those set forth herein, are specifically incorporated herein by reference.

PUBLICATIONS

Ardrey, Electrospray Mass Spectrometry, Spectroscopy Europe, 4, 10–18, 1992.
Arnold, C. and I. J. Hodgson. 1991. Vec-torette PCR: a novel approach to genomic walking. PCR Methods Appl. 1:39–42.
Berg et al. in Automated DNA sequencing and analysis by Adams, Fields, and Venter. Academic Press (1994)
Berkenkamp et al., Science, 281:260–2, 1998
Cantor and Smith Genomics, John Wiley & Sons, Inc., N.Y., 1999.
Cheng, S. et al. (1994) Nature, 369, 684–685. long range PCR
Cormack and Somssich Gene 194 (1997) 273–276
Crain, Mass Spectrometry Reviews, 9: 505–554, 1990.
Dieffenbach and Dveksler. PCR Primer CSHL Press 1995.
Devon, R. S., Porteous, D. J., and Brookes, A. J. (1995) Nucleic Acids Res. 23, 1664–1645.
Fenn et al., J. Phys. Chem. 88, 4451–59, 1984.
Fodor, et al., Nature; 364(6437):555–6, 1995.
Forster, Ann. Phys., 2:55–75, 1948.
Freifelder, et al. Anal Biochem, 123(1):83–5, 1982
Frohman, In: PCR Protocols: A Guide To Methods And Applications, Academic Press, N.Y., 1990.
Grant, et al. Biochemistry, 35(38):12313–9, 1996.
Guilfoyle, et al. Nucleic Acids Research 25:1854–1858 (1997)
Hacia, et al., Nature Genet., 14:441–449, 1996.
Hagiwara, K. and Harris Nucleic Acids Research 24:2460–2461 (1996)
Harrison, et al., BioTechniques 22:650–653 (1997)
Higuchi et al., Biotechnology 10:413–417 1992
Hillenkamp, et al., Anal Chem., 63(24):1193A–1203A, 1991.
Holmstrom et al., Anal. Biochem. 209:278–283, 1993.
Hunkapiller, et al., Science, 254(5028):59–67. 1991
Innis, et al., PCR Protocols, Academic Press, Inc., San Diego, 1990
Jones, D. H. and S. C. Winistorfer, BioTechniques 15:894–904, 1993.
Jones, D. H. and S. C. Winistorfer, Nucleic Acids Res. 20:595–600, 1992.
Koster et al. Biomedical Environmental Mass Spectrometry, 14: 111–116, 1987.
Kwoh, et al., Proc Natl Acad Sci USA. 1986(4):1173–7, 1989.
Lee, et al., Nuc. Acids Res. 21, 3761–3766, 1993.
Liao et al, Analytical Biochemistry, 253:137–139, (1997).
Lin, et al., Analytical Biochemistry 231:449–452, 1995.
Lukyanov et al. Nucleic Acids Research 24:2194–2195 (1996).
Makarov, et al., 1997
Macrae and Brenner (1994) Genomics 24:176–178
Maniatis T, Fritsch E F and Sambrook J. (1989). Molecular cloning: A laboratory manual. Cold Spring Harbour Laboratory: Cold Spring Harbour, N.Y.
McCombie et al. Methods: Companion Methods Enzymology 3:33–40 (1991).
Methods in Enzymology, Vol. 193: "Mass Spectrometry" (McCloskey, ed.), Academic Press, New York, 1990.
Meyer, et al. Nature, 278(5702):365–7, 1979.
Nakamaye et al. Nucleic Acids Research 16:9947 (1988)
Newton, et al. Nucl. Acids Res. 21:1155–1162, 1993.
Nonisotopic DNA Probe Techniques, Academic Press, Inc., pgs. 311–352, 1992.
Ochman et al. Genetics 120:621–623 (1988).
Ohara et al., Proc. Natl. Acad. Sci. USA, 86:5673–5677, 1989.
Padegimas et al. Analytical Biochemistry, 260, 149–153, 1998.
Pease et al., Proc. Natl. Acad. Sci. USA, 91:5022–5026, 1994.
Primrose Principles of Genome Analysis, Second Edition, Blackwell Science, 1998.
Rasmussen et al., Anal. Biochem, 198:138–142, 1991.
Riley, J., Butler, R., Ogilvie, D., Finniear, R., Jenner, D., Powell, S., Anand, R., Smith, J. C., and Markham, A. F. (1990) Nucleic Acids Res. 18, 2887–2890
Richterich and Church, Method Enzymol., vol 218, 187–222 (1993)
Rosenthal, A., and Jones, D. S. (1990) Nucleic Acids Res. 18, 3095–3096.
Rudi et al. (1999) Biotechniques 27:1170–1177
Running et al., BioTechniques 8:276–277, 1990.
Sambrook et al., "Molecular Cloning," A Laboratory Manual, 2d Ed., Cold Spring Harbor Laboratory Press, New York, 13.7–13.9:1989.

Schram, *Methods* Biochem *Anal.*, 34: 203–287 1990.
Shoemaker et al., *Nature Genetics* 14:450–456, 1996.
Smith et al., *Anal. Chem.* 62, 882–89, 1990.
Siebert et al. *Nucleic Acids Res.* 23, 1087–1088, 1995.
Smith, D. R. (1992) *PCR Methods Appl.*, 2, 21–27.
Sterky et al. Journal of Biotechnology 60 (1998) 119–129
Tabor, et al., *Proc Natl Acad Sci USA.*, 84(14):4767–71, 1987.
Unrau, P. and Deugau, K. (1994) *Gene,* 145, 163–169.
Vos et al., Nucleic Acids Research 23:4407–4414 (1995).
Walker et al. (1992a) PNAS 89:392–396
Walker et al. (1992b) Nuc. Acids Res. 20: 1691–1696.
Williams et al., *Science,* 246: 1585–87, 1989
Xu et al. Anal. Chem. Vol 69, 3595–3602, 1997
Zhang, et al. Gurr Gene 253 (2000) 145–150.

PATENTS

U.S. Pat. No. 4,942,124
U.S. Pat. No. 4,683,194
U.S. Pat. No. 4,710,465
U.S. Pat. No. 5,075,216
U.S. Pat. No. 5,143,854
U.S. Pat. No. 5,149,625
U.S. Pat. No. 5,424,186
U.S. Pat. No. 5,366,877
U.S. Pat. No. 5,547,861
U.S. Pat. No. 5,578,832
U.S. Pat. No. 5,599,668
U.S. Pat. No. 5,610,287
U.S. Pat. No. 5,837,832
U.S. Pat. No. 5,837,860
U.S. Pat. No. 5,843,651
U.S. Pat. No. 5,861,242
U.S. Pat. No. 6,027,913
U.S. Pat. No. 6,045,994
U.S. Pat. No. 6,124,120
EP 0 655 506 B1
Japanese Patent No. 59-131909
WO 88/10315
WO 89/06700
WO 90/14148
WO 96/21144
WO 98/1112
WO 98/15644
WO 00/18960

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

We claim:

1. A method of producing a consecutive overlapping series of nucleic acid sequences from a DNA sample, comprising the steps of:
   (a) generating a first amplifiable nick translation product, wherein said nick translation of said first amplifiable nick translation product initiates from a known nucleic acid sequence in the DNA sample;
   (b) determining at least a partial sequence from said first nick translation product; and
   (c) generating at least a second amplifiable nick translation product, wherein said nick translation of said second amplifiable nick translation product initiates from the partial sequence of said first nick translation product.

2. A method of producing a library of consecutive overlapping series of nucleic acid sequences from a DNA sample comprising DNA molecules having a region comprising a known nucleic acid sequence, the method comprising the steps of:
   (a) digesting DNA molecules of the DNA sample with a first sequence-specific endonuclease to generate a plurality of DNA fragments;
   (b) generating a first amplifiable nick translation product, wherein said nick translation of said first amplifiable nick translation product initiates from the known nucleic acid sequence;
   (c) determining at least a partial sequence from said first nick translation product; and
   (d) generating one or more additional amplifiable nick translation products, wherein said nick translation of said one or more amplifiable nick translation products initiates from the partial sequence of a previous nick translation product.

3. The method of claim 2, wherein said method further comprises the step of digesting DNA molecules with at least a second sequence-specific endonuclease, wherein an overlapping nick translation product from the one or more additional nick translation products is generated from a DNA fragment from digestion with the first sequence-specific endonuclease or from digestion with the second sequence-specific endonuclease.

4. A method of producing a library of consecutive overlapping series of nucleic acid sequences, comprising the steps of:
   (a) obtaining a DNA sample comprising DNA molecules having a region comprising a known nucleic acid sequence;
   (b) partially cleaving the DNA molecules with a sequence-specific endonuclease to generate a plurality of DNA ends;
   (c) separating the cleaved DNA molecules;
   (d) generating a first amplifiable nick translation product, wherein said nick translation of said first amplifiable nick translation product initiates from a known nucleic acid sequence;
   (e) determining at least a partial sequence from said first nick translation product; and
   (f) generating one or more amplifiable nick translation products, wherein said nick translation of said one or more amplifiable nick translation products initiates from the partial sequence of a previous nick translation product.

5. The method of claim 4, wherein the separation of the cleaved DNA molecules is according to size.

6. The method of claim 5, wherein the size separation is by gel size fractionation.

7. The method of claim 4, wherein the nick translation products are amplified.

8. The method of claim 7, wherein the amplification of the nick translation product comprises polymerase chain reaction utilizing a first primer specific to a known sequence in the nick translation product and a second primer specific to an adaptor sequence of the nick translation product.

9. The method of claim 7, wherein at least one of the nick translation products is selectively amplified from the plurality of nick translation products.

10. The method of claim 7, wherein the nick translation product is single stranded.

11. The method of claim 4, wherein the partial cleavage of the DNA molecules comprises cleaving for a selected time with a frequently cutting sequence-specific endonuclease, wherein the sequence-specificity of the endonuclease is to three or four nucleotide bases.

12. The method of claim 4, wherein the partial cleavage of the DNA molecules comprises subjecting the DNA molecules to a methylase prior to subjection to a methylation-sensitive sequence-specific endonuclease.

13. The method of claim 9, wherein the selective amplification comprises:
   (a) introducing to said plurality of nick translation products a plurality of primers, wherein the primers comprise:
      (1) nucleotide base sequence complementary to an adaptor sequence in the nick translation product;

(2) an additional variable 3' terminal nucleotide; and
(3) a label;
(b) hybridizing the primers to their complementary nucleic acid sequences in the adaptor to form a mixture of primer/nick translate molecule hybrids; and
(c) extending from a primer having the 3' terminal nucleotide complementary to the nucleotide in the nick translate molecule, wherein the nucleotide is immediately adjacent to the adaptor sequence, wherein the hybridizing and extending steps form a mixture of unextended primer/nick translate molecule hybrids and extended primer/nick translate molecule hybrids.

14. The method of claim 13, wherein the method further comprises:
(a) binding of the mixture by the label to a support;
(b) washing the support-bound mixture to remove the nick translate molecules; and
(c) removing the support-bound extended molecule from the support.

15. The method of claim 13, the primer further comprises two or more variable 3' terminal nucleotides.

16. The method of claim 9, wherein the method further comprises separating the selectively amplified nick translate products by size.

17. The method of claim 16, wherein the size separation is by gel fractionation.

18. The method of claim 16, wherein the method further comprises a step of subjecting the size-separated nick translate molecules to an additional amplification step.

19. The method of claim 9, wherein the selective amplification step is by suppression PCR.

20. The method of claim 19, wherein the suppression PCR utilizes a primer comprising:
(a) a nucleic acid sequence for a primer specific for an adaptor sequence of the nick translate molecule; and
(b) nucleic acid sequence complementary to a region in a plurality of nick translate molecules, whereby the nucleic acid sequence is 5' to the sequence for a primer specific for an adaptor sequence of the nick translate molecule.

21. The method of claim 9, wherein the at least one selectively amplified nick translate product is amplified by primer extension/ligation reactions.

22. The method of claim 21, wherein the method further comprises immobilization of the nick translation molecules onto a solid support.

23. The method of claim 22, wherein the solid support is a magnetic bead.

24. The method of claim 21, wherein the primer extension/ligation reactions comprise:
(a) initiating and extending the primer extension reaction to form a primer extended molecule, wherein the reaction uses a first primer which is complementary to sequence in a subset of the plurality of nick translate molecules, wherein the complementary sequence of the nick translate molecule is adjacent to a first adaptor end of the nick translate molecule; and
(b) ligating an oligonucleotide to the 5° end of the extension product, wherein the oligonucleotide comprises sequence complementary to the first adaptor of the nick translate molecule and also comprises a sequence for binding by a second primer, wherein the second primer binding sequence in the oligonucleotide is 5' to the first adaptor complementary sequence in the oligonucleotide.

25. The method of claim 24, wherein the method further comprises amplifying the primer extended molecule.

26. The method of claim 25, wherein the method further comprises separating the primer extended molecule from the plurality of nick translate molecule.

27. The method of claim 26, wherein the nick translate molecules were generated in the presence of dU nucleotides, the primer extended molecule contains no dU nucleotides, and wherein the separating step comprises degradation of the plurality of nick translate molecules by dU-glycosylase.

28. The method of claim 25, wherein the amplification step comprises polymerase chain reaction using the second primer and a primer complementary to a second adaptor of the nick translate molecule.

29. The method of claim 21, wherein the ligation/primer extension reactions comprise:
(a) ligating in a head-to-tail orientation a plurality of oligonucleotides to form an oligonucleotide assembly, wherein the oligonucleotides are complementary to nick translate molecule sequence that is adjacent to a first adaptor end of the nick translate molecule and wherein the nick translate molecule sequence is present in a subset of the plurality of nick translate molecules, wherein the nick translation molecule has the first adaptor on one terminal end and a second adaptor on the other terminal end;
(b) initiating and extending the primer extension reaction with the 3' end of the oligonucleotide assembly; and
(c) ligating an oligonucleotide to the 5' end of the extension product, wherein the oligonucleotide comprises sequence complementary to the first adaptor of the nick translate molecule and also comprises sequence for binding by a first primer, wherein the first primer binding sequence is 5' to the first adaptor complementary sequence in the oligonucleotide.

30. The method of claim 29, wherein the method further comprises the steps of:
(a) separating the primer extended molecule from the plurality of nick translate molecules; and
(b) amplifying the primer extended molecule.

31. The method of claim 30, wherein the nick translate molecules were generated in the presence of dU nucleotides, the primer extended molecule contains no dU nucleotides, and wherein the separating step comprises degradation of the plurality of nick translate molecules by dU-glycosylase.

32. The method of claim 30, wherein the amplification step comprises polymerase chain reaction using the first primer and a second primer complementary to the second adaptor of the nick translate molecule.

33. The method of claim 21, wherein the primer extension/ligation reaction comprises:
(a) initiating and extending the primer extension reaction with a first primer which is complementary to sequence in a subset of the plurality of nick translate molecules, wherein the nick translate molecule sequence is adjacent to a first adaptor end of the nick translate molecule; and
(b) ligating an oligonucleotide to the 5' end of the extension product, wherein the oligonucleotide comprises:
(1) sequence complementary to the first adaptor of the nick translate molecule;
(2) sequence for binding by a second primer, wherein the second primer binding sequence is 5' to the sequence in (1); and
(3) a label at the 5' end.

34. The method of claim 33, wherein the method further comprises the steps of:
(a) separating the primer extended molecule from the plurality of nick translate molecules by the label of the oligonucleotide; and
(b) amplifying the primer extended molecule.

35. The method of claim 33, wherein the label is biotin.

36. The method of claim 35, wherein the separation further comprises streptavidin-coated magnetic beads.

37. The method of claim 34, wherein the amplification step comprises polymerase chain reaction using the second primer and a third primer complementary to a second adaptor of the nick translate molecule.

38. A method of sequencing nucleic acid, comprising the steps of:
(a) obtaining a DNA sample comprising DNA molecules having a region comprising a known nucleic acid sequence;
(b) partially cleaving the DNA molecules with a sequence-specific endonuclease to generate a plurality of DNA ends;
(c) separating the cleaved DNA molecules;
(d) generating a first amplifiable nick translation product, wherein the first amplifiable nick translation product comprises an adaptor at each end, wherein one adaptor at one end is defined as a first adaptor having a first adaptor sequence and wherein one adaptor at the other end is defined as a second adaptor having a second adaptor sequence, wherein the nick translation of said first amplifiable nick translation product initiates from a known nucleic acid sequence;
(e) determining at least a partial sequence from said first nick translation product;
(f) generating one or more additional amplifiable nick translation products, wherein said nick translation of said one or more additional amplifiable nick translation products initiates from the partial sequence of a previous nick translation product; and
(g) sequencing the nick translation products, wherein the amplified nick translation product is not subjected to cloning prior to the sequencing reaction.

39. The method of claim 38, wherein the DNA sample is a genome.

40. The method of claim 38, wherein there is a limited amount of DNA sample.

41. The method of claim 38, wherein the amplification is by polymerase chain reaction, and one of the primers for the polymerase chain reaction is used as a primer for the sequencing reaction.

42. The method of claim 38, wherein at least a portion of the first adaptor sequence, the second adaptor sequence, or of both first and second adaptor sequences is removed from the amplified nick translation molecule.

43. The method of claim 42, wherein the removal step comprises subjecting the amplified nick translation molecule to a 5' exonuclease.

44. The method of claim 42, wherein a region of the first adaptor sequence, second adaptor sequence or of both first and second adaptor sequences of the nick translate molecule comprises a dU nucleotide and the removal comprises degradation by dU-glycosylase.

45. The method of claim 42, wherein a region of the first adaptor sequence, second adaptor sequence or of both first and second adaptor sequences comprises a ribonucleotide and the removal comprises degradation by alkaline hydrolysis.

46. The method of claim 44 or 45, wherein the region of the second adaptor sequence is in a 3' region of the second adaptor sequence.

47. A method of providing sequence for a gap in a genome sequence, comprising the steps of:
(a) obtaining a DNA sample of the genome comprising DNA molecules having a region comprising a known nucleic acid sequence adjacent to the gap;
(b) digesting the DNA molecules with a plurality of sequence-specific endonucleases to generate a plurality of DNA ends;
(c) generating a first amplifiable nick translation product, wherein said nick translation of said first amplifiable nick translation product initiates from the known nucleic acid sequence;
(d) determining at least a partial sequence from said first nick translation product; and
(e) generating one or more additional amplifiable nick translation products, wherein said nick translation of said one or more amplifiable nick translation products initiates from the partial sequence of a previous nick translation product, wherein at least one of the amplifiable nick translation products comprises sequence of the gap.

48. The method of claim 47, wherein the genome is a bacterial genome.

49. The method of claim 47, wherein the genome is a plant genome.

50. The method of claim 47, wherein the genome is an animal genome.

51. The method of claim 50, wherein the animal genome is a human genome.

52. The method of claim 48, wherein the bacteria are unculturable.

53. The method of claim 48, wherein the bacteria is present in a plurality of bacteria.

54. A method of producing a library of consecutive overlapping series of nucleic acid sequences from a DNA sample, comprising the steps of:
(a) obtaining the DNA sample comprising a DNA molecule;
(b) digesting the DNA molecule with a first sequence-specific endonuclease to generate a plurality of DNA fragments, wherein at least one DNA fragment has a region comprising a known nucleic acid sequence;
(c) attaching a first adaptor molecule to ends of the DNA fragments to provide a nick translation initiation site, wherein the first adaptor comprises a label;
(d) subjecting the first adaptor-bound DNA fragment to nick translation comprising DNA polymerization and 5'–3' exonuclease activity, wherein the nick translation initiates from the known nucleic acid sequence, to generate a first nick translation product;
(e) isolating the nick translation product by the label;
(f) attaching a second adaptor molecule to the first nick translate product;
(g) determining at least a partial sequence from the first nick translation product; and
(h) generating one or more additional amplifiable nick translation products, wherein said nick translation of said one or more amplifiable nick translation products initiates from the partial sequence of a previous nick translation product.

55. The method of claim 54, wherein the label is biotin and the isolation step is binding to streptavidin-coated magnetic beads.

56. A method of producing a library of consecutive overlapping series of nucleic acid sequences, comprising the steps of:
  (a) obtaining a DNA sample comprising DNA molecules having a region comprising a known nucleic acid sequence;
  (b) partially cleaving the DNA molecules with a sequence-specific endonuclease to generate a plurality of DNA fragments, wherein at least one DNA fragment has a region comprising a known nucleic acid sequence;
  (c) separating the cleaved DNA fragments;
  (d) attaching a first adaptor molecule to ends of the DNA fragments to provide a nick translation initiation site, wherein the first adaptor comprises a label;
  (e) subjecting the first adaptor-bound DNA fragment to nick translation comprising DNA polymerization and 5'–3' exonuclease activity, wherein the nick translation initiates from the known nucleic acid sequence, to generate a first nick translation product;
  (f) isolating the nick translation product by the label;
  (g) attaching a second adaptor molecule to the first nick translate products;
  (h) determining at least a partial sequence from said first nick translation product; and
  (i) generating one or more additional amplifiable nick translation products, wherein said nick translation of said one or more amplifiable nick translation products initiates from the partial sequence of said first nick translation product.

57. The method of claim 55, wherein the separation of the DNA fragments is by size.

58. The method of claim 57, wherein the size separation is by electrophoresis.

* * * * *